US011147490B2

(12) United States Patent
Stevens et al.

(10) Patent No.: US 11,147,490 B2
(45) Date of Patent: Oct. 19, 2021

(54) MONITORING DEVICES, SYSTEMS, AND METHODS FOR DETECTING WETNESS IN A GARMENT

(71) Applicant: RSC Associates, Inc., Bowling Green, OH (US)

(72) Inventors: Thomas Reed Stevens, Palo Alto, CA (US); Ivan J. Goering, Palo Alto, CA (US); Suguru Nishioka, Palo Alto, CA (US)

(73) Assignee: RSC ASSOCIATES, INC., Bowling Green, OH (US)

( * ) Notice: Subject to any disclaimer, the term of this patent is extended or adjusted under 35 U.S.C. 154(b) by 0 days.

(21) Appl. No.: 16/141,590

(22) Filed: Sep. 25, 2018

(65) Prior Publication Data

US 2020/0093411 A1    Mar. 26, 2020

(51) Int. Cl.
*G08B 21/00* (2006.01)
*A61B 5/20* (2006.01)
(Continued)

(52) U.S. Cl.
CPC ............ *A61B 5/202* (2013.01); *A61B 5/0022* (2013.01); *A61B 5/746* (2013.01); *G16H 40/63* (2018.01);
(Continued)

(58) Field of Classification Search
None
See application file for complete search history.

(56) References Cited

U.S. PATENT DOCUMENTS

| 6,419,665 B1 | 7/2002 | Cohen |
| 7,053,781 B1 | 5/2006 | Haire et al. |
| (Continued) | | |

FOREIGN PATENT DOCUMENTS

| WO | 2014/165041 A2 | 10/2014 |
| WO | 2015/137999 | 9/2015 |
| WO | 2018/098300 A1 | 5/2018 |

OTHER PUBLICATIONS (PCT) Korean Intellectual Property Office (ISA/KR), International Search Report, International Application No. PCT/US2017/063042, 3 pages, dated Feb. 8, 2018.
(Continued)

*Primary Examiner* — Julie B Lieu
(74) *Attorney, Agent, or Firm* — Thompson Hine LLP

(57) ABSTRACT

A monitoring device for detecting wetness in a garment is disclosed. The monitoring device of the present disclosure includes a clip removably attachable to the garment and having a printed circuit board and a plurality of pins in communication with the printed circuit board, a portion of the plurality of pins extending through a portion of the clip, wherein the plurality of pins include a first pin, a second pin, and a third pin, the first pin and the second pin aligned along a first axis of the clip and the third pin aligned along a second axis of the clip, the second axis spaced from the first axis, wherein, with the clip attached to the garment, the printed circuit board is in communication with the garment via the plurality of pins. Transmitters having built-in delay mechanisms configured to delay transmitting operational data for a period of time are also disclosed. The operational data may include moisture data and detachment information. Methods for determining operational data for a monitoring device for detecting wetness in a garment are also disclosed.

14 Claims, 42 Drawing Sheets

(51) Int. Cl.
  *A61B 5/00* (2006.01)
  *G16H 40/67* (2018.01)
  *G16H 40/63* (2018.01)

(52) U.S. Cl.
  CPC ...... *G16H 40/67* (2018.01); *A61B 2560/0406* (2013.01); *A61B 2562/029* (2013.01)

(56) References Cited

U.S. PATENT DOCUMENTS

| | | | |
|---|---|---|---|
| 10,111,590 B2 | 10/2018 | Thoen | |
| 2004/0230172 A1 | 11/2004 | Shapira | |
| 2005/0033250 A1 | 2/2005 | Collette et al. | |
| 2005/0156744 A1 | 7/2005 | Pires | |
| 2005/0195078 A1* | 9/2005 | Basinger | G08B 25/002 340/521 |
| 2007/0242614 A1* | 10/2007 | Buettner | H04L 1/0061 370/248 |
| 2007/0252713 A1 | 11/2007 | Rondoni et al. | |
| 2008/0262453 A1 | 10/2008 | McGinnis et al. | |
| 2008/0278336 A1 | 11/2008 | Ortega et al. | |
| 2009/0326417 A1 | 12/2009 | Ales, III et al. | |
| 2010/0173604 A1* | 7/2010 | Hofmann | G08B 27/008 455/404.1 |
| 2012/0206265 A1 | 8/2012 | Solazzo et al. | |
| 2013/0187686 A1* | 7/2013 | Yuan | H03K 3/0375 327/117 |
| 2015/0042489 A1 | 2/2015 | Lavon | |
| 2016/0374607 A1* | 12/2016 | Berland | A61B 5/7235 702/19 |
| 2017/0156594 A1* | 6/2017 | Stivoric | A61B 5/7275 |
| 2018/0049668 A1* | 2/2018 | Defant | A61B 5/097 |

OTHER PUBLICATIONS (PCT) Korean Intellectual Property Office (ISA/KR), Written Opinion of the International Searching Authority, International Application No. PCT/US2017/063042, 8 pages, dated Feb. 8, 2018.
(PCT) U.S. Patent and Trademark Office, International Search Report, International Application No. PCT/US2019/052933, 4 pages, dated Jan. 31, 2020.
(PCT) U.S. Patent and Trademark Office, Written Opinion of the International Searching Authority, International Application No. PCT/US2019/052933, 6 pages, dated Jan. 31, 2020.
(US) U.S. Patent and Trademark Office, Non-Final Office Action, U.S. Appl. No. 16/463,032, 16 pages, dated Jan. 20, 2020.
(EP) European Patent Office, Search Report and Opinion, European Patent Application No. 17874641.8, 13 pages, dated Jun. 17, 2020.
Anonymous, "Superabsorbent polymer," Wikipedia, 5 pages, URL: https://en.wikipedia.org/w/index,php?title=Superabsorbent_polymer&oldid=750686763, 2016.

* cited by examiner

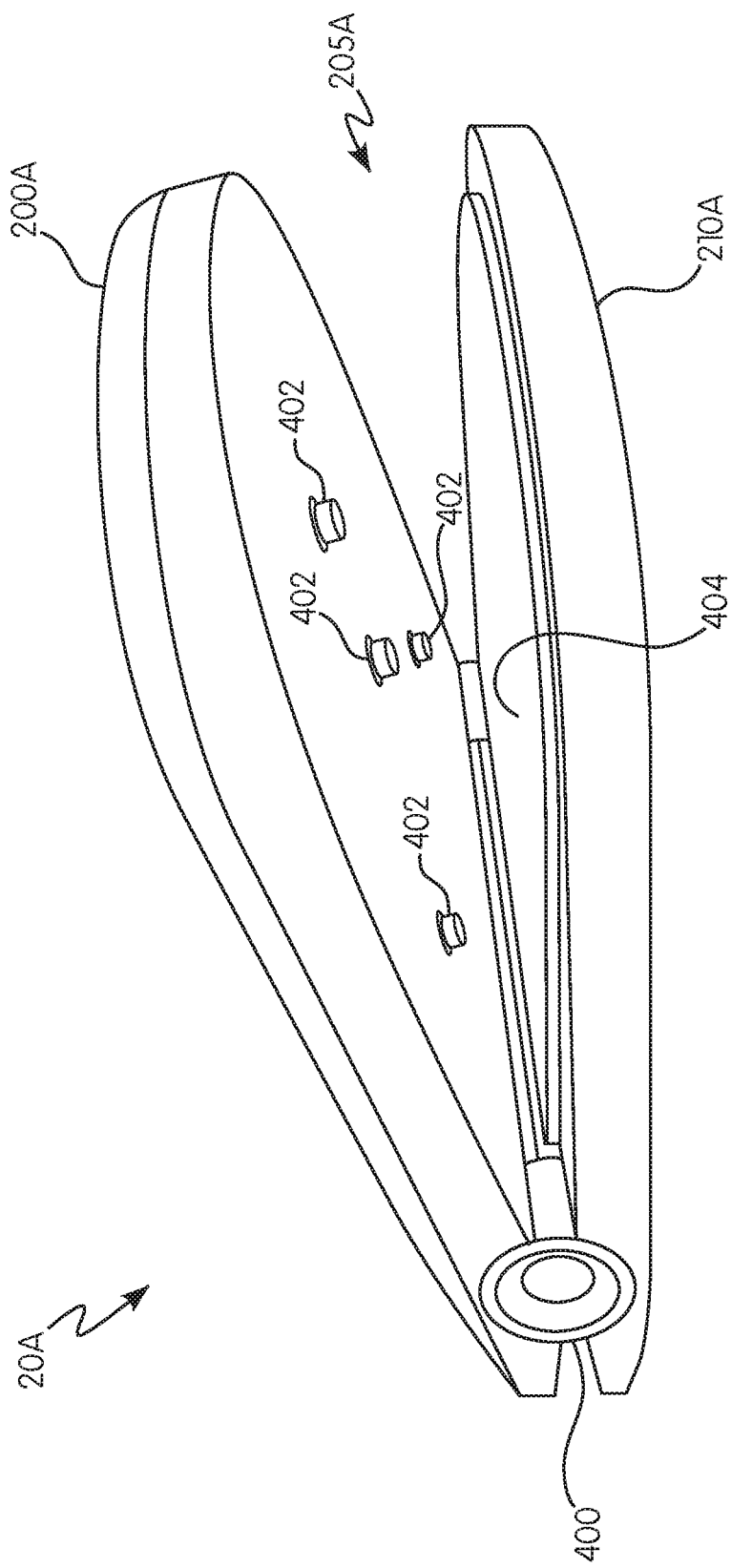

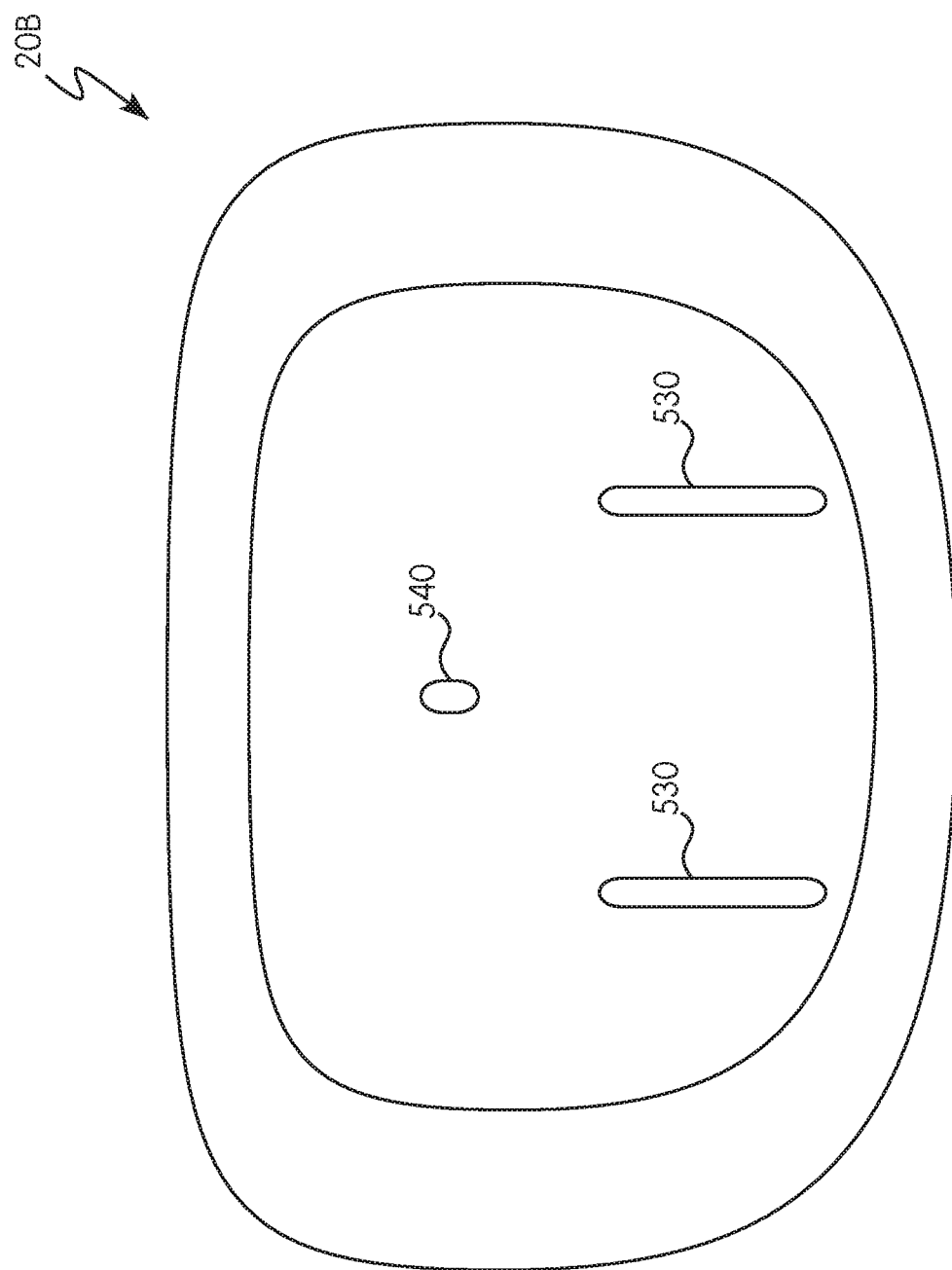

MONITORING DEVICES, SYSTEMS, AND METHODS FOR DETECTING WETNESS IN A GARMENT

COPYRIGHT NOTIFICATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Disclosure

The present disclosure relates generally to monitoring devices, systems, and methods. More particularly, the present disclosure relates to monitoring devices, systems, and methods for detecting wetness in a garment for tracking patient incontinence.

2. Description of the Related Art

Incontinence in patient care environment is a growing problem in patient care and home care of elderly patients. Urinary incontinence is the involuntary leakage of urine. Many patients have the inability to hold urine in their bladder because voluntary control over the urinary sphincter is either lost or weakened. Urinary incontinence is a much more common problem than most people realize.

It is common for nursing homes and hospitals to lack the staff and financial resources to provide residents with sufficiently frequent toileting assistance (including prompted voiding). Use of special undergarments and absorbent pads or catheterization is the usual practice.

Urinary incontinence (UI) and fecal incontinence (FI) are commonly encountered in nursing home residents and are associated with significant morbidity and utilization of health care resources. Urinary incontinence has been estimated to affect between 50% and 65% of nursing home residents, and a majority of these residents also have FI. UI is also prevalent in the at-home aging population and is a leading factor in senior isolation and eventual institutionalization in a care facility.

There are several key activities of daily living (ADL) that are indicative of quality of life and safety in an aging population including: toileting, sleep, medication, and nutrition. Incontinence is a critical ADL deficit that negatively impacts all aspects of autonomy, health, and overall well-being. It is a leading cause of seniors' loss of independence and requiring professional care. The demand for improved incontinence solutions exist, in ever increasing levels of severity, at every stage in elder care from family caregiving through to acute care hospitalization, with the highest utilization rates occurring in long-term living facilities. Sleep quality is another key indicator that augments and interrelates with incontinence.

Elderly people constitute a large and growing portion of the world's population. Many of them are physically and mentally vulnerable and need continuous support for their health and well-being. There is a growing trend that these elderly people are placed in an ambient assisted living environment (AAL) with an aim to receive better care and support. However, much less attention has been directed toward understanding incontinence needs of elderly people, which is an important factor relevant to their physical and mental health and joyful living.

One in three adult women live with some level of urinary incontinence. Nearly 40% (19 million) of all seniors and over 60% (15 million) of female seniors live with incontinence, with increasing prevalence and severity as age increases. Suboptimal incontinence care leads to degenerative skin health, an increased risk of falls as patients unsuccessfully attempt to self-toilet, and critical declines in mental health. As a result, it is the leading cause of senior isolation and institutionalization. Clinical nurses and the research community agree that there is clear correlation between incontinence and pressure ulcers and urinary tract infections (UTIs). UTIs and pressure wounds are directly linked to increased negative outcomes.

The cost to treat pressure ulcers can be very expensive and is estimated between $9.1-11.6 billion per year, affecting over 2.5 million patients. Approximately 60,000 people die each year as a direct result of a pressure ulcer. Keeping the skin free from exposure to urine and stool is very important in treating pressure ulcers and bedsores. Similarly, UTIs are rampant as well, as a result of over-catheterization, totaling over $340 million per year and with at least 13,000 deaths a year associated with UTIs. Increased costs and negative outcomes with UTIs are likely as the patient population grows older. The known solutions that demonstrate improvement in these costs and outcomes are needed.

For enterprise businesses, incontinence is a significant issue. For caregivers, such as acute care hospitals, incontinence is a contributor to revenue loss and a key source of family dissatisfaction with institutional providers. Nearly $4 billion is spent on adult non-woven absorbency products in the US ($9 billion globally), and the segment is growing as the Baby Boomers continue to age and live longer than their predecessors.

It is known that the complications of urinary incontinence are increasingly and rapidly expanding as the world's population is aging longer with each new year. Many elderly people encounter skin problems, but an elderly person with urinary incontinence is even more likely to have skin sores, rashes, and infections because the skin is wet or damp. This is bad for wound healing and also promotes fungal infections. UTI's are a significant risk and long-term use of urinary catheters also significantly increase the risk of infection.

The problem has been addressed in part by providing pads that are manually replaced when the nurse is visiting a room. The amount of times a product needs changed depends in part on how absorbent the pad, diaper, or pull-up is and the severity of the incontinence. Generally, it is best to change a product as soon as soiling occurs. This will reduce the risk of skin breakdown and infections caused by a lack of air flow, moist conditions, and long exposure to urine and fecal matter.

With each change, it is important to thoroughly clean the diaper area to reduce infections. After changing, it is important to properly dispose of soiled incontinence products.

Disposable briefs are more commonly known as adult diapers. Adult diapers are often used for heavy incontinence, nighttime wetting, and those who need help getting to the bathroom.

Therefore, there is a need to provide a method and an apparatus for improved incontinence sensing. Thus, there remains a considerable need for pads with improved incontinence sensing and systems that can quickly and accurately address a patient with a wet pad.

SUMMARY OF THE INVENTION

There currently exists a need for sensor pad systems for managing incontinence adapted to new patient care facilities. Systems for coupling complex sensor pads with software tracking systems and monitoring systems are also needed. In care facilities today, only manual systems exist for the management and maintenance of patient bedding. Many care facilities have no way to determine, monitor, and schedule service and visits based on the real time needs of the patient. Often patients are left in their own urine and feces for extended periods of time, causing many health problems. This leads to increased demands for alternative, pad based incontinence solutions.

There currently exists a need for incontinence protection having improved in the effectiveness at drawing moisture away from the body and keeping odors at bay. In addition, a need exists for maintaining skin health by keeping the perineal area dry and making sure the smell of urine or feces doesn't become noticeable to others, which is essential to maintaining quality of life—both physically and emotionally.

The present disclosure is directed to a monitoring device for detecting wetness in a garment. The monitoring device of the present disclosure includes a clip removably attachable to the garment and having a printed circuit board and a plurality of pins in communication with the printed circuit board, a portion of the plurality of pins extending through a portion of the clip, wherein the plurality of pins include a first pin, a second pin, and a third pin, the first pin and the second pin aligned along a first axis of the clip and the third pin aligned along a second axis of the clip, the second axis spaced from the first axis, wherein, with the clip attached to the garment, the printed circuit board is in communication with the garment via the plurality of pins.

The present disclosure is also directed to transmitters having built-in delay mechanisms configured to delay transmitting operational data for a period of time. The operational data may include moisture data and detachment information. The present disclosure is also directed to methods for determining operational data for a monitoring device for detecting wetness in a garment.

In accordance with an embodiment of the present disclosure, a monitoring device for detecting wetness in a garment includes a sensor configured to determine operational data associated with the monitoring device, and a transmitter configured to connect to the sensor and transmit the operational data to a computer system comprising one or more processors, wherein the transmitter is configured to delay transmitting the operational data for a period of time, wherein a first reading including the operational data is transmitted in the absence of a contradictory second reading being subsequently sensed within the period of time, and wherein the first reading including the operational data is not transmitted with the second reading being subsequently sensed within the period of time.

In one configuration, the operational data is moisture data associated with moisture in a pad. In another configuration, the first reading is a wet reading and the second reading is a dry reading. In yet another configuration, the transmitter is configured to delay transmitting the moisture data for a period of time based on the moisture data indicating a dry reading after a wet reading. In one configuration, the period of time is approximately five (5) seconds. In another configuration, the operational data is detachment information associated with the monitoring device being attached to the garment. In yet another configuration, the first reading is a detachment reading and the second reading is an attachment reading. In one configuration, the transmitter is configured to delay transmitting the detachment information for a period of time based on the detachment information indicating an attachment reading after a detachment reading. In another configuration, the period of time is approximately three (3) seconds.

In accordance with another embodiment of the present disclosure, a monitoring device for detecting wetness in a garment includes a sensor configured to determine moisture data associated with moisture in a pad, and a transmitter configured to connect to the sensor and transmit the moisture data to a computer system comprising one or more processors, wherein the transmitter is configured to delay transmitting the moisture data for a period of time, wherein a wet reading is transmitted in the absence of a dry reading being subsequently sensed within the period of time, and wherein the wet reading is not transmitted with the dry reading being subsequently sensed within the period of time.

In one configuration, the transmitter is configured to delay transmitting the moisture data for a period of time based on the moisture data indicating a dry reading after a wet reading. In another configuration, the period of time is approximately five (5) seconds.

In accordance with another embodiment of the present disclosure, a monitoring device for detecting wetness in a garment includes a sensor configured to determine detachment information associated with the monitoring device being attached to the garment, and a transmitter configured to connect to the sensor and transmit the detachment information to a computer system comprising one or more processors, wherein the transmitter is configured to delay transmitting the detachment information for a period of time, wherein a detachment reading is transmitted in the absence of an attachment reading being subsequently sensed within the period of time, and wherein the detachment reading is not transmitted with the attachment reading being subsequently sensed within the period of time.

In one configuration, the transmitter is configured to delay transmitting the detachment information for a period of time based on the detachment information indicating an attachment reading after a detachment reading. In another configuration, the period of time is approximately three (3) seconds.

In accordance with another embodiment of the present disclosure, a method for determining operational data for a monitoring device for detecting wetness in a garment includes sensing with a sensor moisture data associated with moisture in a pad; connecting a transmitter to the sensor, the transmitter for transmitting the moisture data to a computer system comprising one or more processors; delaying the transmitter from transmitting the moisture data to the computer system for a period of time; transmitting the moisture data including a wet reading to the computer system in the absence of a dry reading being subsequently sensed within the period of time.

In one configuration, the wet reading is not transmitted with the dry reading being subsequently sensed within the period of time. In another configuration, the period of time is approximately five (5) seconds.

In accordance with another embodiment of the present disclosure, a method for determining operational data for a monitoring device for detecting wetness in a garment includes sensing with a sensor detachment information associated with the monitoring device being attached to the garment; connecting a transmitter to the sensor, the transmitter for transmitting the detachment information to a computer system comprising one or more processors; delaying the transmitter from transmitting the detachment information to the computer system for a period of time; and transmitting the detachment information including a detachment reading to the computer system in the absence of an attachment reading being subsequently sensed within the period of time.

In one configuration, the detachment reading is not transmitted with the attachment reading being subsequently sensed within the period of time. In another configuration, the period of time is approximately three (3) seconds.

In accordance with another embodiment of the present disclosure, a monitoring device for detecting wetness in a garment, comprising: a clip removably attachable to the garment, the clip comprising: a printed circuit board contained within the clip; and a plurality of pins in communication with the printed circuit board, a portion of the plurality of pins extending through a portion of the clip, wherein the plurality of pins include a first pin, a second pin, and a third pin, the first pin and the second pin aligned along a first axis of the clip and the third pin aligned along a second axis of the clip, the second axis spaced from the first axis, wherein, with the clip attached to the garment, the printed circuit board is in communication with the garment via the plurality of pins.

In one configuration, the garment includes a first line and a second line spaced from the first line. In another configuration, with the clip attached to the garment, the first pin and the second pin communicate with the first line and the third pin communicates with the second line. In yet another configuration, with the first pin and the second pin in communication with the first line of the garment, an attachment reading is generated. In one configuration, with one of the first pin and the second pin not in communication with the first line of the garment, a detachment reading is generated. In another configuration, the monitoring device includes a locking mechanism movably connected to the clip, the locking mechanism transitionable between a first position in which the locking mechanism locks the clip in a closed position and a second position in which the clip is in an open position.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 8A is a perspective view of a transmitter in an open position in accordance with another embodiment of the present invention.

FIG. 9B is a side elevation view of the transmitter in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
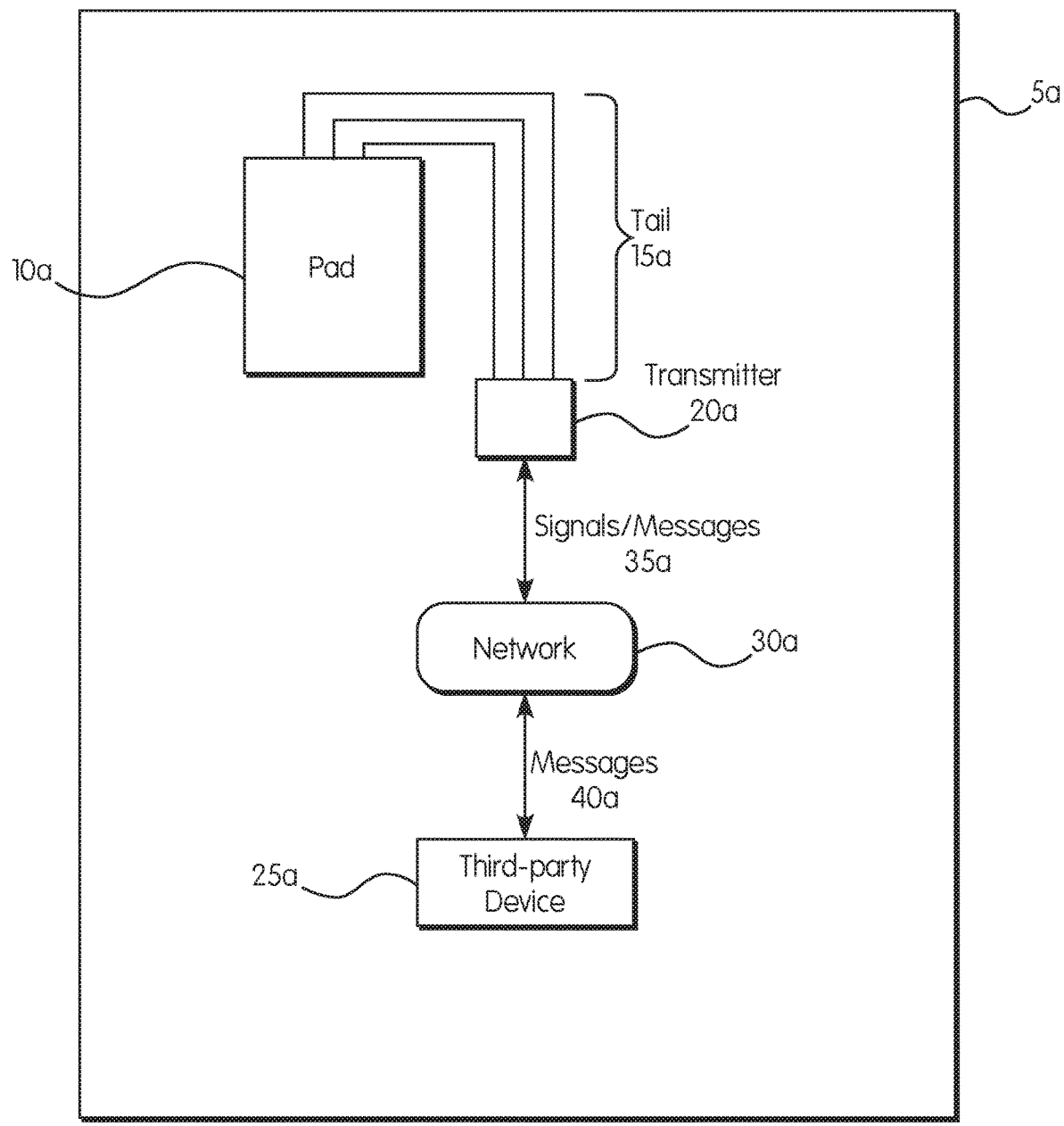
FIG. 1 is a diagram showing a Patient Incontinence Monitoring System in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present disclosure provides a Patient Incontinence Monitoring System for electronically detecting the presence of moisture in a patient care or home care environment. It can send a detection of moisture across a network to a third-party device 25a (e.g., a computer, a remote pad, a smartphone, a cloud) for enabling the remote collection and analysis of incontinence data. This detection can also be used by a third-party device 25a, such as a monitoring system, to determine patterns and/or alert a caregiver associated with an incontinence event.

With reference to FIG. 1, a Patient Incontinence Monitoring System 5a includes a multi-layer sensor pad 10a, a tail 15a, and a transmitter 20a. The tail 15a extends from the sensor 10a and is operative to connect the transmitter 20a to the multi-layer location-based sensor pad 10a to read signals 35a from pad 10a and transmits pad data in the form of signals and/or messages 35a across a network 30a to a third-party device 25a, such as internet service, cloud service, hosted or standalone computer, iPad, smartphone, database, or other transmitter/repeater. The third-party device 25a uses the pad data to determine that moisture is present and begins to track and/or monitor the moisture on the multi-layer location-based sensor pad 10a. The third-party device can be a specially programmed computer intended to utilize the sensor pad data of multi-patient environments.

The tail 15a is integrated with the pad itself. In a preferred embodiment, the tail 15a is formed as part of the sensor pad 10a, created within the manufacturing process of the pad 10a. The sensors of the pad are printed onto a flexible material and then joined with the other layers of the sensor pad 10a. In an alternate embodiment, not shown, the sensors can be attached using an adhesive or some other material or compound to fasten the sensor. In a preferred embodiment, a unitary sensor is used to form the pad 10a and the tail 15a. The tail forms an extension of the sensor from the body of the pad sensor and provides length and flexibility to reach and connect to the transmitter 20a. The transmitter-tail interface provides a soft point of failure for the transmitter and pad combination to 'fail' in the instance of a fall or tripping hazard situation. In contrast to a hard flex circuit or some sort of materially strong connection between the pad and the transmitter that creates a fall hazard, the tail 15a is defined to easily and quickly tear or pull from the transmitter to avoid accidents, such as falling. The flexible tail 15a is formed by perforating a part of the material that divides the tail portion from the body portion of the sensor pad, for example, a line forming a path between the sensors of the tail and the sensors of the body. When the perforation is detached a flexible tail is formed, extending from the sensor pad and manipulatably flexible for connecting to a transmitter 20a. The tail 15a can also be easily removed after the pad 10a has been consumed. The tail 15a is easily torn from the pad body while the tail 15a is still connected to the transmitter 20a. The pad body can be easily disposed of, leaving the transmitter which can be removed after the old tail is removed and disposed.

Figure 2A:
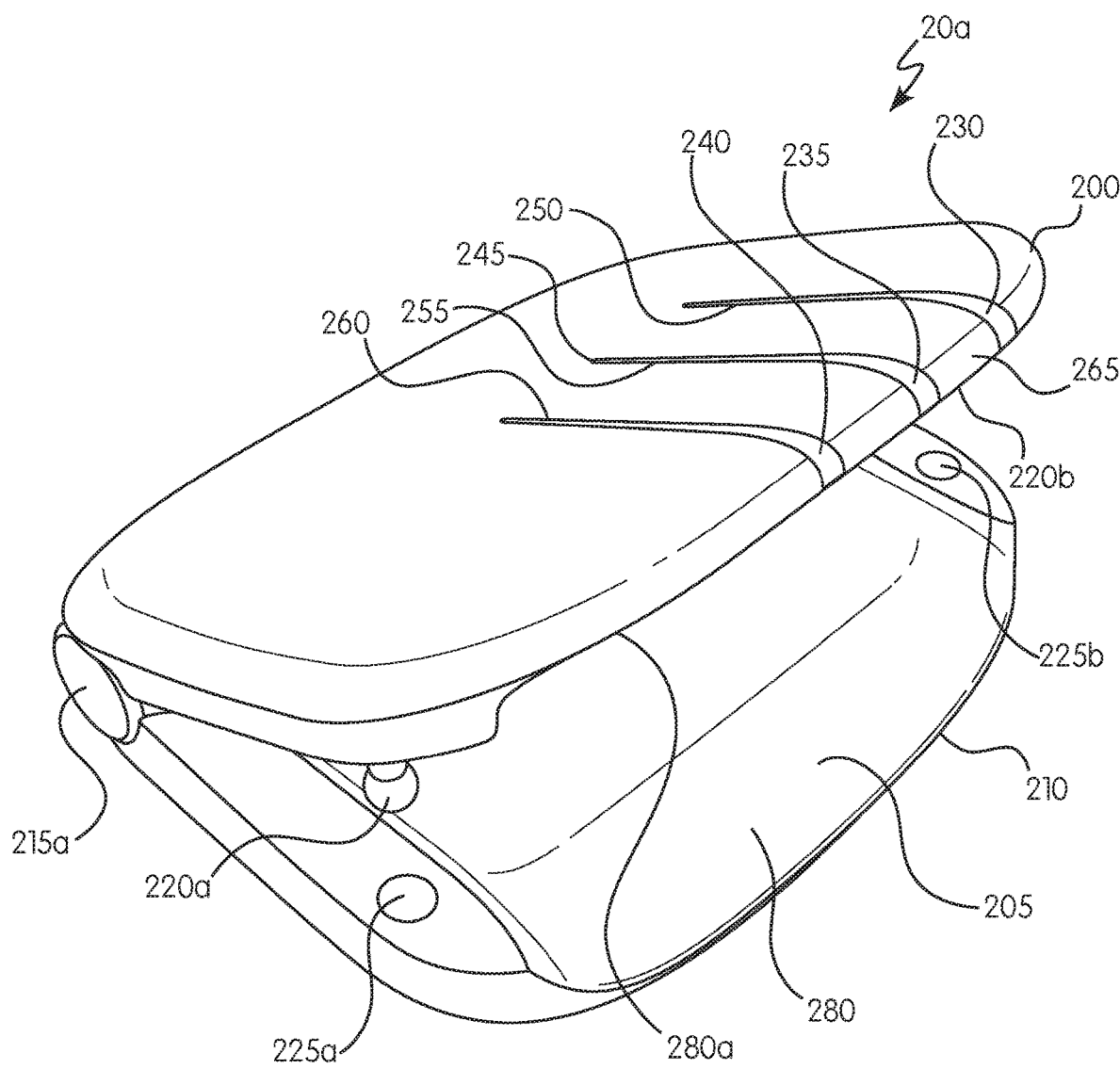
FIG. 2A is a perspective view of a transmitter in an open position in accordance with an embodiment of the present invention.

With reference to FIG. 2A, the transmitter 20a has a smoothed, rounded top panel 200 and a smooth, rounded bottom panel 210 that are connectably secured together by a movable connecting piece 215a, 215b (shown in FIG. 2D), forming a clamshell with congruent joints on either end. Such a shape of the upper surface 200 increases ergonomics of the transmitter, its curvature following the natural curvature of the human hand, thereby enhancing grasping comfort. The movable connecting pieces 215a, 215b are inserted into circular openings 270a and 270b (shown in FIG. 2E) in the top panel 200 and mirrored circular openings formed in the bottom panel 210, the movable connecting pieces 215a, 215b form an axis of a rotation about the joint, where the panels move about the axis, to open and close, by rotating the panels 200, 210, relative to each other. Both the top panel 200 and the bottom panel 210 have rounded edges and internally curved inside surfaces formed on the internal surfaces of panels 200, 210, that face each other, such that when the pieces are closed together a cavity 205 is formed (shown in FIG. 2B). The internally curved insides are stepped internally down such that an inner portion 280 is thinner than the outer portion. This design facilitates the receiving of a tail region 15a as shown in FIG. 1. Extending outward from the top panel 200 is a male connector 220a on one side and male connector 220b on the other side. Extending outward from bottom piece 210, and directly opposite the male connectors of top panel 200, are female openings 225a, 225b. The male connectors 220a, 220b form a locking connection between the panels 200, 210 when they are inserted into the mating female openings 225a, 225b and received therein. However, one of ordinary skill in the art would recognize that locking surfaces can be formed with other means, where the transmitter may be closed and secured.

In one embodiment, the transmitter is side hinged, and instead of the tail running through the middle of the transmitter and out the back under the hinge, the hinge is to one side of the tail and the transmitter clamps across it from the side.

Figure 2B:
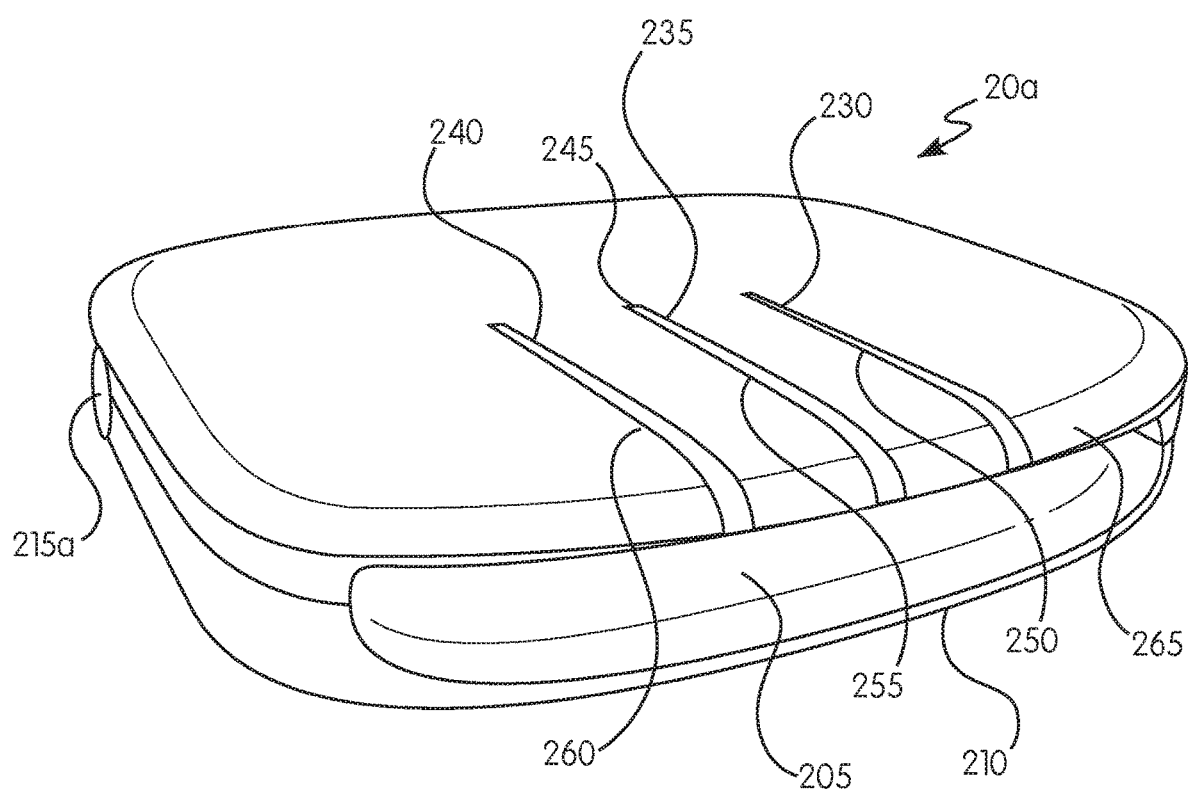
FIG. 2B is a perspective view of the transmitter in a closed position, with male connectors and female connectors, in accordance with an embodiment of the present invention.
Figure 2C:
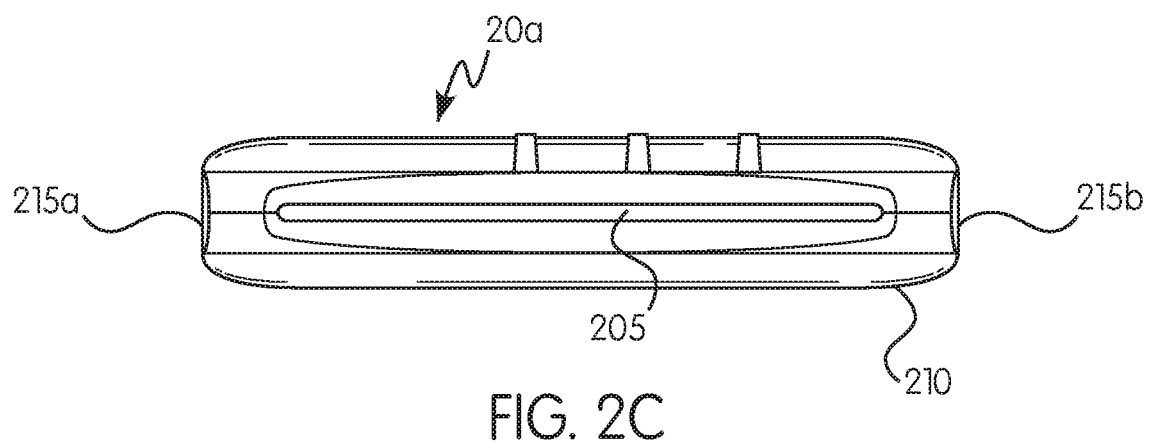
FIG. 2C is a front elevation view of the transmitter in a closed position in accordance with an embodiment of the present invention.
Figure 2D:
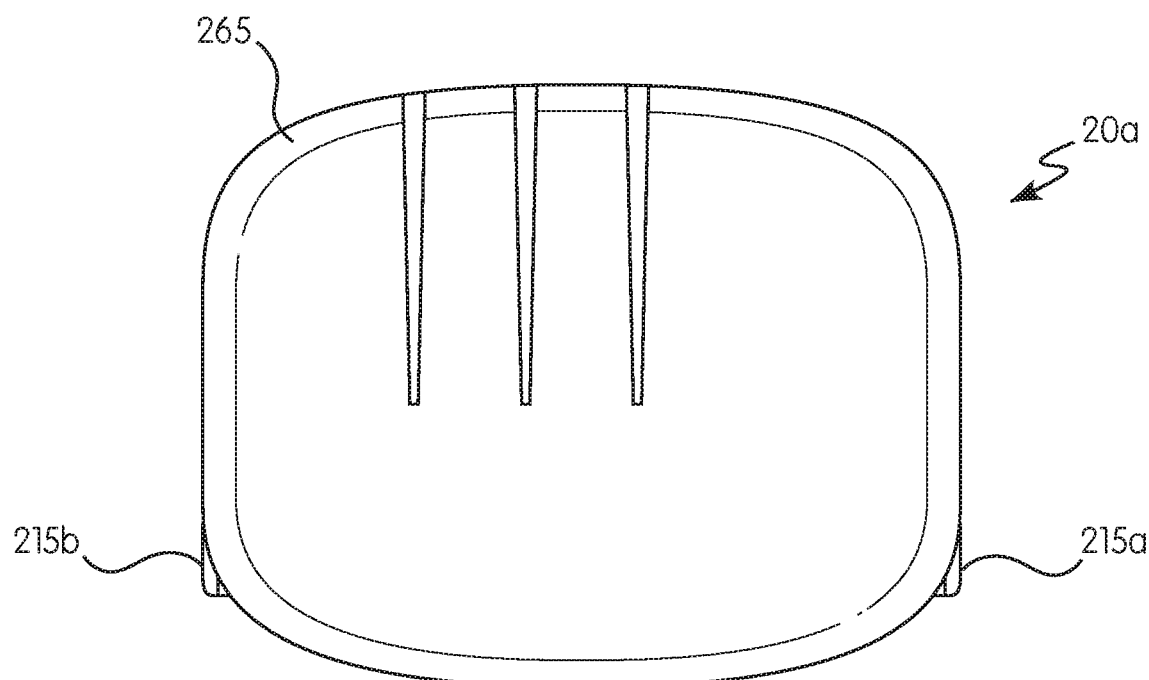
FIG. 2D is a top elevation view of the transmitter in accordance with an embodiment of the present invention.
Figure 2E:
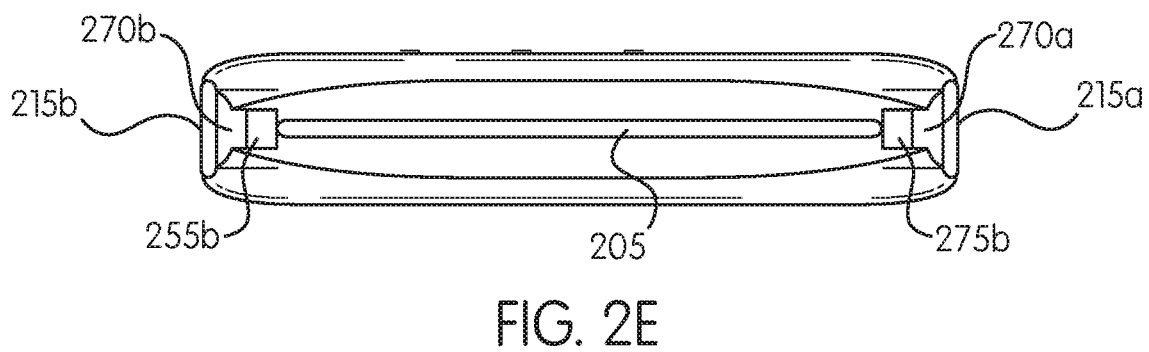
FIG. 2E is a rear elevation view of the transmitter in accordance with an embodiment of the present invention.
Figure 2F:
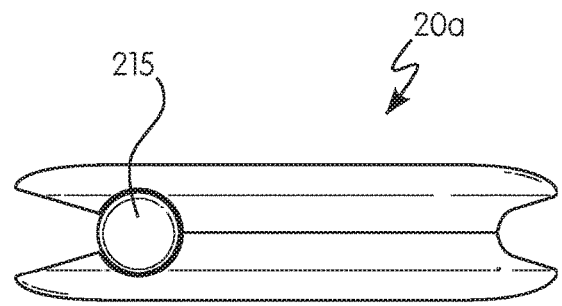
FIG. 2F is a side elevation view of the transmitter, with movable connecting pieces, in accordance with an embodiment of the present invention.

With reference to FIGS. 2B-2F, the transmitter 20a of FIG. 1 is shown from various angles. Referring to FIG. 2B, the transmitter 20a, as previously discussed, is closed by inserting male connectors 220a, 220b into the female connectors 225a, 225b, respectively (shown in FIG. 2A). The closing of the transmitter 20a will create the cavity 205 through the closed transmitter 20a. The closing of the transmitter 20a and creation of the cavity 205 for receiving the tail 15a inserted through and connected to the transmitter 20a (discussed in more detail later). With reference to FIG. 2C, the transmitter 20a is shown from the front, and having an opening where the tail end can be inserted into the transmitter 20a. With reference to FIG. 2D, the transmitter 20a is shown from the top such that the curved edges of the top panel 200 can be easily realized. In other words, the upper surface is curved more near its ends where the degree of curvature is increased, and more flat in the vicinity of its middle, where the radius of curvature is less. Such a shape of the surfaces of the panels increases ergonomics of handling the transmitter, its curvature following the natural curvature of the human hand, thereby enhancing grasping comfort. FIG. 2E shows the smart transmitter from the back to show the back opening where the tail end may come out. FIG. 2F shows the transmitter 20a from the right such that the movable connecting pieces 215a, 215b can be seen along with the top panel 200 and the bottom piece 210 closed down.

As shown in FIGS. 2C and 2E, the cavity 205 is the same width throughout the transmitter 20a such that the tail 15a (not shown) can be inserted through at the same width. However, this is not meant to be construed in a limiting sense and the cavity 205 may be the same or different widths throughout the transmitter 20a. Grooves or lines on the transmitter are used to provide a visual cue that the user correctly handles the alignment of the pad ribbon with the transmitter contacts. Such an inclination improves the ergonomics of the transmitter 20a, especially in the open and close position where the lines of the smoothed top and bottom panels 200, 210 are complimenting the internal cavity and path there through for connecting the tail of the sensor pad to the transmitter. The ergonomic design of the top and bottom provide stability for holding and positioning the tail therein, the rounded surfaces ergonomically easing the use of the transmitter. In one embodiment, the length of the first and second edge are 100 mm and 80 mm, a height of 20 mm, with a 30 degree opening in the back end of the transmitter, whereas the cavity has an opening of less than 20 mm in height when closed.

There is an LED indicator by the logo that flashes green when a pad is connected to indicate that the contacts have made contact with the pad. The LED will then flash red when moisture is detected on the pad providing a visual local indicator, and also when the transmitter has not been properly connected to a new pad (i.e., it will not 'go green' until it connects to a new dry pad).

Referring again to FIG. 2A, three connectors 230, 235, 240 are inserted into the top panel 200 of the transmitter 20a. Each connector is inserted into a formed connector opening formed on the top surface such that when the connector running parallel from the top panel 200 down to a front edge 265 is inserted into the connector cavity the connector is flush with the top panel 200. As shown in FIG. 2A, the connectors 230, 235, 240 are inserted into connector openings 250, 255, 260, respectively, formed in the top surface. The connectors 230, 235, 240 are attached to the transmitter 20a and wired to the boards. For example, the connectors 230, 235, 240 can be glued or snapped onto the transmitter 20a. Also shown in FIG. 2A, connector 245 sits internal to the transmitter 20a at the top of connector 235. The contacts are mounted to the circuit board and protrude from holes formed during injection molding. These contact pins are inside the clamshell with the tail going through the shell like a belt in a buckle. The three stripes on the exterior of the transmitter are a visual queue for quick functional alignment. The contacts are connected directly to the control board and provide the electrical charge, as well as through the coupling of the board and the sensor pad. The connectors can be formed of prongs on an internal surface. In one embodiment, at least two of the prongs hit grounding trace. They can create a short contact coupling used to communicate that the tail 15a is plugged into the transmitter 20a correctly. That connection is keeping the outer ring charged all the time. Because the thing is on all the time, this drops the impedance level into the range that it is tuned for. When that happens, it wakes up the processor.

Figure 2G:
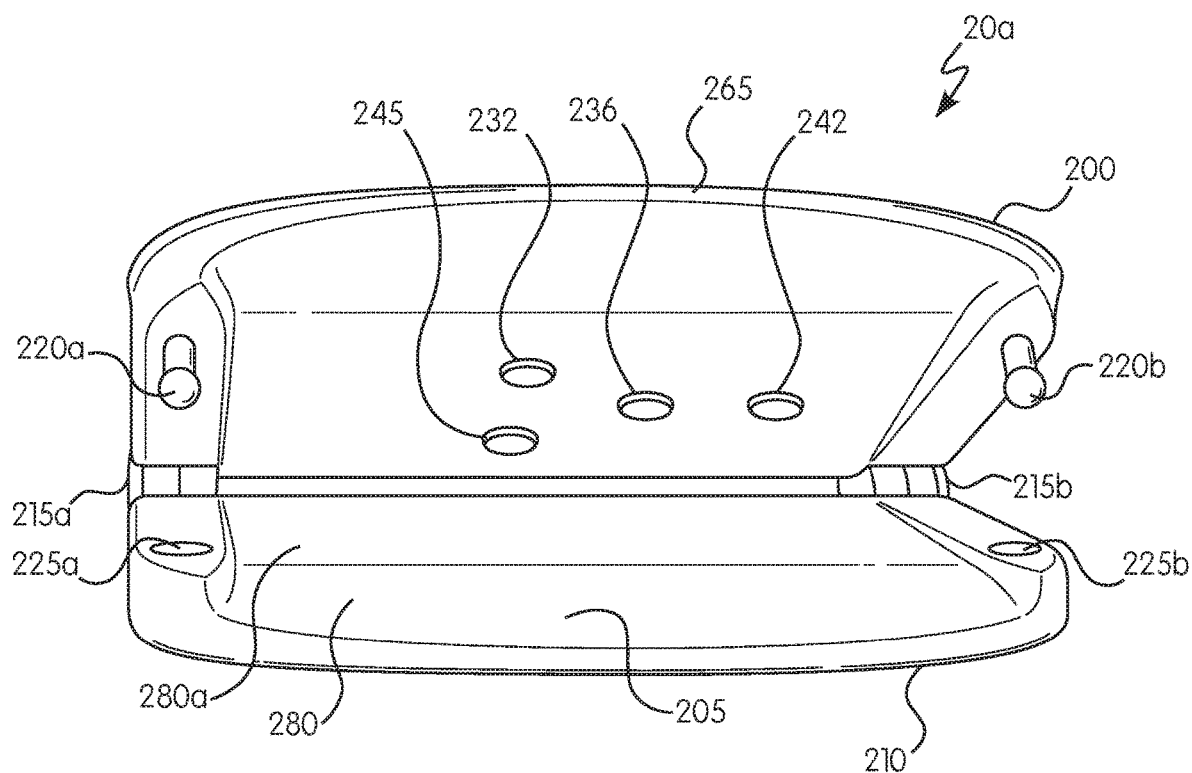
FIG. 2G is a perspective view of the transmitter in an open position, with connecting pieces, in accordance with an embodiment of the present invention.

With reference to FIG. 2G, the smart transmitter 20a is clamped onto the tail 15a aligning physical connectivity for the connectors 230, 235, 240, with the sensors, 30b, 35b, 40b (FIG. 4), on the tail 15a. The connectors 230, 235, 240 on the transmitter 20a have conductive pins 232, 236, and 242 that are pressed against the electric sensors 30b, 35b, 40b and coupling with them to create the electrical connection. Through the connection, the smart transmitter 20a receives the moisture information from the sensors 30b, 35b, 40b. The conductive pins 232, 236, 242 can be blunt or machined as shown in FIG. 2G or alternatively, in another embodiment, the conductive pins can have a sharp edge or point that can penetrate the sensors 30b, 35b, 40b to form a connection.

Figure 3A:
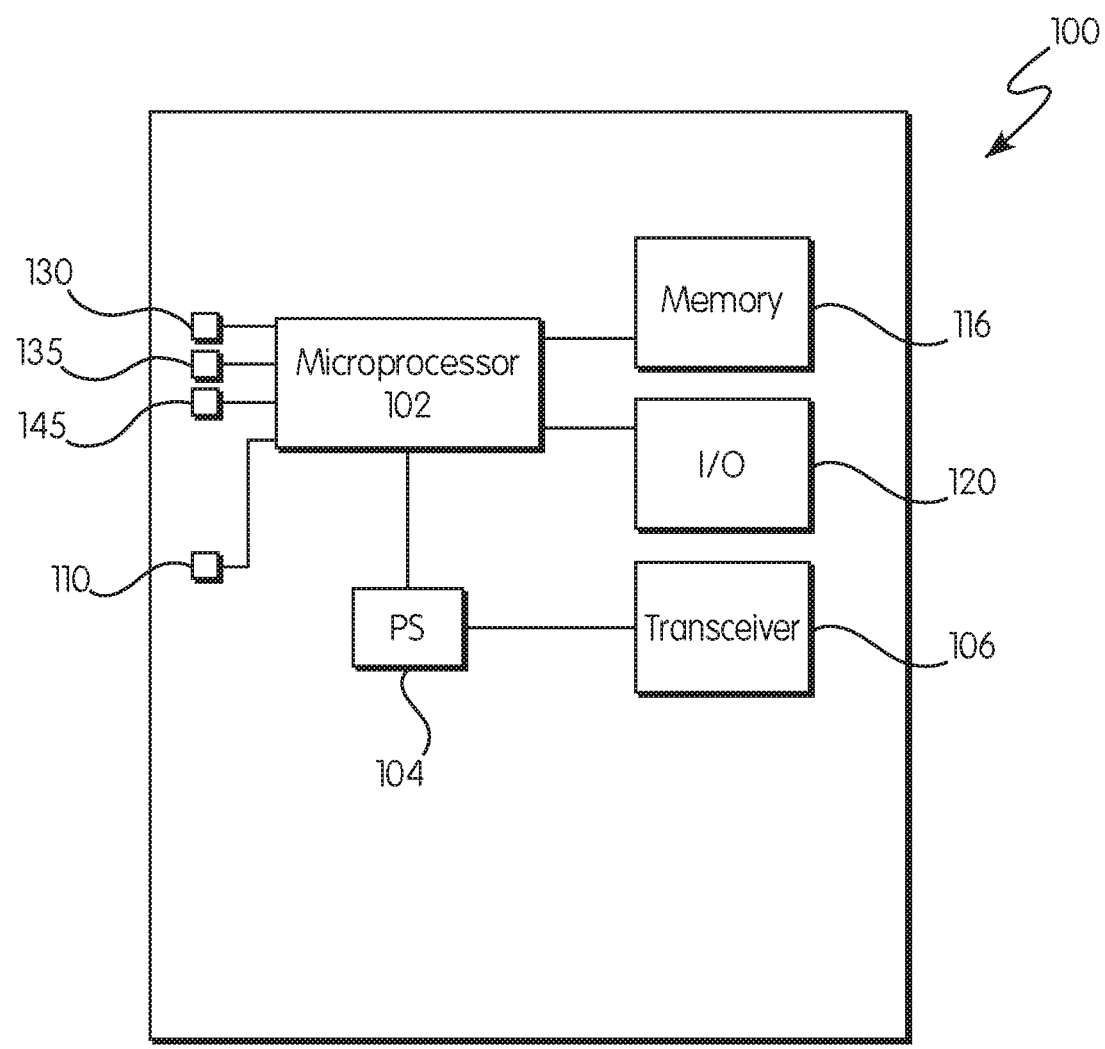
FIG. 3A is a block diagram of the internal transmitter in accordance with an embodiment of the present invention.

The transmitter 20a of FIG. 1 includes a board 100, shown in FIG. 3A. The board 100 has a power supply 104, a microprocessor 102, a transceiver 106, internal connectors 130, 135, 145, memory 116, and input/output 120. The power supply 104 can be any conventional circuit for providing, controlling, converting, measuring, and/or detecting a voltage and/or current. One of skill in the art would understand other sources of power besides a battery could be used, such as traditional plug and socket or other adapter, a power outlet, green, or USB type connection, to provide electrical energy. The transmitter 20a includes a memory 116 for data and instruction storage. In an embodiment, information relating to the specific device platform (e.g., ID information, history) and/or patient information (name, age, moisture frequency, social security number) is stored on the board memory. The internal connectors 130, 135, 145 connect to the connectors 230, 235, 240 (shown on FIGS. 2A and 2B) on the transmitter 20a and relay sensor information or messages to the microprocessor 102. The transceiver 106 receives the sensor information or messages which can then be transmitted to the network and then to a third-party device 25a. The input/output 120 is coupled to the microprocessor 102 and allows for a user to input additional sensor data. According to a non-limiting embodiment or example, the microprocessor 102 is electrically coupled to the sensors 30b, 35b, 40b through the connectors 230, 235, 240. The transceiver transmits and receives signals wirelessly. Alternatively, the transceiver does not need to be wireless.

Figure 3B:
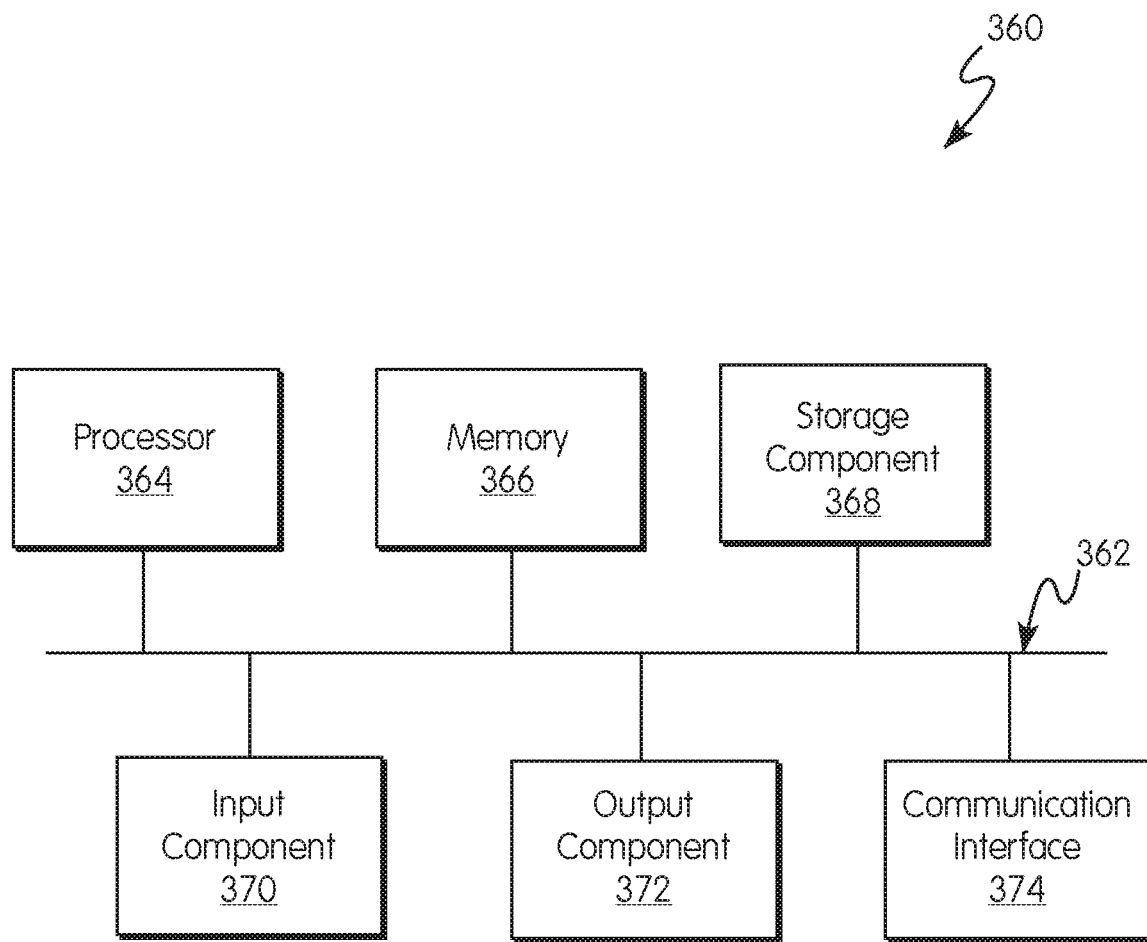
FIG. 3B is a diagram of a non-limiting embodiment of components of one or more devices of the present invention.

FIG. 3B is a diagram of example components of a device 360. Device 360 may correspond to one or more devices of Patient Incontinence Monitoring System, one or more devices of a transmitter of at least FIGS. 2A, 7A, 8A and 9A, and/or one or more devices (e.g., one or more devices of a system of) of power supply 104, microprocessor 102, transceiver 106, memory 116, and input/output 120. In some non-limiting embodiments, one or more devices of Patient Incontinence Monitoring System, one or more devices of a patient incontinence monitoring database, and/or one or more devices (e.g., one or more devices of a system) of transmitters of at least FIGS. 2A, 7A, 8A and 9A may include at least one device 360 and/or at least one component of device 360. As shown in FIG. 3B, device 360 may include bus 362, processor 364, memory 366, storage component 368, input component 370, output component 372, and communication interface 374.

Bus 362 may include a component that permits communication among the components of device 360. In some non-limiting embodiments, processor 364 may be implemented in hardware, firmware, or a combination of hardware and software. For example, processor 364 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 366 may include a random access memory (RAM), a read only memory (ROM), and/or another type of dynamic or static storage device (e.g., flash memory, magnetic memory, optical memory, etc.) that stores information and/or instructions for use by processor 364.

Storage component 368 may store information and/or software related to the operation and use of device 360. For example, storage component 368 may include a hard disc (e.g., a magnetic disc, an optical disc, a magneto-optic disc, a solid state disc, etc.), a compact disc (CD), a digital versatile disc (DVD), a floppy disc, a cartridge, a magnetic tape, and/or another type of computer-readable medium, along with a corresponding drive.

Input component 370 may include a component that permits device 360 to receive information, such as via user input (e.g., a touch screen display, a keyboard, a keypad, a mouse, a button, a switch, a microphone, etc.). Additionally, or alternatively, input component 370 may include a sensor for sensing information (e.g., a global positioning system (GPS) component, an accelerometer, a gyroscope, an actuator, etc.). Output component 372 may include a component that provides output information from device 360 (e.g., a display, a speaker, one or more light-emitting diodes (LEDs), etc.).

Communication interface 374 may include a transceiver-like component (e.g., a transceiver, a separate receiver and transmitter, etc.) that enables device 360 to communicate with other devices, such as via a wired connection, a wireless connection, or a combination of wired and wireless connections. Communication interface 374 may permit device 360 to receive information from another device and/or provide information to another device. For example, communication interface 374 may include an Ethernet interface, an optical interface, a coaxial interface, an infrared interface, a radio frequency (RF) interface, a universal serial bus (USB) interface, a Wi-Fi interface, a cellular network interface, and/or the like.

Device 360 may perform one or more processes described herein. Device 360 may perform these processes based on processor 364 executing software instructions stored by a computer-readable medium, such as memory 366 and/or storage component 368. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 366 and/or storage component 368 from another computer-readable medium or from another device via communication interface 374. When executed, software instructions stored in memory 366 and/or storage component 368 may cause processor 364 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 3B are provided as an example. In some non-limiting embodiments, device 360 may include additional components, fewer components, different components, or differently arranged components than those shown in FIG. 3B. Additionally, or alternatively, a set of components (e.g., one or more components) of device 360 may perform one or more functions described as being performed by another set of components of device 360.

Figure 4:
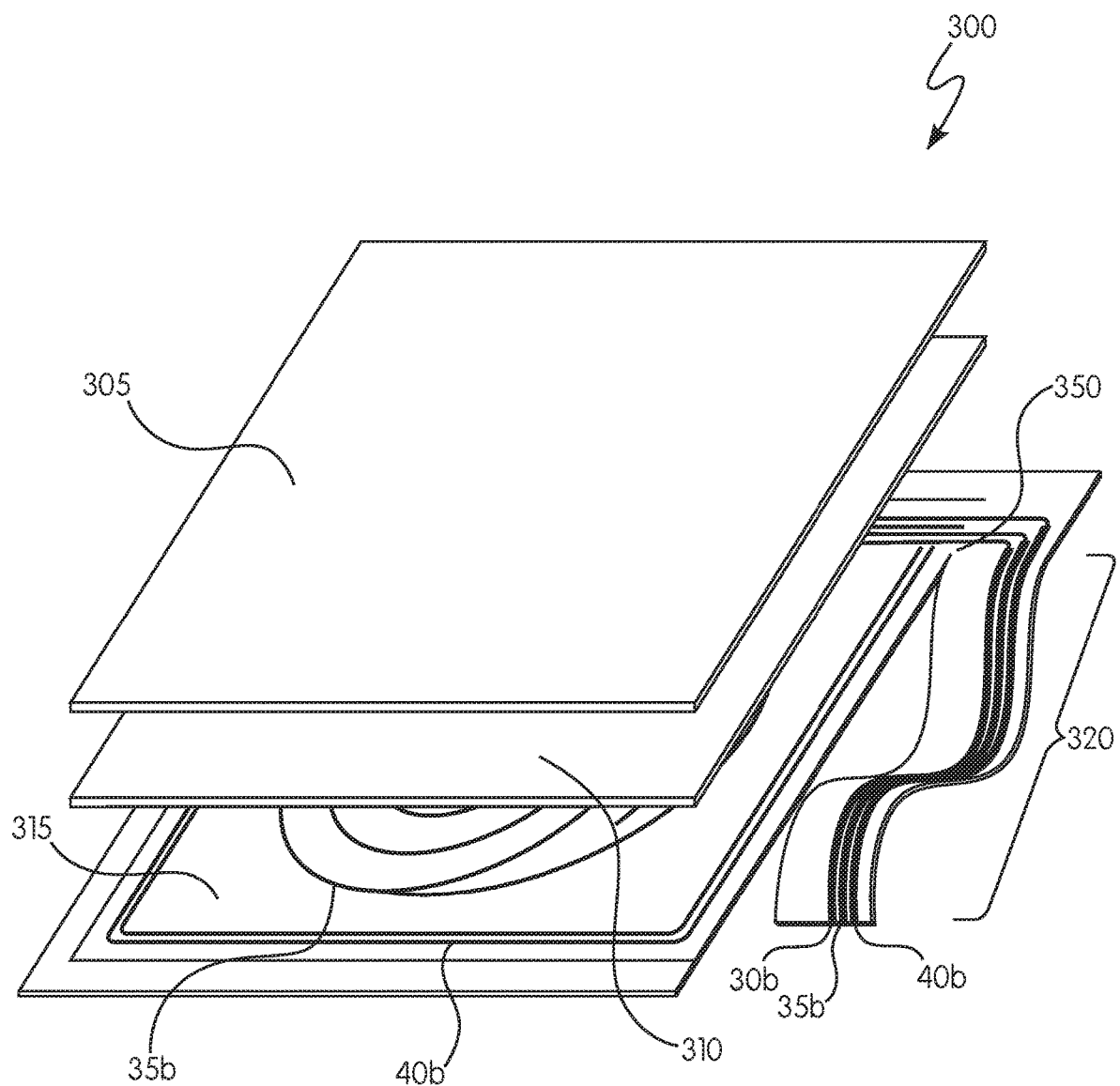
FIG. 4 is an exploded view of the sensor pad formed of three absorbent layers in accordance with an embodiment of the present invention.

With reference to FIG. 4, the sensor pad includes a top layer 305, an absorption layer 310, and an integrated sensor layer 315. A thin topcoat on the top layer absorbs fluid quickly and has other features, such as doesn't stick to wounds easily. The top layer 305, the first layer of the pad 10, acts as a cover and is made of a flexible material.

Top layer 305 can act as a distribution layer that wicks fluid across a wider area to spread it out. Adjacent is an absorption layer 310 that ensures complete absorption and is also made of a flexible material. This absorbent core is where the fluid is ultimately stored. This layer may include a powder held between layers of absorbent fiber, and this powder forms into a gel as it absorbs fluid. The gel will not release the fluid under pressure, keeping the patient drier.

The integrated sensor layer 315 has one or more multiple integrated sensors, 30b, 35b, 40b that form a circuit and are connected to the tail. Layer 315 is a waterproof layer. In one embodiment, it is formed of polypropylene onto which sensor ink is printed. Each of sensors 30b, 35b, 40b forms a separate circuit. The transmitter is operative to send electricity through the sensors. The one or more multiple integrated sensors 30b, 35b, 40b are positioned on the integrated sensor layer 315 at a specific location. The last layer is a strengthening layer, providing a final layer applied that dramatically increases the tensile strength of the pad, especially once the other layers are wet. It also has a finish that increases the friction against a bed sheet, helping to stay flat on the bed and resist wrinkling/wadding up.

Figure 5:
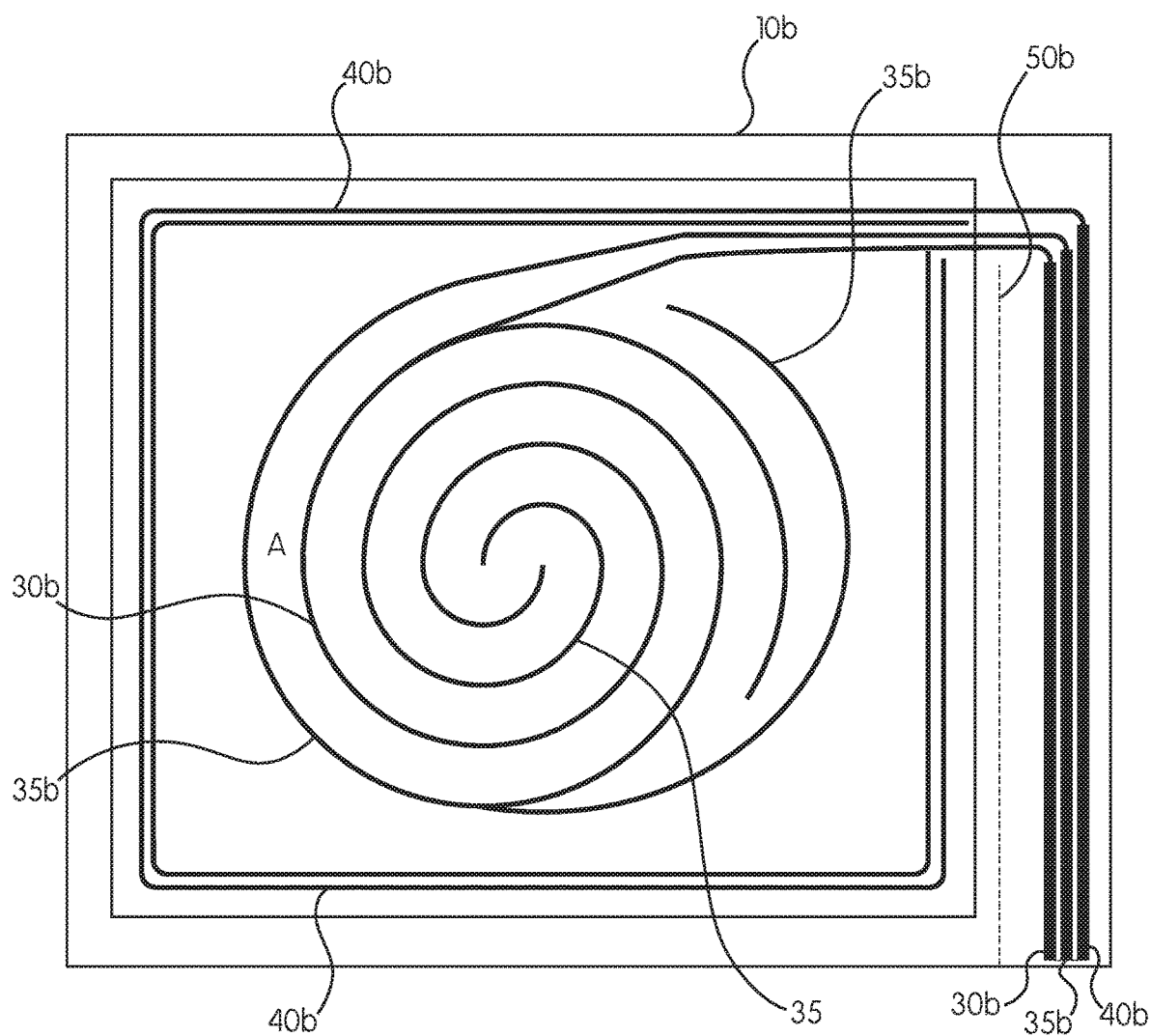
FIG. 5 is an elevation view of a sensor pad in accordance with an embodiment of the present invention.

With reference to FIG. 5, the numbered sensors are arranged in a predetermined fashion to ensure fast recognition of moisture on the pad. For example, the one or more sensors are laid out on the integrated sensor layer 315 in a circular fashion and the distance between the sensors may be 2.1 inches. This circular layout begins at the lower right end of the integrated sensor layer 315 where the sensors begin to go upward to the integrated sensor layer 315 and then wrap to the left. The right sensor 40b goes outward and around the outer edge of the integrated sensor layer 315. The left and middle sensors, 30b and 35b, go outward and curve in a circular fashion into the center of the integrated sensor layer 315, as shown in FIG. 5. The sensors form an interior central detection zone and a perimeter zone. The one or more sensors can alternatively be laid out on the integrated sensor layer 315 in a different layout, i.e., in a rectangular fashion. In other embodiments, the transmitter can be modified to handle a pad sensor with other numbers of sensors, such as four or more.

The beginning of the sensors 30b, 35b, 40b shown in FIG. 5 occurs on one edge of the integrated sensor layer 315. In an embodiment, the edge of the integrated sensor layer 315 is perforated along one edge so that it can be ripped off from the body of the pad 10a. This perforated edge with sensors 30b, 35b, 40b defines a tail end of the integrated sensor layer 315.

With continuing reference to FIG. 5, the middle sensor 35b is energized with a ground signal, such that when moisture is present on the integrated sensor layer 315, a circuit is formed and the tail end forms a coupling with the connectors of the transmitter. The transmitter operates to recognize characteristics of the electric signals in the circuits formed in the sensor pad 10a.

In an exemplary embodiment, each of the layers of the multi-layer location-based sensor pad 10a may be made of an absorbent material. The sensor pad 10a may be placed on a flat surface (e.g., a patient bed, a patient chair) and may also be placed on surfaces not flat, where the pad can take the shape of the surface. The pad can also be wrapped around a patient's body or configured to provide sufficient coverage for incontinence detection. The sensor pad 10a may be placed inside a wearable unit and may take the shape of the wearable unit. In one exemplary embodiment, a sensor and/or sensor pad 10a may be attached to an interior of a garment. For example, a sensor may be attached to an interior of a garment such as, for example, briefs, diapers, pull-ups, or other wearable garments. In such embodiments, a sensor may be printed directly into a wearable garment with a tail coming out of a portion of the garment to facilitate the attachment with a transmitter.

As shown in FIG. 5, the layout pattern of the one or more sensors is used to determine where the moisture is present on the integrated sensor 40b. In an embodiment, if moisture is detected between 35b and 40b, at location A, a circuit will be formed there determining that the moisture is present. In another embodiment, the transmitter determines the capacitance of the completed circuits including the sensors. In another example, the transmitter can read another physical property (such as inductance, temperature, and impedance). The transmitter may use the physical property of the particular sensors to determine the characteristics of the detected moisture (e.g., density, location, type). As an example, the sensor 35b transmits a ground current and the other sensors are always on and have an electrical current. When moisture touches the other sensors (e.g., 30b and 40b), the physical properties of the sensors will change, the smart transmitter will determine the change (e.g., drop in impedance), and collect the moisture information. This moisture information may include the characteristics of the detected moisture.

In one non-limiting embodiment, the multi-layer location-based sensor can be used to detect the presence of moisture according to the transmitter detection of a change in physical property from the presence of moisture and the completion of the circuit on the sensor. The moisture is detected when it absorbs down through each of the layers of the pad onto the sensor. As an example, if moisture is applied to the top right portion of the top layer 305, it may be absorbed through the top layer 305 and down into the top right portion of the absorption layer 310. The moisture may then be absorbed through the top right portion of the absorption layer 310 and into the top right portion of the integrated sensor layer 315 (e.g., onto the sensors in the top right portion 35b, 40b). The sensors 35b, 40b in the top right portion will indicate moisture on the integrated sensor layer 315, which may then correspond to the tail end. The smart transmitter may determine from the tail end the presence of moisture related to the sensors in the top right portion (e.g., 35b, 40b).

With continuing reference to FIG. 5, the connectors 230, 235, 240 have conductive pins that are inserted into the sensors 30b, 35b, 40b of the tail portion of the sensor pad 10a. The tail 15a is created by separating the tail 15a from the sensor pad body along line 50a. By pulling the sections apart, the tail 15a is liberated from the sensor pad body and free to move in a more flexible manner.

Figure 6:
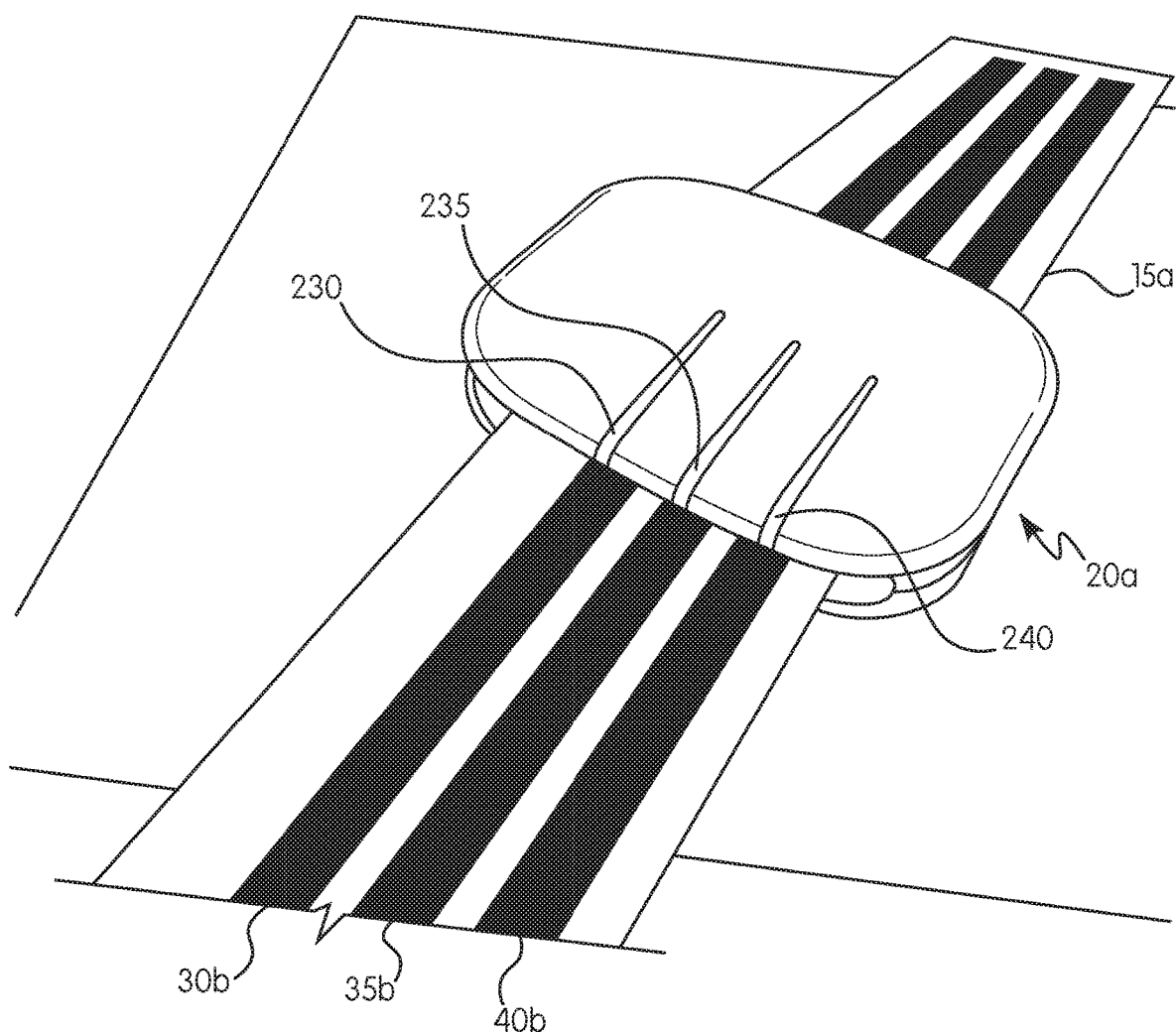
FIG. 6 is a perspective view of a pad sensor coupled to a transmitter in accordance with an embodiment of the present invention.

With reference to FIG. 6, the smart transmitter 20a is clamped onto the tail 15a so that the tail 15a can pass through the cavity 205 and provide aligning physical connectivity for the connectors 230, 235, 240, with the sensors 30b, 35b, 40b, on the tail 15a. In FIG. 6, the tail portion 320 is shown partially separated from the sensor pad body, with a partial connection formed, after the partial detachment or separation of the tail 15a, forming a small bridge connection 350 which holds the sensors 30b, 35b, 40b in place while the pad is being used. This bridge connection can be torn when the pad is removed. When the pad is being replaced, the tail 15a can be completely separated by pulling the tail 15a from the body, separating and disconnecting the sensors that are bridged across that line. This tail portion 320 provides flexibility for replacement, because the dirty pad can quickly and easily be dispelled. Also, the perforation can have alternative configurations, for example, one of skill in the art could envision a perforated line extending only halfway, where the tail does not pull off, but stays attached. When changing, instead of pulling the tail off and disposing of the pad, the tail would first be removed from the transmitter and then the entire sensor pad, both body and tail, could be disposed together. The connectors 230, 235, 240 on the transmitter 20a provide the connection to the sensors 30b, 35b, 40b on the tail 15a. The smart transmitter may also include a T-connector 245, which may be perpendicularly connected to connector 235 and lined up with sensor 35b. The connectors are electrically coupled individually to the sensors such that moisture information may be transmitted from the sensors to the connectors. The connectors 230, 235, 240, 245 made of a conductive material are electrically coupled together in multiple ways including the receiver sticking into the sensors, the receiver going up against the sensor, or any combination thereof. In an embodiment, the connectors 230, 235, 240 have conductive pins that are inserted into the sensors 30b, 35b, 40b to create the electrical connection. Through use of the connection, the smart transmitter 20a receives the moisture information from the sensors 30b, 35b, 40b to determine when and where the moisture is present on the integrated sensor layer 315.

The microprocessor 102 controls the current and/or voltage to a sensor. The microprocessor 102 provides voltage across the sensors to determine if a circuit is present as a result of the presence of moisture. The initial physical property of the sensors is determined and stored and then when moisture is present, the physical property will change and alert the microprocessor 102, which will gather the sensor information. For example, the resting sensors have a certain physical property or capacitance. Thus, when moisture is present, the circuit is completed and the capacitance changes, which the transmitter 20a will detect and record.

The microprocessor 102 processes instructions on the memory, including an algorithm, for determining the original physical property of a sensor and storing the physical properties in memory. The microprocessor 102 is always on, but could be programmed to use a clock cycle, for example, a clock placed on the board and coupled to the microprocessor, configured to wake up in response to receiving a notification from the sensor layer that moisture is present. The transmitter receives the moisture information and can process received information to manipulate and modify it (e.g., analyze, categorize, calculate, convert). The microprocessor 102 may store the moisture information and modify it over time. The microprocessor 102 can be connected to a radio in the smart transmitter 20a such that the transceiver 106 receives the modified information from the microprocessor 102 and may send the information to a processing device 25a. The messages can be sent wirelessly.

The transceiver 106 sends signals or messages to a network, a computer, other transmitters, or any other device configured to receive and operate on the transmitted signals. The signals are sent in messages and can communicate information about the pad and patient using the pad. Zigbee, Bluetooth, or proprietary formulation may be used for communication. The transmitter sends data when the status of the pad changes (dry to wet, disconnected, etc.) as well as a 'heartbeat' so that we know it's still on the network. The information can include that the pad 10a is wet, where on the pad is wet, or the saturation level, and information about the location, and the name of the patient associated with a particular pad. The network can modify the information. The third-party device 25a can use the signals or messages and can display them so that a user can react to them. Continence data includes information about the patient's toileting, consisting of urine levels, fluid and diet nutrition levels during time periods, time that the resident passes urine, type and volume of drinks, degree of wetness, number of pad changes, length of time exposed to soiled environment, number of clothing and/or bedding changes, medical circumstances, type of bowel movement, time of bowel movement, day of bowel movement, Bristol stool scale classification, constipation data, whether a catheter is in place, and risk of fall while attempting to toilet.

As an example, a care facility employee will place pad 10a on top of a bed with the tail end hanging off. The care facility employee will then take a transmitter 20a and attach it to the tail end, such that it is securely fastened to the tail end and electrically coupled to the sensors on the tail 15a. The transmitter 20a will be turned on such that the middle sensor will be on and supplying the pad 10a with power. Once the pad 10a is saturated, the transmitter 20a will read the pad 10a, send the signals to the network which will send the signals to a third-party device 25a, alerting a care facility employee to come and change the sheet. The transmitter 20a and the connected tail end can be ripped off of the pad 10a by using the perforation such that the transmitter 20a and tail end are preserved. Further, the sheet and pad can easily be cleaned.

Figure 7A:
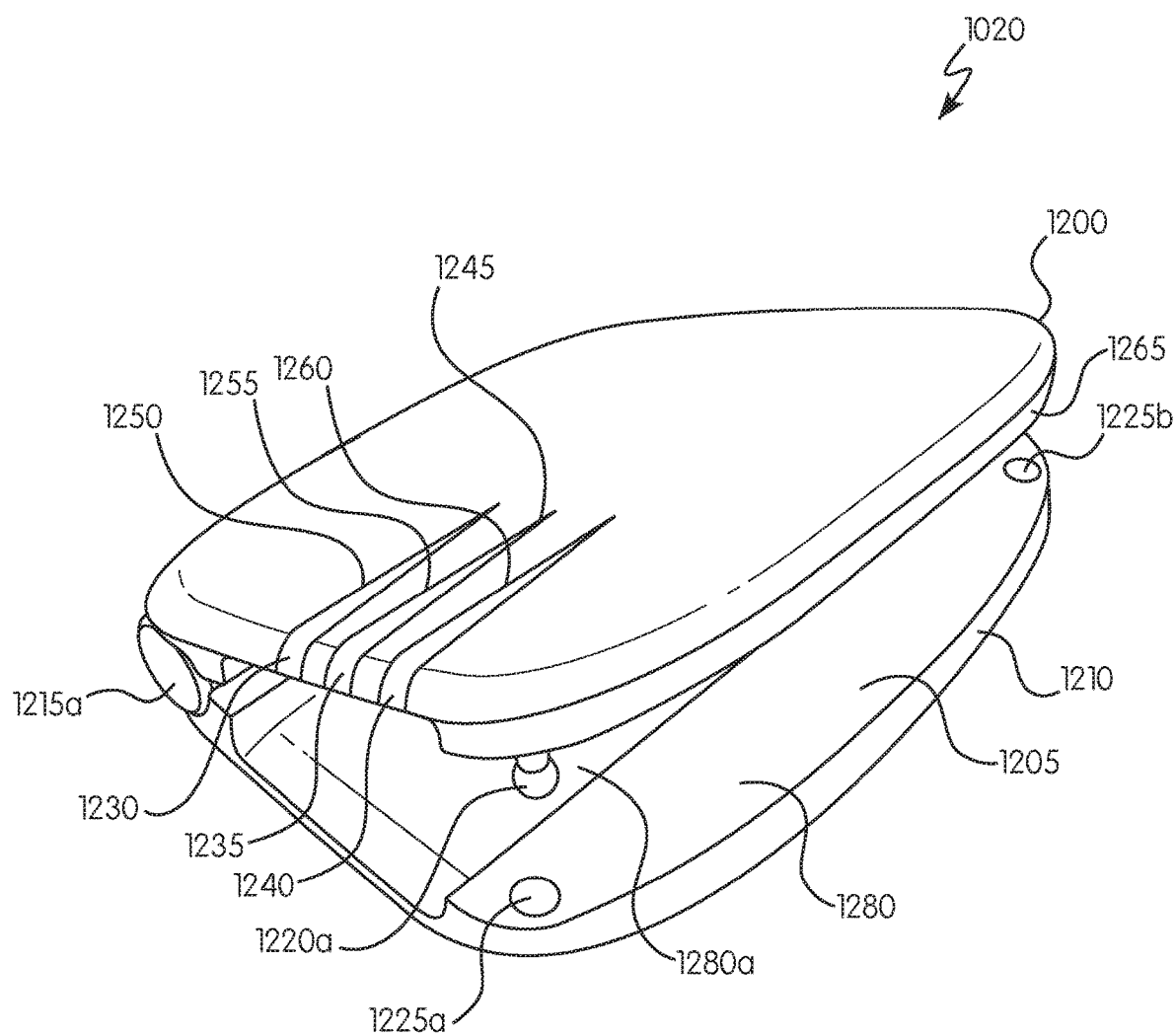
FIG. 7A is a perspective view of a transmitter in an open position in accordance with another embodiment of the present invention.

With reference to FIG. 7A, the transmitter 1020 has a top panel 1200 and a bottom panel 1210 that are connectably secured together from the side by a movable connecting piece 1215a, 1215b forming a clamshell with congruent joints on either end. The movable connecting pieces 1215a, 1215b form an axis of rotation about the joint, where the panels can move about the axis, to open and close, by rotating the panels 1200 and 1210, relative to each other. An internally curved inside surface is formed, such that when the pieces are closed together a cavity 1205 is formed. The internally curved insides are stepped internally down such that an inner portion 1280 is thinner than the outer portion. Extending outward from the top panel 1200 is a male connector 1220a on one side and male connector 1220b on the other side. Extending outward from bottom panel 1210, and directly opposite the male connectors of top panel 1200, are female openings 1225a, 1225b. The male connectors 1220a, 1220b form a locking connection between the panels 1200, 1210 when they are inserted into the mating female openings 1225a, 1225b and received therein. However, one of ordinary skill in the art would recognize that locking surfaces can be formed with other means, where the transmitter may be closed and secured.

Figure 7B:
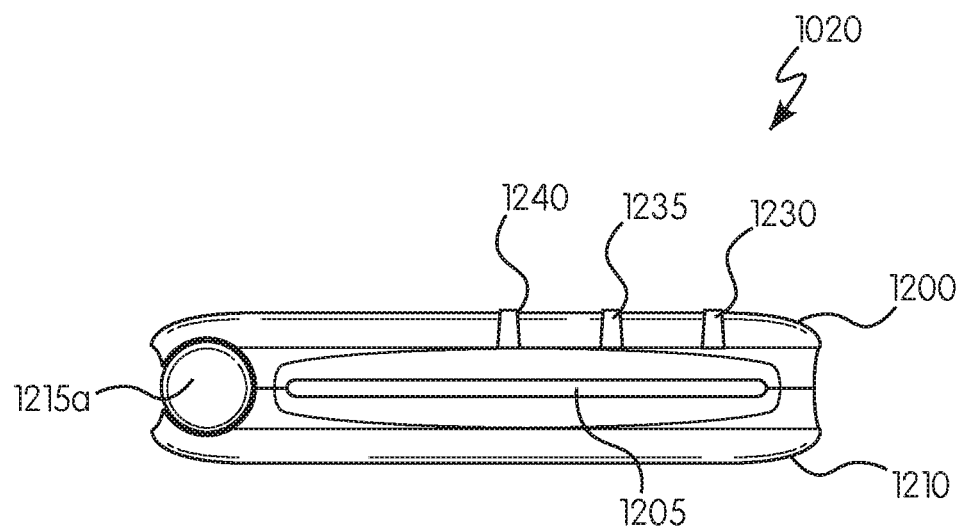
FIG. 7B is a side elevation view of the transmitter in a closed position in accordance with another embodiment of the present invention.
Figure 7C:
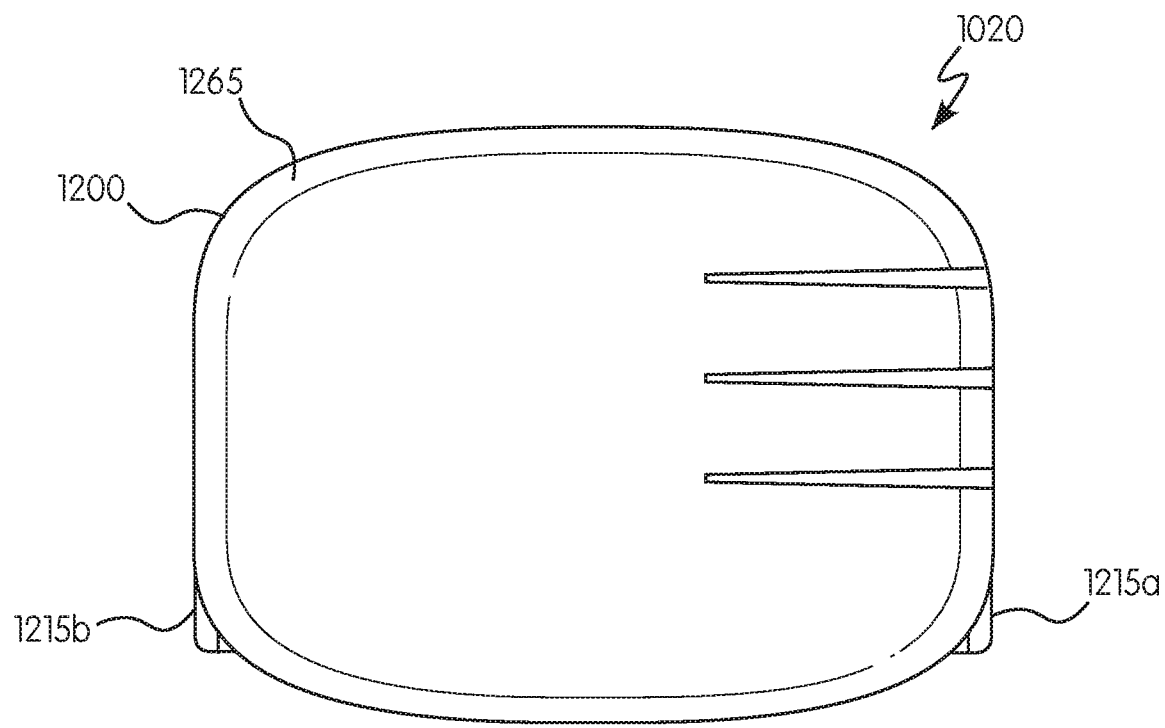
FIG. 7C is a top elevation view of the transmitter in accordance with another embodiment of the present invention.

With reference to FIGS. 7B and 7C, the transmitter 1020 of FIG. 7A is shown from various angles. With reference to FIG. 7B, the transmitter 1020, when closed, is secured by inserting male connectors 1220a, 1220b into the female connectors 1225a, 1225b, respectively. The closing of the transmitter 1020 will define cavity 1205 through the closed transmitter 20a. The cavity 1205 provides an opening for the tail, that is to be inserted, or has already been inserted, into the transmitter 1020 and coupled to the transmitter 1020. With reference to FIG. 7C, the transmitter 1020 is shown from the top with the curved edges of the top panel 1200 rounded to prevent unintended contact or puncture of the sensor material. The rounded surfaces are also adapted to fit into a caregivers hand and facilitate quickly opening and closing. In one embodiment, the transmitter can have a locking mechanism as shown. In addition, the connector can be adapted to lock and open by closing and pressing to lock, or pressing to unlock and open.

FIGS. 8A-9C illustrate other exemplary embodiments of transmitters of the present disclosure. The embodiment illustrated in FIGS. 8A-8C includes similar components to the embodiment illustrated in FIGS. 2A-2G, and the similar components are denoted by a reference number followed by the letter A. The embodiment illustrated in FIGS. 9A-9C includes similar components to the embodiment illustrated in FIGS. 2A-2G, and the similar components are denoted by a reference number followed by the letter B. For the sake of brevity, these similar components and the similar steps of using transmitter 20A (FIGS. 8A-8C) and transmitter 20B (FIGS. 9A-9C) will not all be discussed in conjunction with the embodiments illustrated in FIGS. 8A-8C and FIGS. 9A-9C.

Referring to FIG. 8A, in one exemplary embodiment, a transmitter 20A generally includes a printed circuit board, a power supply enclosed in a plastic shell having a top portion 200A and a bottom portion 210A, a movable connecting piece 400, e.g., a side hinge, and pins 402 attached to the printed circuit board. In one exemplary embodiment, the transmitter 20A includes four pins 402. In other exemplary embodiments, other number of pins 402 may be utilized. In one embodiment, the pins 402 extend through the casing to form the connection points to both power and receive a signal from the sensor. Although in FIG. 8A the pins 402 appear to have a flat head, it is contemplated that the heads of the pins 402 have teeth. For example, in one embodiment, these pins 402 are crowned, e.g., the heads of the pins 402 have teeth allowing them to reliably penetrate through a top layer of non-woven textile on the tail and penetrate into the sensor ink. The plastic casing is spring hinged on one side of the transmitter 20A allowing it be operated with one hand to easily close around the tail element of the pad. The bottom portion 210A of the transmitter 20A includes a rubber backing 404 applied to it for the pins 402 to lightly sink into.

Figure 8B:
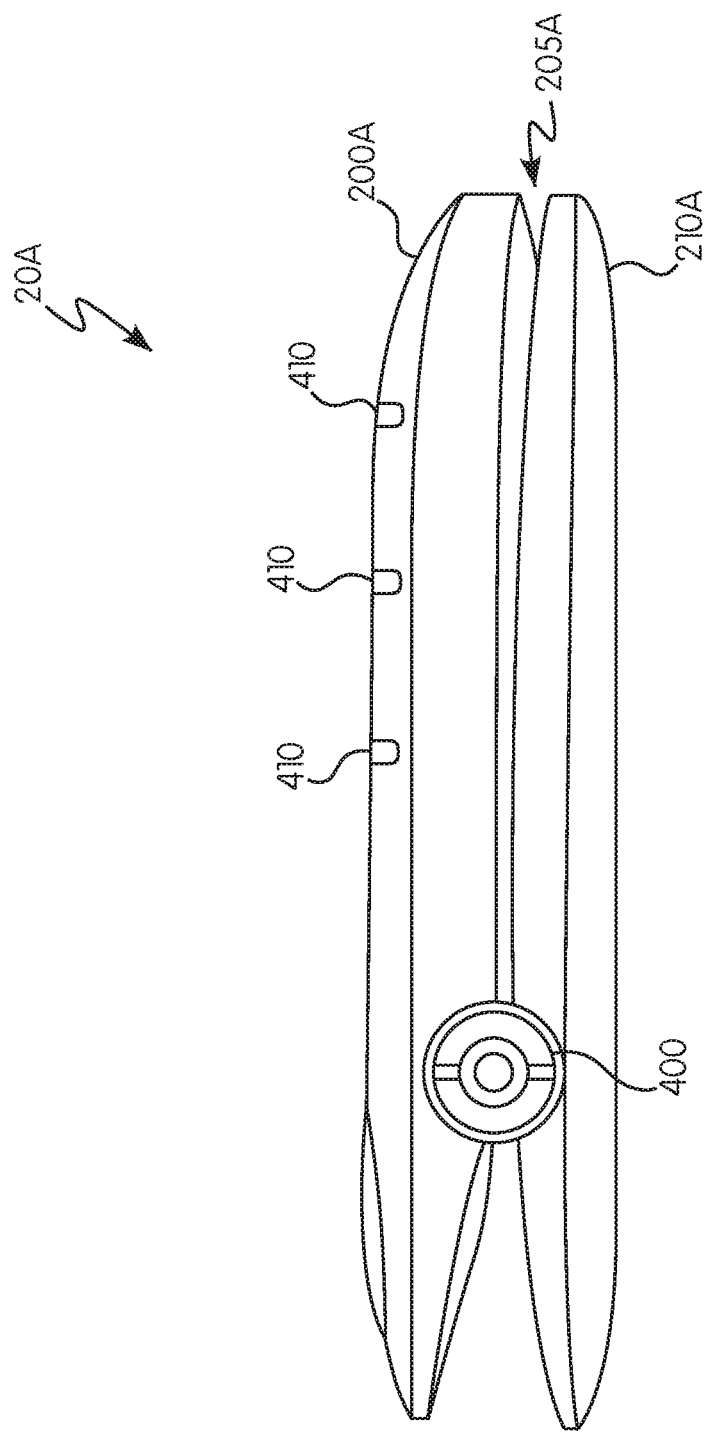
FIG. 8B is a side elevation view of the transmitter in a closed position in accordance with another embodiment of the present invention.
Figure 8C:
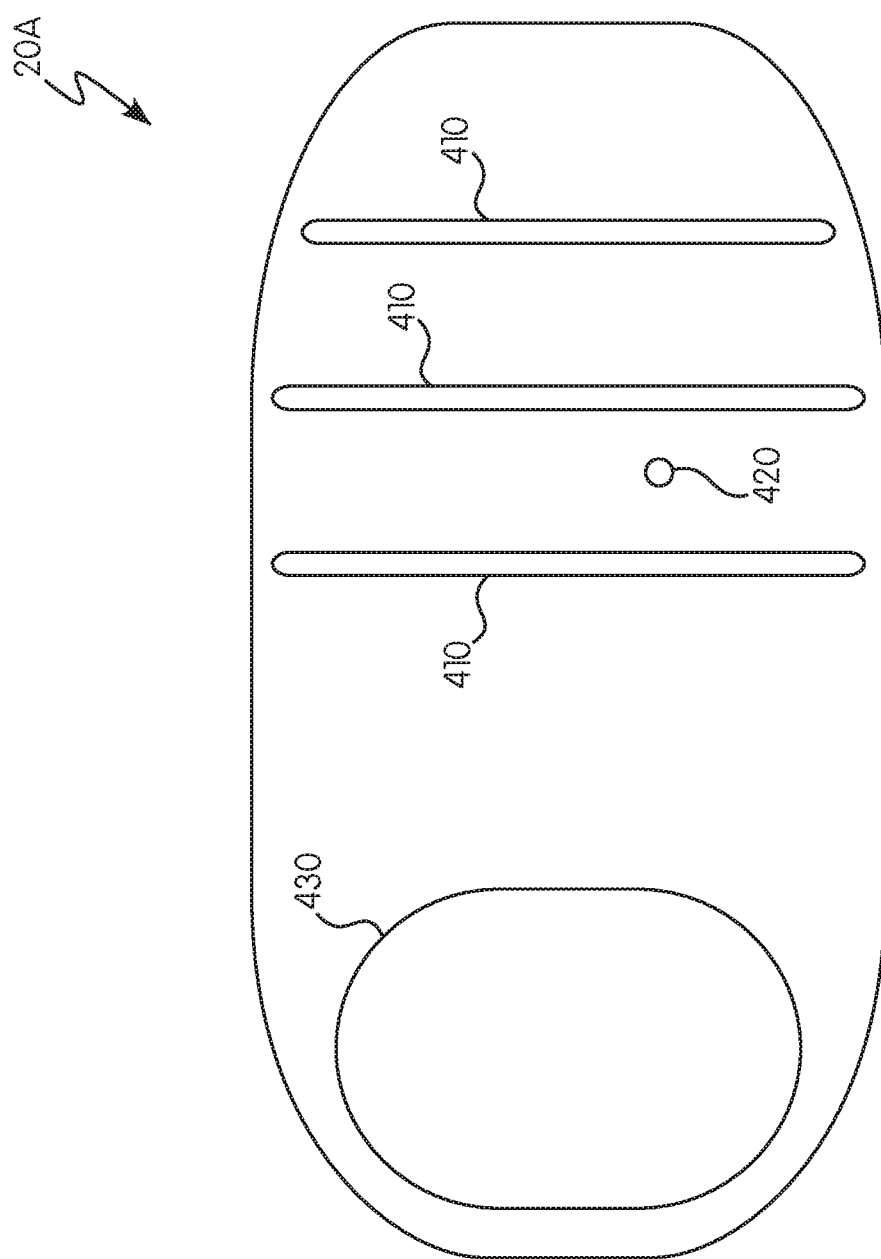
FIG. 8C is a top elevation view of the transmitter in accordance with another embodiment of the present invention.

Referring to FIG. 8B, in one exemplary embodiment, the transmitter 20A is shown from a side to illustrate a portion of guide lines 410 to be used to line up with the sensor trances. Referring to FIG. 8C, in one exemplary embodiment, the transmitter 20A is shown from the top to illustrate the guide lines 410. The transmitter 20A also includes an indicator LED 420 and a rubberized grip pad 430 for easier operation of the spring hinge.

Figure 9A:
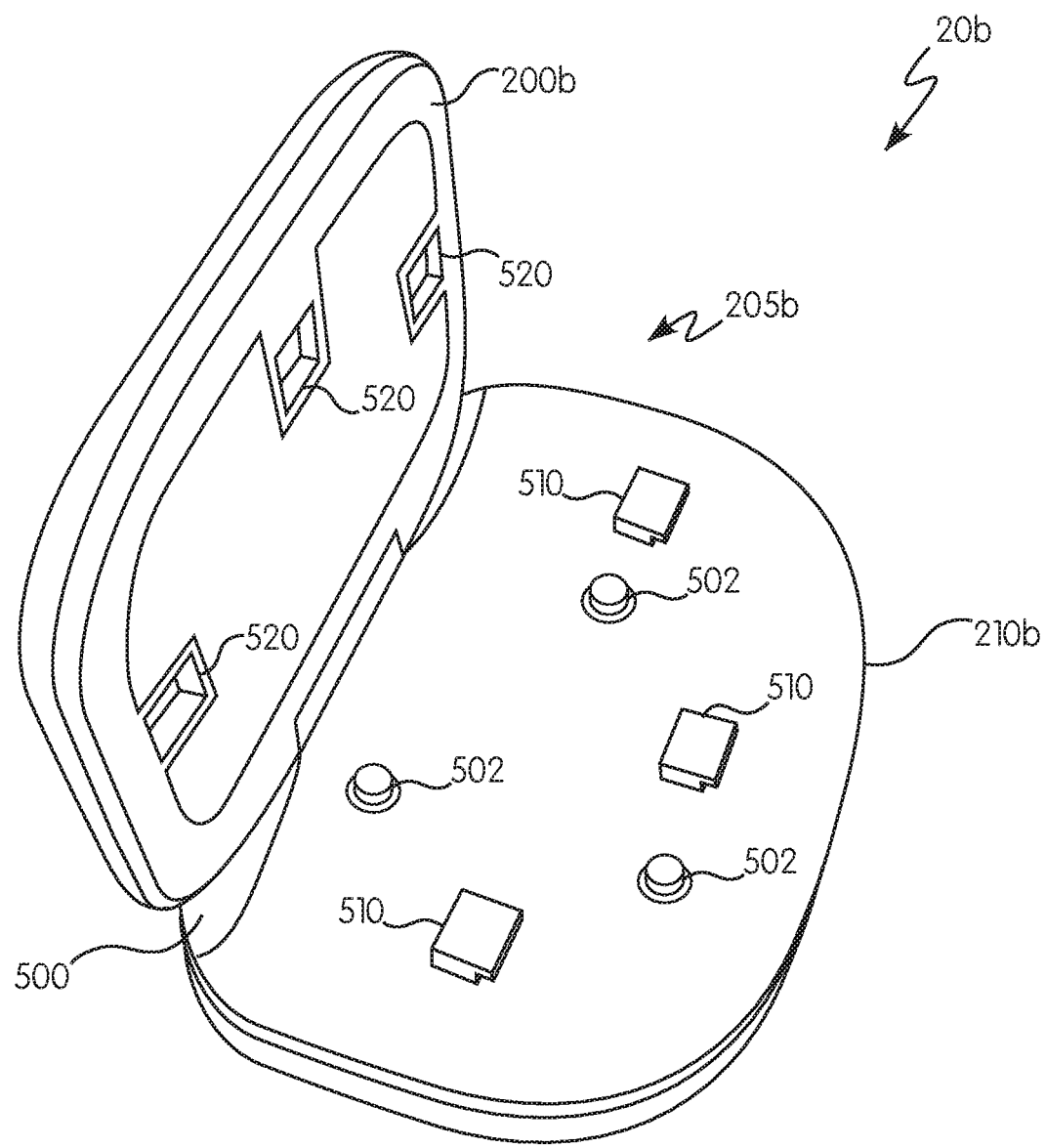
FIG. 9A is a perspective view of a transmitter in an open position in accordance with another embodiment of the present invention.

Referring to FIG. 9A, in one exemplary embodiment, a transmitter 20B includes pins 502 and functions generally the same as transmitter 20A but the movable connecting piece 500 that movably connects the top portion 200B and the bottom portion 210B is not spring tensioned. The movable connecting piece 500, a male connection clip portion 510, and a female connection clip portion 520 form a locking mechanism to keep the transmitter 20B affixed to a disposable garment. This locking mechanism is also tamper proof and requires a non-obvious application of directional force to release so that patients will not play with or inadvertently remove the transmitter 20B.

Figure 9C:
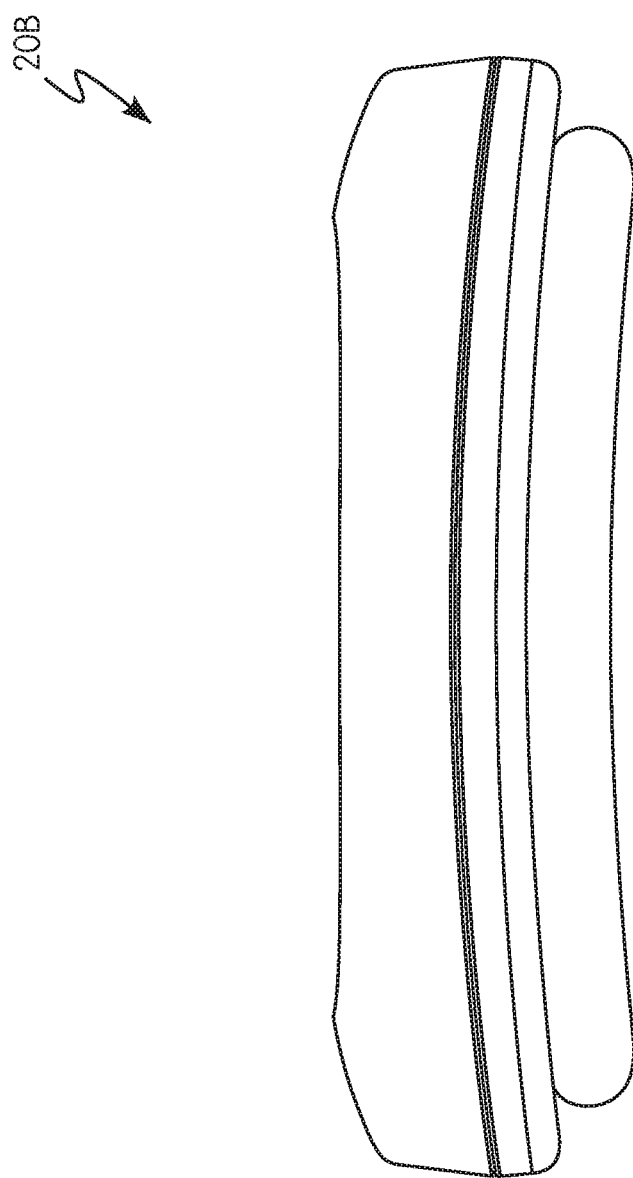
FIG. 9C is a side elevation view of the transmitter in accordance with another embodiment of the present invention.

Referring to FIG. 9B, in one exemplary embodiment, the transmitter 20B is shown from a front side to illustrate the guide lines 530 to attach to a sensor. In one embodiment, a brief only has two trace lines and is hit by three pins, e.g., two ground and an open. The transmitter 20B also includes an LED 540. Referring to FIG. 9C, in one exemplary embodiment, the transmitter 20B is shown from a bottom side to illustrate the transmitter 20B when it is closed or in a locked position with all the male clip portions 510 and female clip portions 520 connected.

Figure 10:
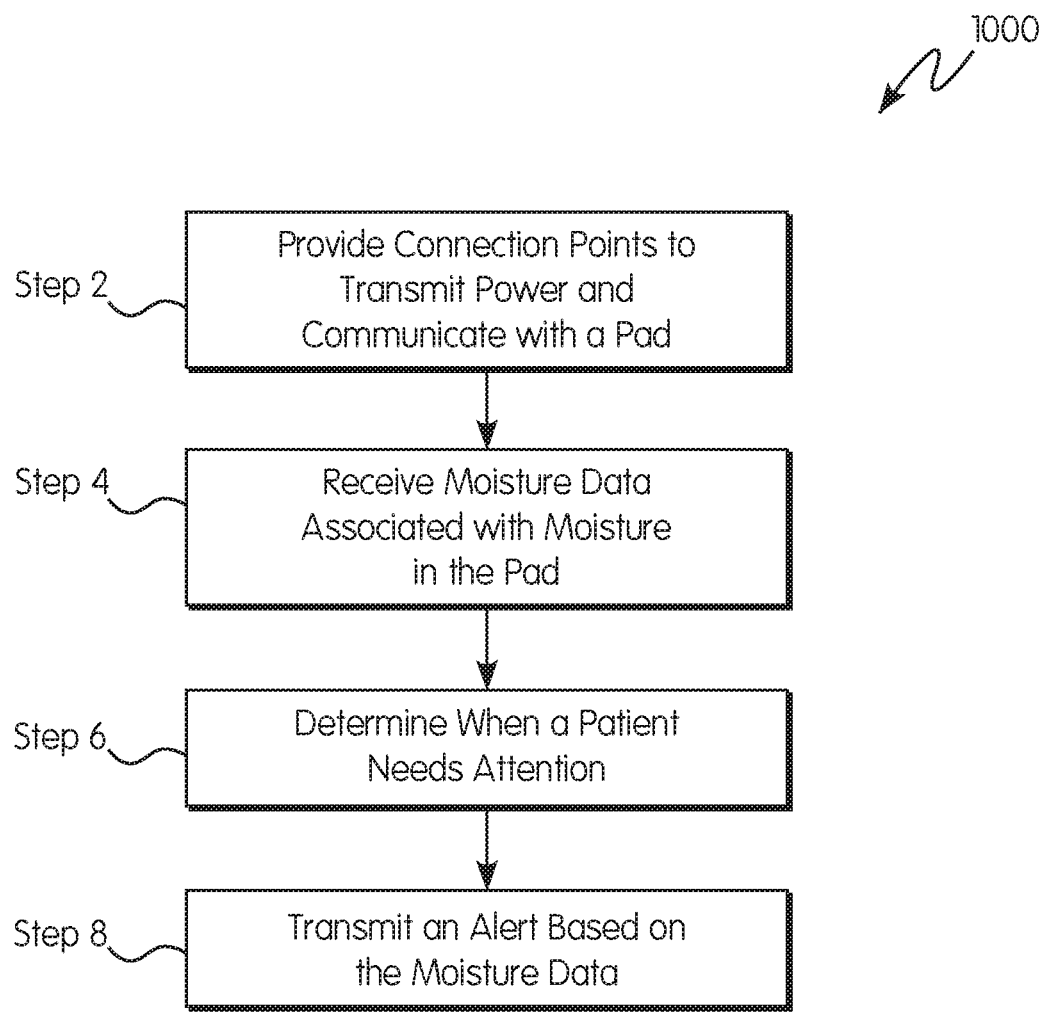
FIG. 10 is a flowchart of a non-limiting embodiment of a process for monitoring a patient.
Figure 11:
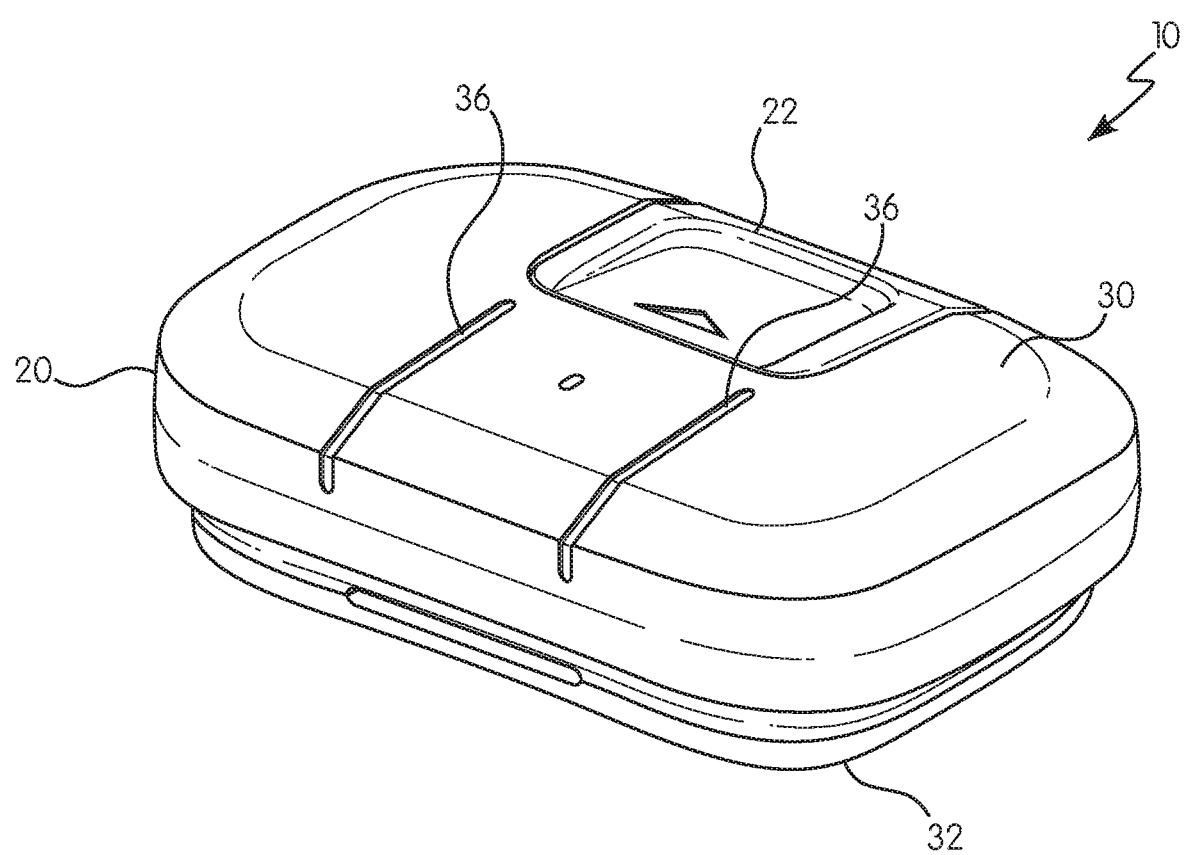
FIG. 11 is a perspective view of a monitoring device with a locking mechanism in a first position in accordance with an embodiment of the present invention.
Figure 12:
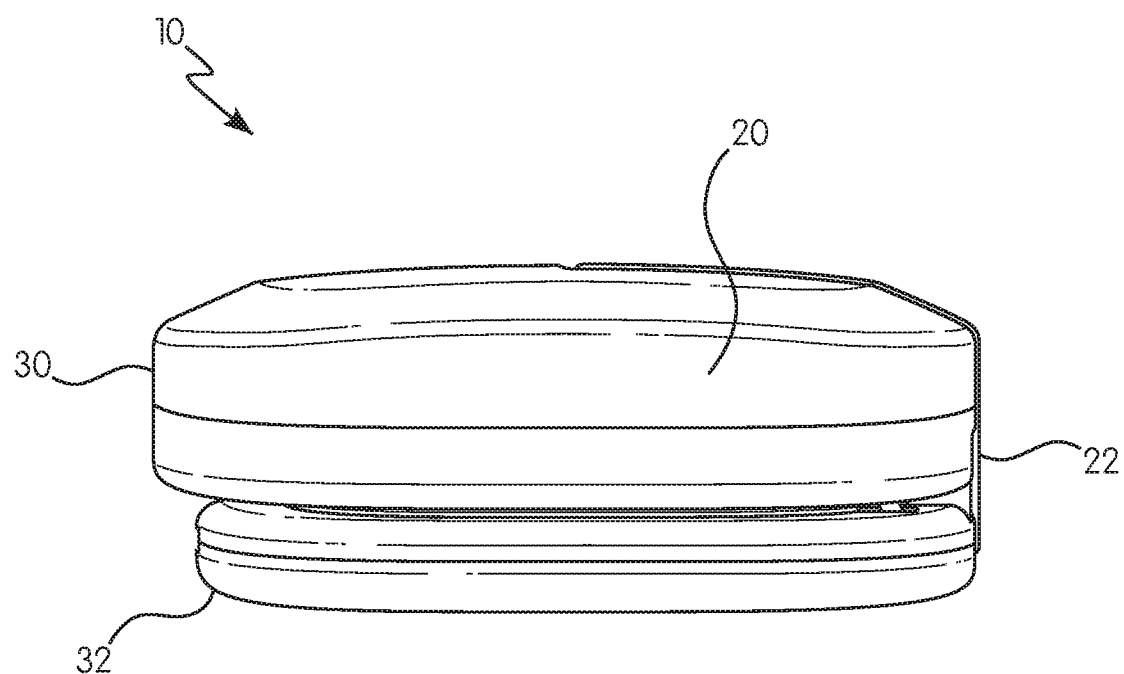
FIG. 12 is a side perspective view of a monitoring device with a locking mechanism in a first position in accordance with an embodiment of the present invention.

Referring to FIG. 10, in some non-limiting embodiments, a computer-implemented monitoring method 1000 includes steps for patient care used in a patient incontinence monitoring system. At step 2, the monitoring method 1000 includes providing connection points to transmit power and communicate with a pad. For example, monitoring method 1000 provides the connection points for transmitting power to a sensor pad and/or communicating based on one or more signals, sensor pad data (e.g., moisture data) associated with the sensor pad.

In some non-limiting embodiments, at step 4, the monitoring method 1000 includes receiving and/or transmitting moisture data associated with moisture in the pad. For example, moisture data may be transmitted or received from a transmitter, from a sensor pad, from a device coupled to the transmitter, or from a central computer system associated with the monitoring method, such as a patient monitoring system or other third party patient care systems.

In some non-limiting embodiments, at step 6, the monitoring method 1000 includes determining when a patient needs attention. For example, the monitoring system includes determining when a sensor pad associated with a patient has moisture. In some aspects, the monitoring method determines when a sensor pad associated with a patient meets a threshold of moisture in the pad.

In some non-limiting embodiments, at step 8, the monitoring method 1000 includes transmitting an alert based on the moisture data. For example, an alert may be transmitted to a patient care system for automatically updating a patient care worker that a patient needs a bed change. In some non-limiting embodiments, an alert may be based at least partially on data from a patient care system. In some non-limiting embodiments, the data from a patient care system may include historic data associated with a patient sensor pad.

The present disclosure is also directed to a monitoring device for detecting wetness in a garment. The monitoring device of the present disclosure includes a locking mechanism that slides back and forth, relative to a clip that is removably attachable to a garment between a first position in which the locking mechanism locks the clip in a closed position and a second position in which the clip is in an open position. As the locking mechanism transitions from the first position to the second position, the locking mechanism opens the clip. Advantageously, the monitoring device of the present disclosure allows a caregiver to align and secure the monitoring device to a garment using only one hand.

Figure 13:
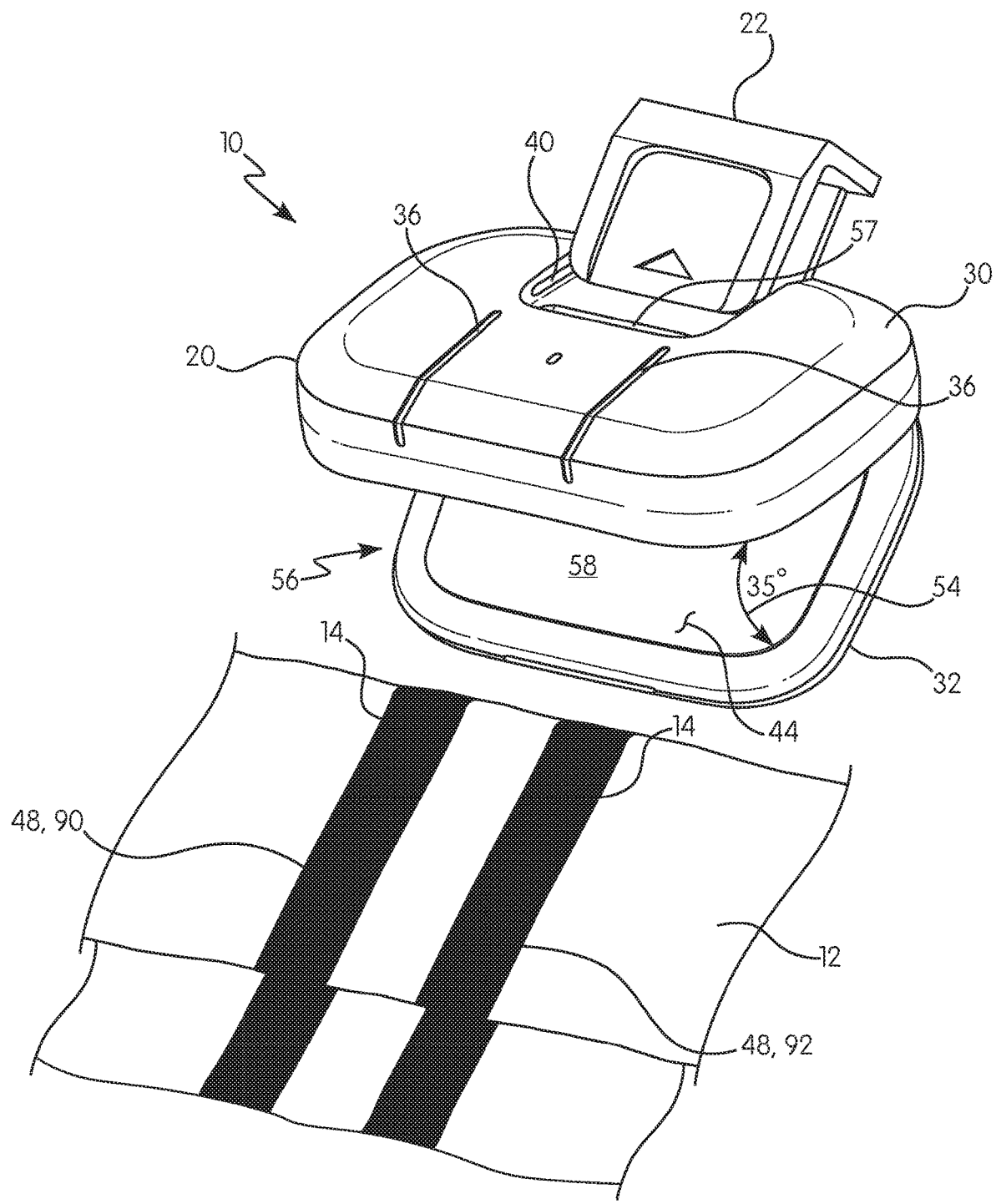
FIG. 13 is a perspective view of a monitoring device with a locking mechanism in a second position and the monitoring device aligned with a garment in accordance with an embodiment of the present invention.
Figure 17:
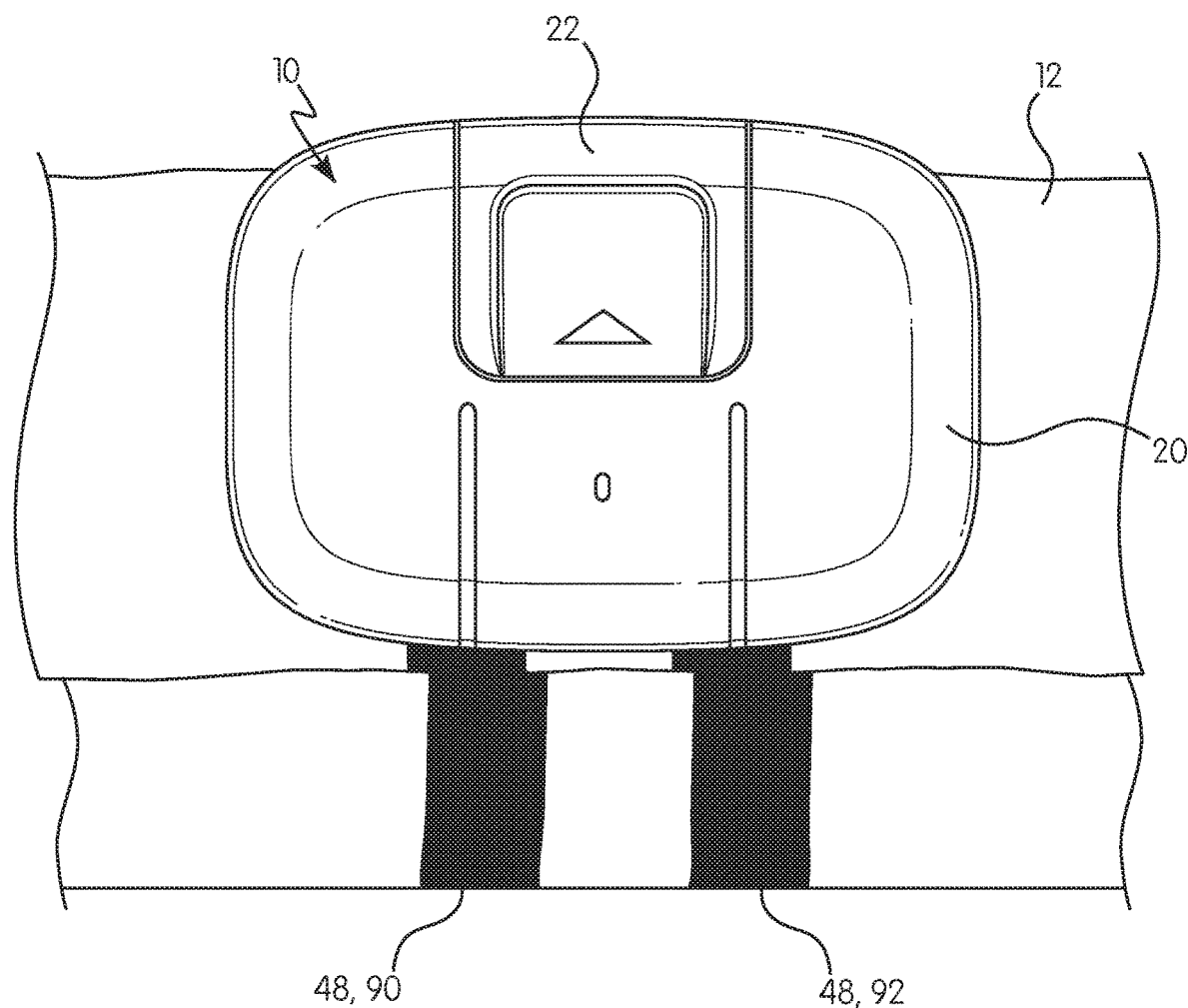
FIG. 17 is a perspective view of a monitoring device with a locking mechanism in a first position and the monitoring device attached to a garment in accordance with an embodiment of the present invention.
Figure 18:
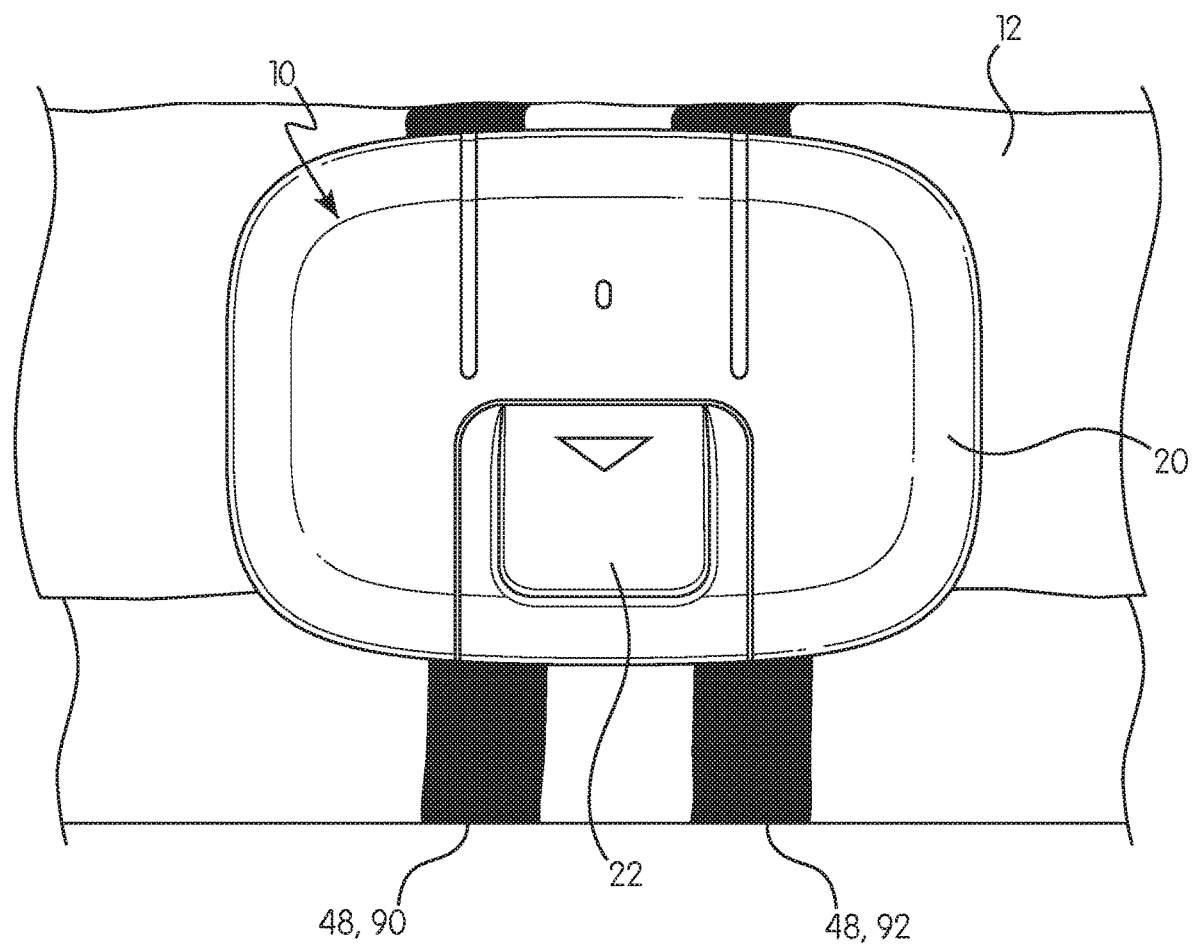
FIG. 18 is a perspective view of a monitoring device with a locking mechanism in a first position and the monitoring device attached to a garment in accordance with another embodiment of the present invention.

Referring to FIGS. 11-15, 19, and 20, in an exemplary embodiment, a monitoring device 10 (e.g., a monitoring assembly, a housing assembly, etc.) for detecting wetness in a garment 12 (FIGS. 13 and 16-18) includes a clip 20 and a locking mechanism 22 (e.g., a latch, switch, lock, etc.). The clip 20 and locking mechanism 22 provide a mechanism for removably attaching the monitoring device 10 to a garment 12 as shown in FIGS. 13, 17, and 18. The monitoring device 10 of the present disclosure is compatible with any type of under garment such as, for example, pads, briefs, diapers, pull-ups, or other wearable garments.

Referring to FIGS. 11-15, the locking mechanism 22 is movably connected to the clip 20. In an exemplary embodiment, the locking mechanism 22 is transitionable between a first position (c) in which the locking mechanism 22 locks the clip 20 in a closed position and a second position (FIGS. 13-15) in which the clip 20 is in an open position.

Referring to FIGS. 11-15, 19, and 20, in one exemplary embodiment, the clip 20 generally includes a top portion 30, a bottom portion 32, a hinge portion 33, a resilient member 34, guide lines 36, fasteners 38, rails 40 (FIG. 15), a link or first detent portion 42 (FIGS. 25 and 26), an elastomeric portion 44, a printed circuit board 46 including a transmitter 50 (e.g., circuit board, etc.), and pins 52. In some non-limiting embodiments, sensors 48 may be placed inside a wearable unit, e.g., the garment 12, and may take the shape of the wearable unit. For example, in one exemplary embodiment, a sensor 48 and/or sensor pad may be attached to an interior of a garment 12. In some non-limiting embodiments, sensors may also be included (e.g., extend into, etc.) as part of the monitoring device 10.

In some non-limiting embodiments, the top portion 30 and the bottom portion 32 of the clip 20 are transitionable between a closed position (FIGS. 11, 12, 17, and 18) in which the clip 20 is securely attached to a garment 12 (FIGS. 13, 17, and 18) and an open position (FIGS. 13-15) in which the top portion 30 is spaced away from the bottom portion 32. In the open position, an opening 56 is created between the top portion 30 and the bottom portion 32.

Figure 14:
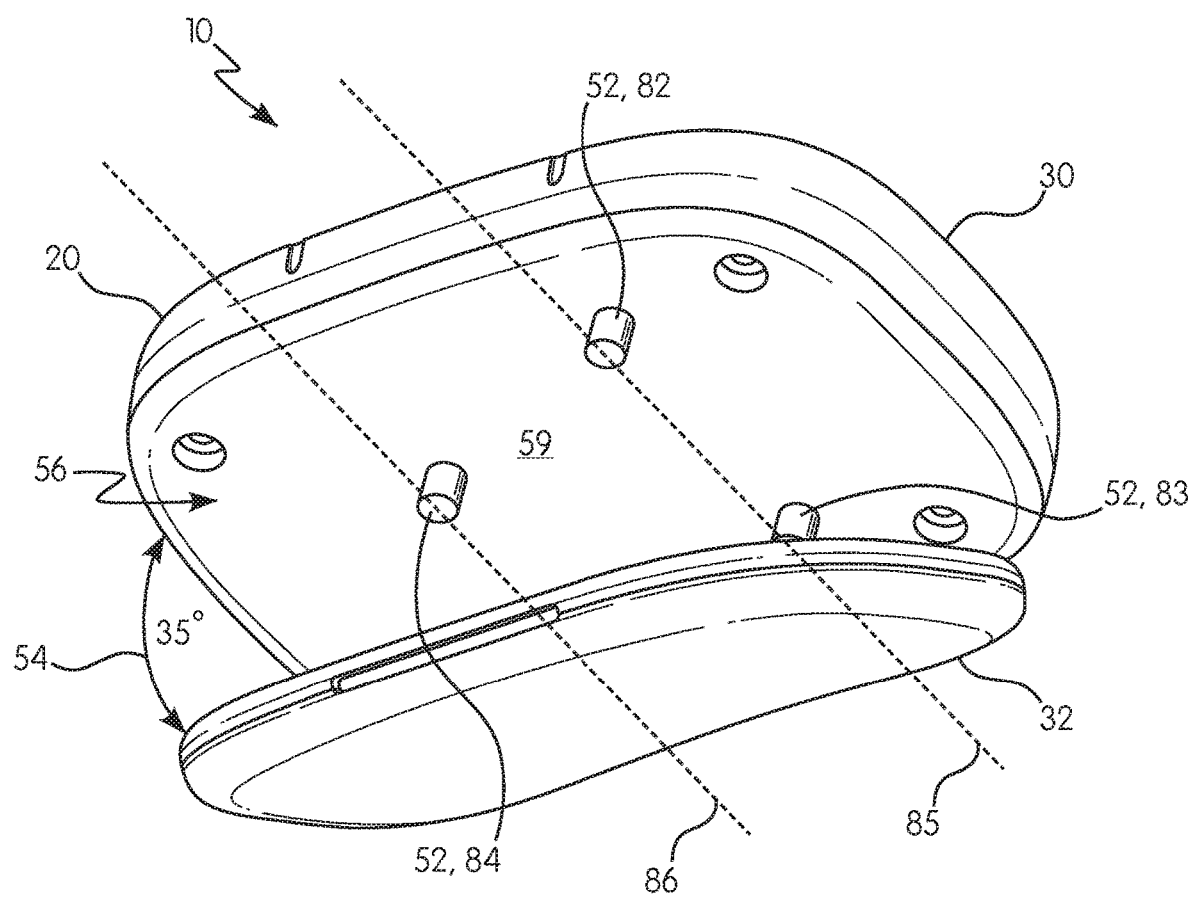
FIG. 14 is a perspective view of a monitoring device with a locking mechanism in a second position in accordance with an embodiment of the present invention.
Figure 15:
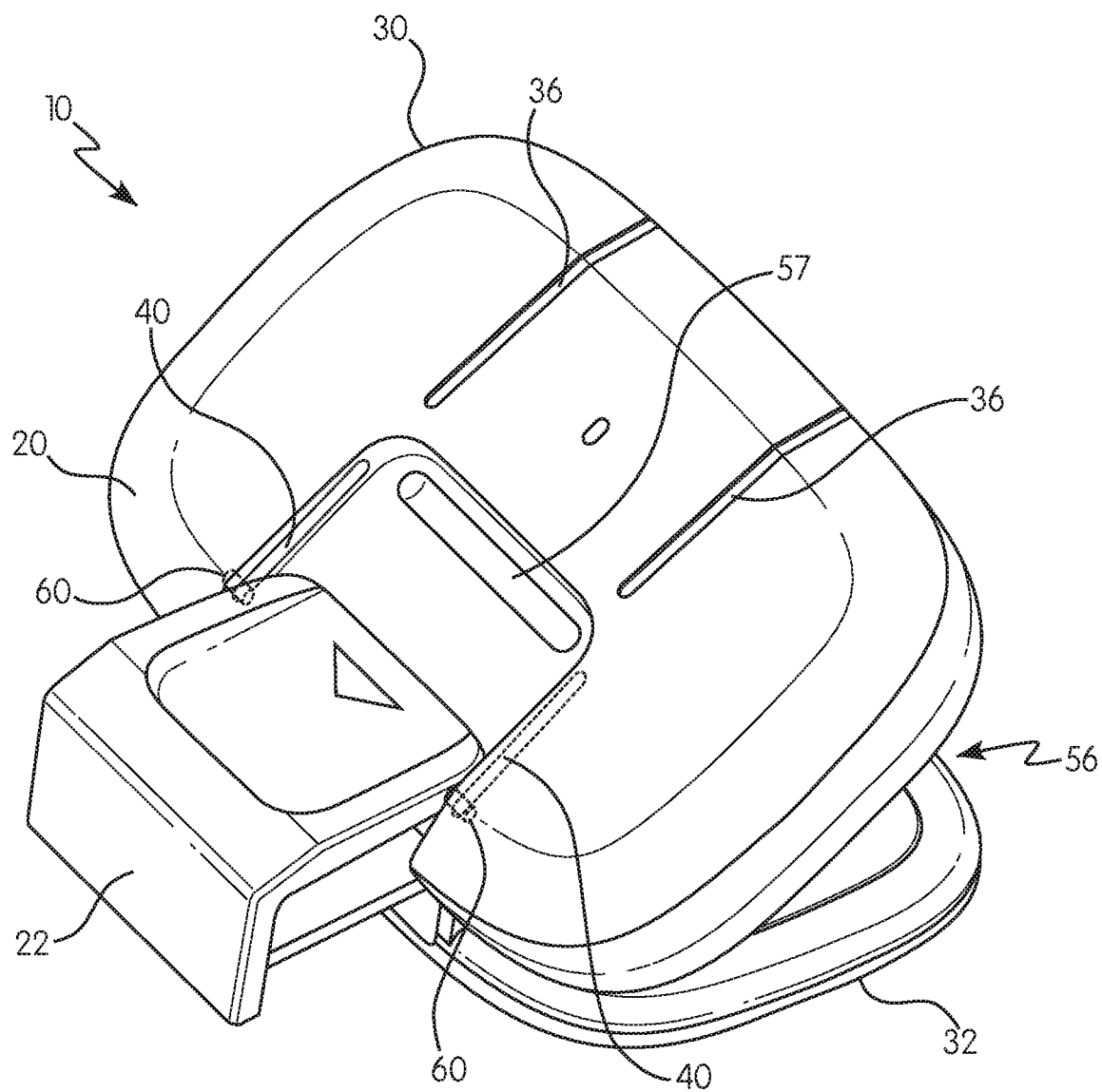
FIG. 15 is a perspective view of a monitoring device with a locking mechanism in a second position in accordance with another embodiment of the present invention.
Figure 16:
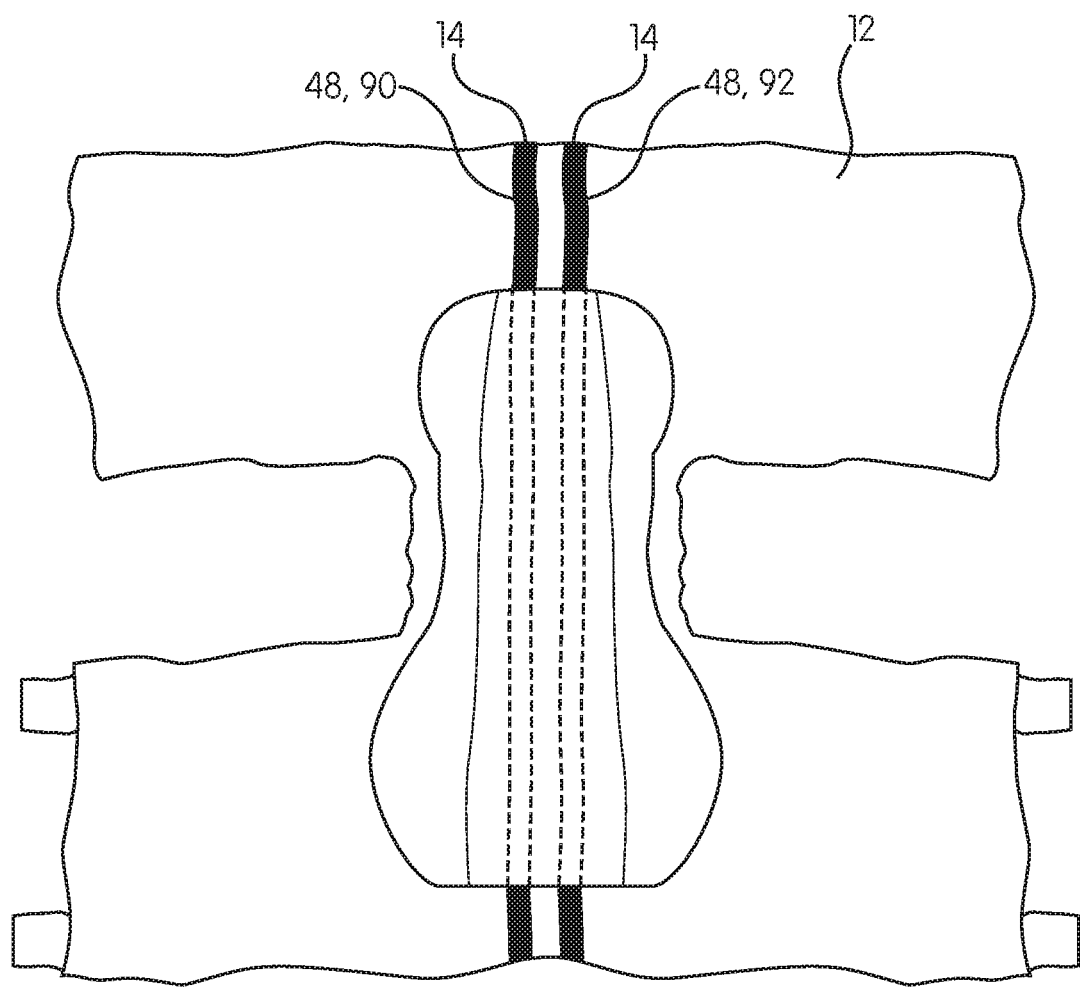
FIG. 16 is an elevation view of a garment in accordance with an embodiment of the present invention.

In some non-limiting embodiments, the top portion 30 is movably connectable to the bottom portion 32 of the clip 20 via a hinge portion 33. In this manner, the top portion 30 is movably connected to the bottom portion 32 of the clip 20 between the closed position (FIGS. 11, 12, 17, and 18) and the open position (FIGS. 13-15). In other embodiments, the top portion 30 is movably connectable to the bottom portion 32 of the clip 20 via other mechanical systems that allow the top portion 30 to move or swing open between the closed position (FIGS. 11, 12, 17, and 18) and the open position (FIGS. 13-15).

Referring to FIGS. 13-15, in some non-limiting embodiments, with the clip 20 in the open position in which the top portion 30 is spaced away from the bottom portion 32, an opening angle 54 between the top portion 30 and the bottom portion 32 is 35° or less. In this manner, the top portion 30 is spaced away from the bottom portion 32 a sufficient distance to allow a portion of a garment 12 to be securely received within the opening 56 formed between the top portion 30 and the bottom portion 32. Importantly, in the open position, the distance the top portion 30 is spaced away from the bottom portion 32 is controlled to allow a caregiver to position the garment 12 within the opening 56 formed between the top portion 30 and the bottom portion 32 and move the locking mechanism 22 into the first position to lock the clip 20 in the closed position, thereby securely attaching the clip 20 to the garment 12 using only one hand. This is important because the monitoring device 10 of the present disclosure only requires one hand of the caregiver to operate the monitoring device 10, thereby freeing the other hand of the caregiver to steady a patient and/or the garment 12 and/or be free to use for other activities needed in administering help to a patient.

Referring to FIG. 15, in some non-limiting embodiments, the top portion 30 of the clip 20 includes a rail 40 that is in communication with a portion of the locking mechanism 22 to allow a caregiver to easily open and close the monitoring device 10 using only one hand, as described in more detail below. In some non-limiting embodiments, the top portion 30 of the clip 20 includes two opposing rails 40.

Figure 19:
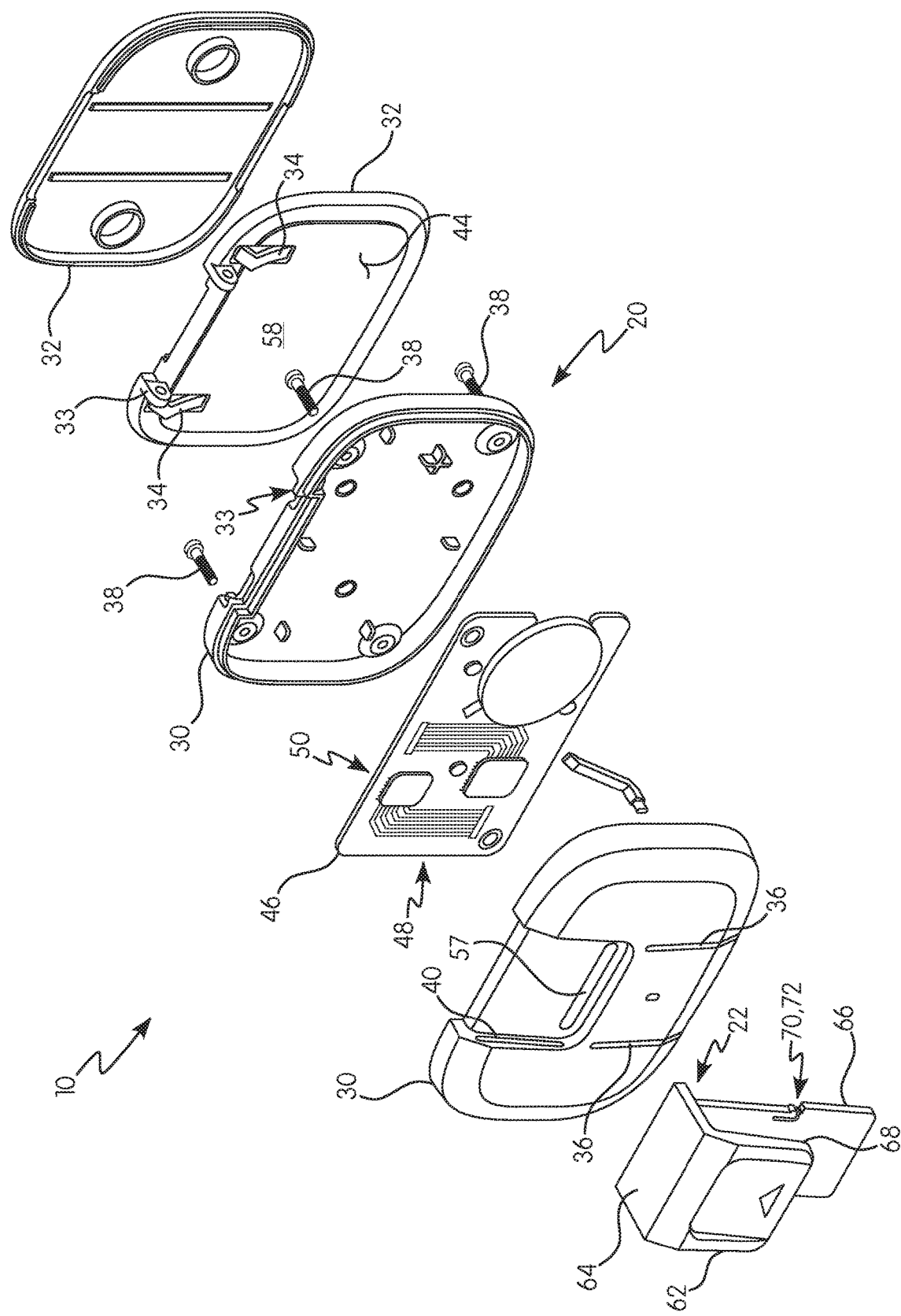
FIG. 19 is a first exploded, perspective view of a monitoring device in accordance with an embodiment of the present invention.
Figure 20:
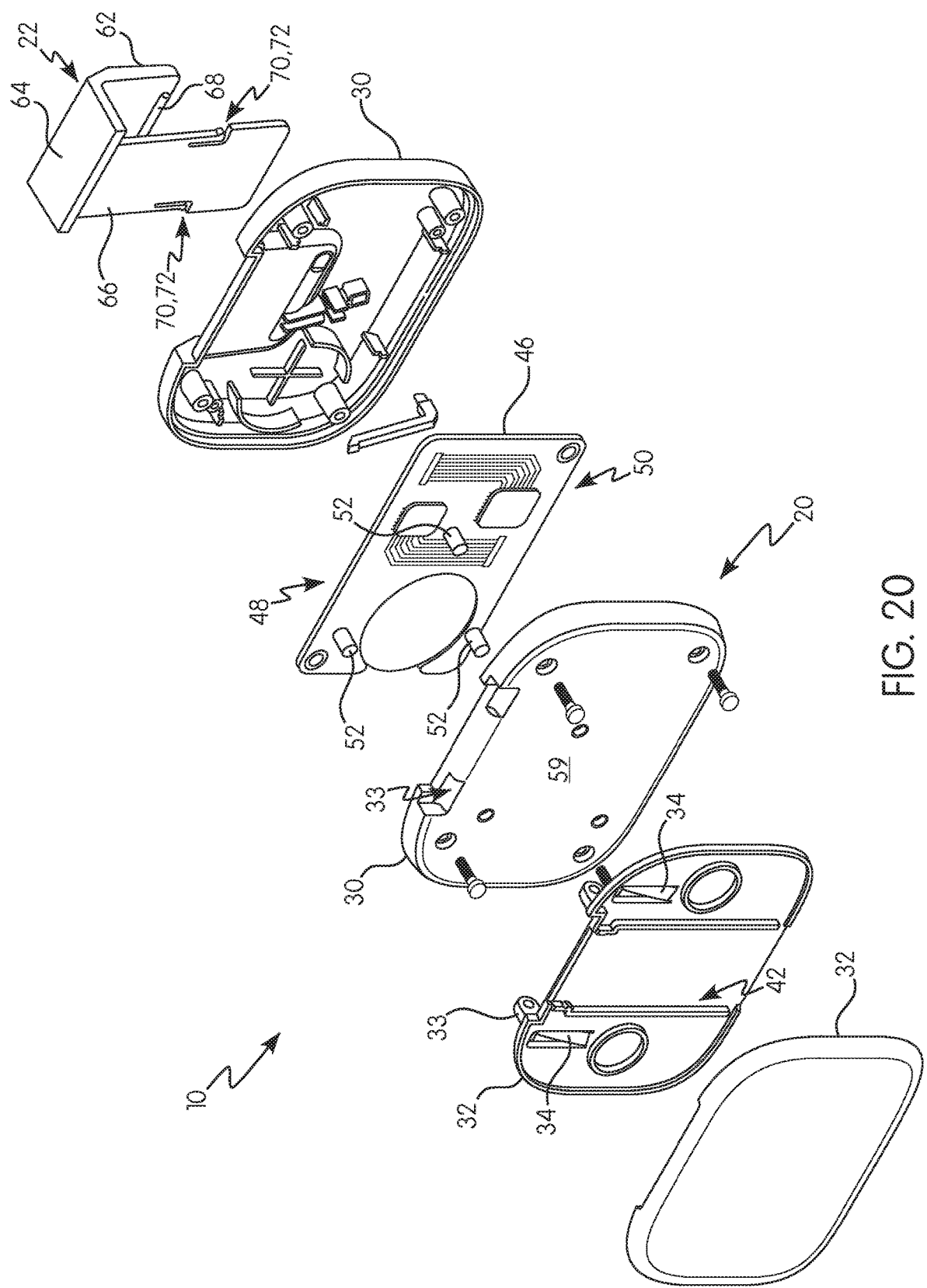
FIG. 20 is a second exploded, perspective view of a monitoring device in accordance with an embodiment of the present invention.

Referring to FIGS. 19 and 20, in an exemplary embodiment, the top portion 30 and the bottom portion 32 of the clip 20 may comprise two portions that are secured together using a plurality of fasteners 38.

Figure 21:
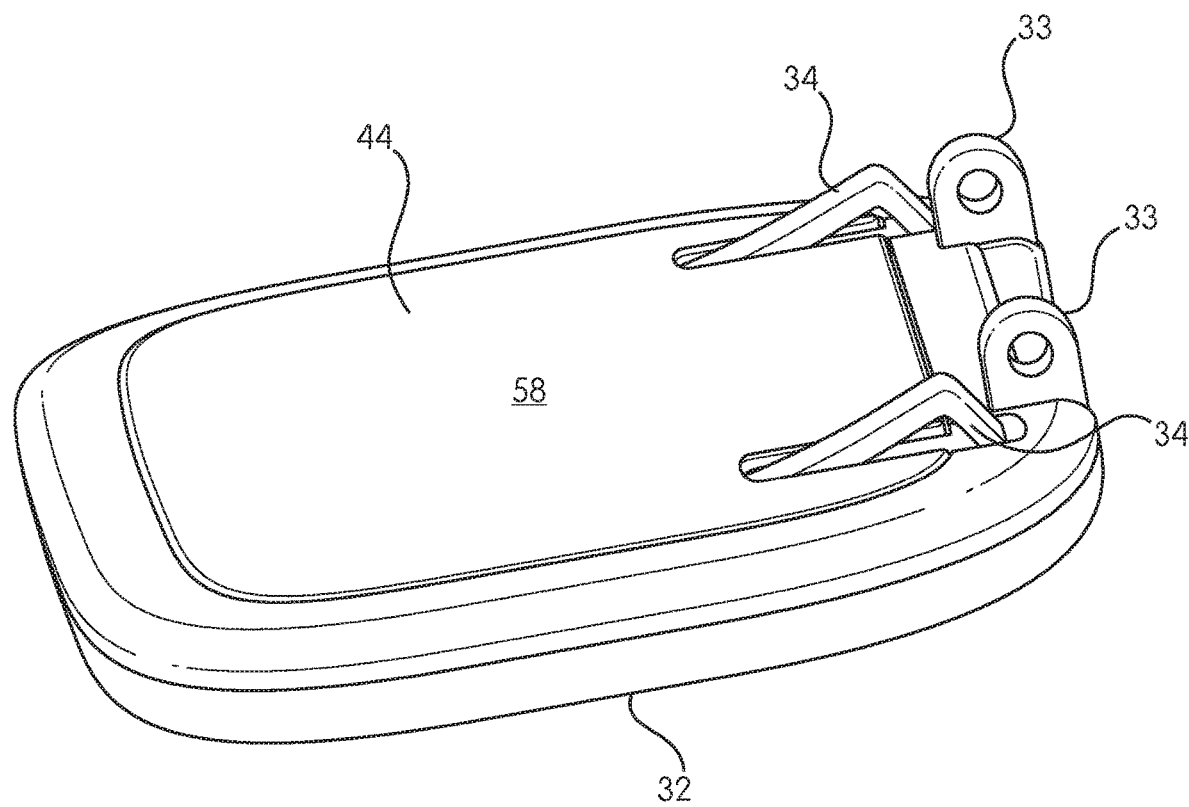
FIG. 21 is a top perspective view of a bottom portion of a clip including a resilient member in an undeformed position in accordance with an embodiment of the present invention.

The monitoring device 10 of the present disclosure also includes additional mechanisms to maintain the clip 20 in the open position, thereby making the monitoring device 10 easy to use with only one hand. For example, referring to FIGS. 19-24, in some non-limiting embodiments, the bottom portion 32 of the clip 20 includes a resilient member 34 that is transitionable between a deformed position (FIGS. 22 and 24) and an undeformed position (FIGS. 21 and 23). In one exemplary embodiment, the resilient member 34 is formed integrally with the bottom portion 32 of the clip 20.

Figure 22:
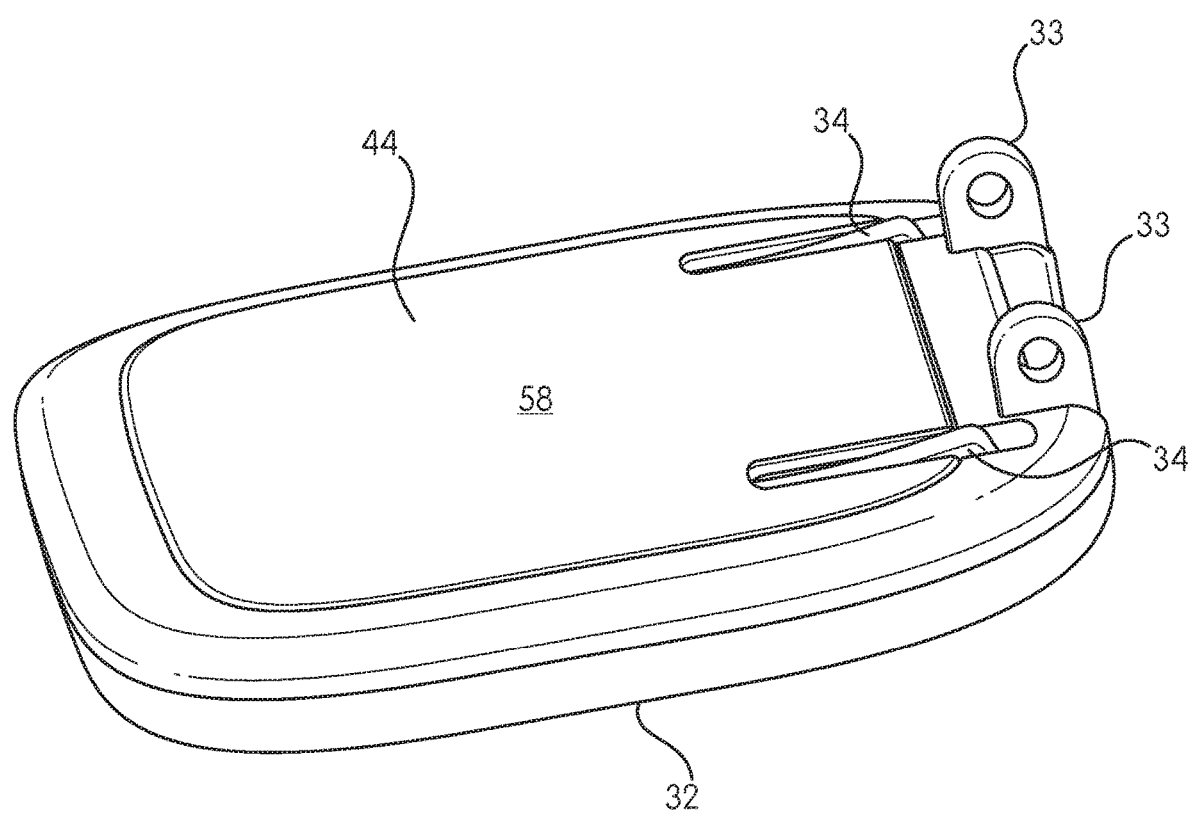
FIG. 22 is a top perspective view of a bottom portion of a clip including a resilient member in a deformed position in accordance with an embodiment of the present invention.
Figure 23:
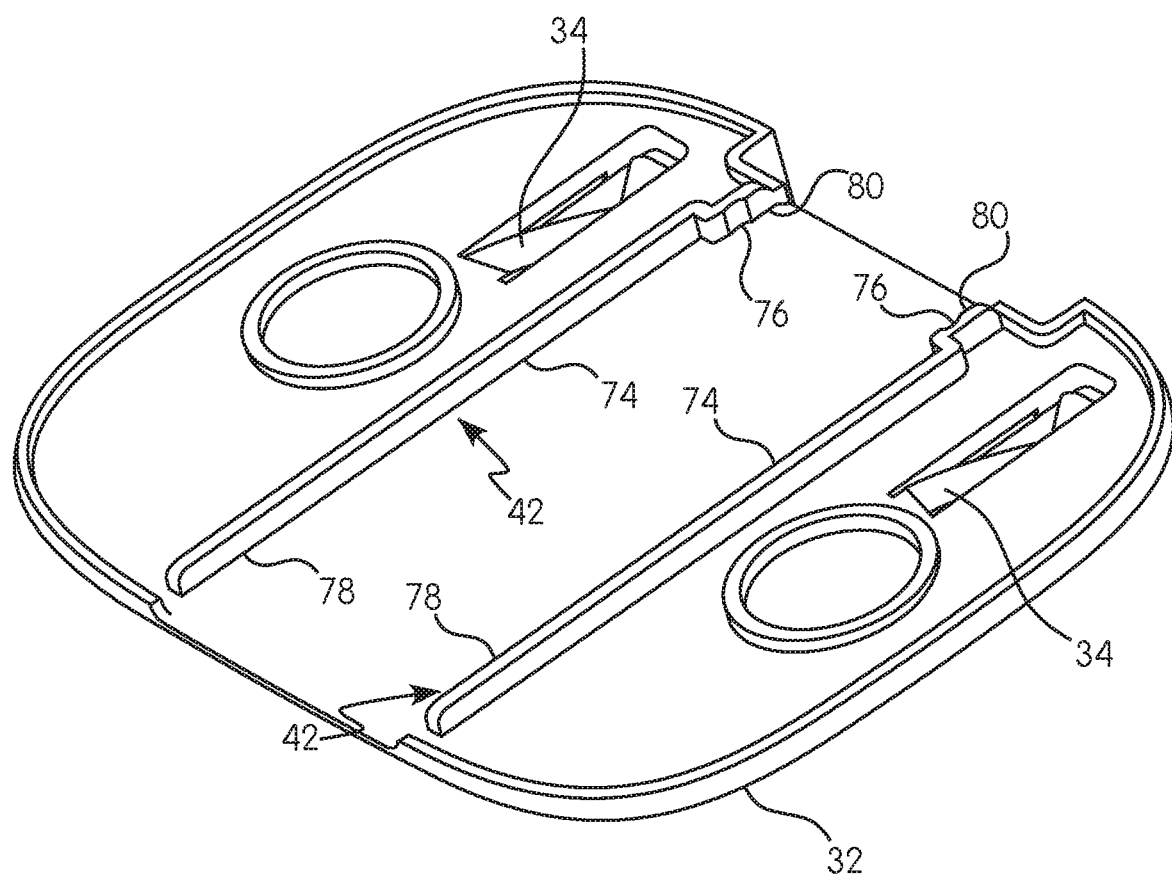
FIG. 23 is a bottom perspective view of a bottom portion of a clip including a resilient member in an undeformed position in accordance with an embodiment of the present invention.
Figure 24:
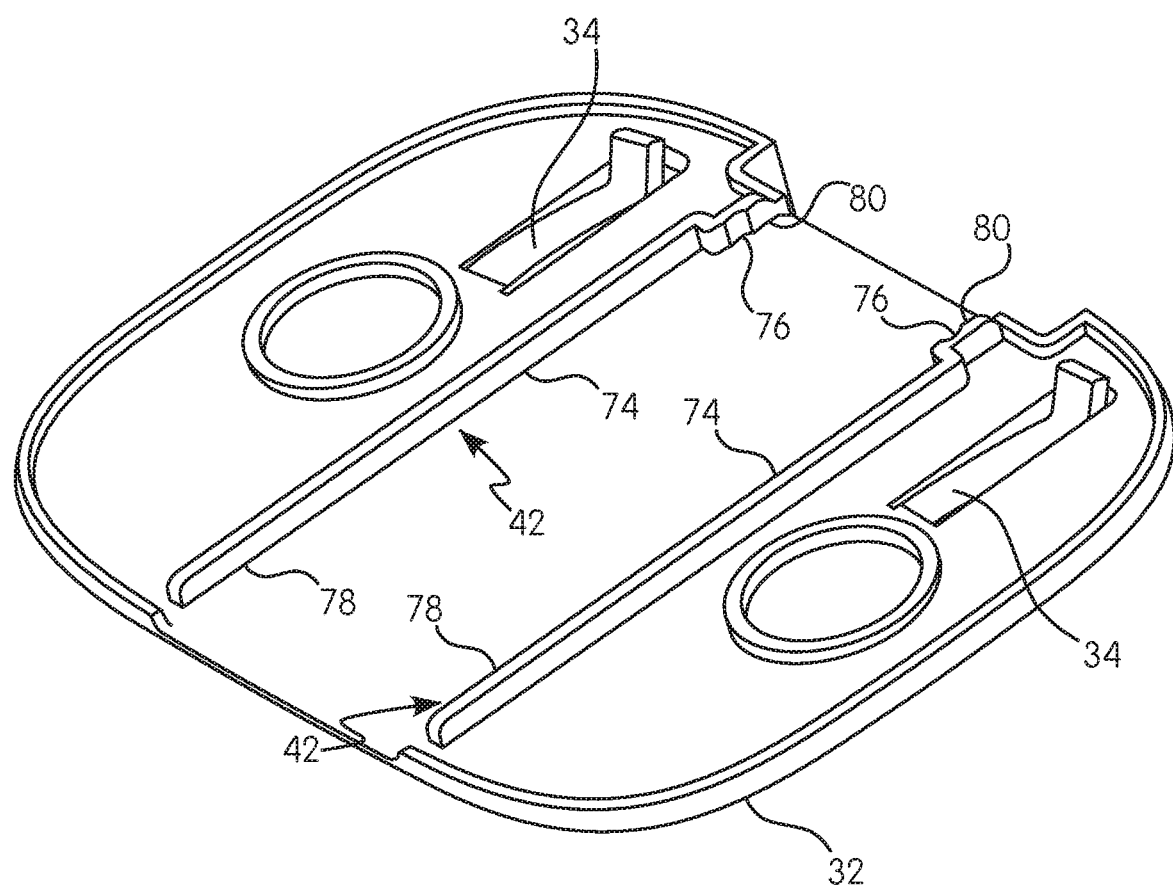
FIG. 24 is a bottom perspective view of a bottom portion of a clip including a resilient member in a deformed position in accordance with an embodiment of the present invention.

Referring to FIGS. 11, 12, 17, and 18, with the clip 20 in the closed position, the resilient member 34 is in the deformed position (FIGS. 22 and 24). Referring to FIGS. 13-15, with the clip 20 in the open position, the resilient member 34 is in the undeformed position (FIGS. 21 and 23).

Importantly, when the clip 20 moves from the open position to the closed position, as the top portion 30 of the clip 20 moves towards the bottom portion 32 of the clip 20, the top portion 30 contacts and forces the resilient member 34 to the deformed position. In other words, the top portion 30 compresses the resilient member 34 into the deformed position. In this manner, the resilient member 34 stores a force and when the clip 20 is subsequently moved from the closed position to the open position, the resilient member 34 exerts the stored force on the top portion 30 of the clip 20 as the resilient member 34 springs back into its undeformed position (FIGS. 21 and 23). Importantly, in this manner, the resilient member 34 helps to automatically open the clip 20. Also, with the clip 20 in the open position (FIGS. 13-15), and with the locking mechanism 22 in the second position, the clip 20 is locked in the open position by the resilient member 34 in the undeformed position exerting a force on the top portion 30 of the clip 20. This force exerted by the resilient member 34 automatically maintains the clip 20 in the open position. This enables a caregiver to not have to hold the clip 20 in an open position and enables one-handed operation of the monitoring device 10 of the present disclosure.

Referring to FIGS. 13 and 19, a portion of the clip 20 includes an elastomeric portion 44. In some non-limiting embodiments, a top surface 58 of the bottom portion 32 of the clip 20 includes an elastomeric portion 44. In another embodiment, a bottom surface 59 of the top portion 30 of the clip 20 includes an elastomeric portion 44. In other embodiments, a top surface 58 of the bottom portion 32 of the clip 20 includes an elastomeric portion 44 and a bottom surface 59 of the top portion 30 of the clip 20 includes an elastomeric portion 44.

The elastomeric portion 44 of the clip 20 provides a gripping surface that securely grips and holds a portion of the garment 12 within the clip 20. For example, with the clip 20 in the closed position and the clip 20 attached to the garment 12, the elastomeric portion 44 securely grips and holds the garment 12 within the clip 20. The elastomeric portion 44 provides an additional attachment mechanism in addition to the clip 20 and the locking mechanism 22 to ensure that a garment 12 is securely attached to the monitoring device 10.

Referring to FIGS. 19 and 20, the clip 20 includes a printed circuit board 46, a transmitter 50, and pins 52. In some non-limiting embodiments, the pins 52 are configured to determine moisture data associated with moisture in the sensors 48 (e.g., on the sensors, near the sensors, etc.) of the garment 12, and connect to the transmitter 50 configured to transmit the moisture data to a computer system comprising one or more processors (e.g., a central computer, a cloud computer, etc.).

For example, in one exemplary embodiment, the sensor 48 of the garment 12, the transmitter 50, and the computer system of the present disclosure comprises the system described in PCT Application No. PCT/US17/63042, filed Nov. 22, 2017, entitled "Monitoring Device, System, and Method for Incontinence Sensor Pad and Transmitter", the entire disclosure of which is hereby expressly incorporated herein by reference.

In some non-limiting embodiments, the transmitter 50 is included within the clip 20. In other embodiments, sensors 48 may be included in the garment 12 and the pins 52, attached to the printed circuit board 46 of the clip 20, extend through a portion of the top portion 30 into the opening 56 of the clip 20 to form connection points to both power and receive a signal from the sensors 48. For example, sensors may be attached to an interior portion of a garment 12. Although in FIG. 14 the pins 52 appear to have a flat head, it is contemplated that the heads of the pins 52 have teeth. For example, in some non-limiting embodiments, these pins 52 are crowned, e.g., the heads of the pins 52 have teeth allowing them to reliably penetrate through a top layer of non-woven textile on a portion of the garment 12 and penetrate into a sensor and/or sensor ink.

In one exemplary embodiment, the printed circuit board 46 may be contained within the top portion 30 of the clip 20. In another exemplary embodiment, the printed circuit board 46 may be contained within the bottom portion 32 of the clip 20. In one exemplary embodiment, the portion 30, 32 of the clip 20 that contains the printed circuit board 46 includes a removable access portion, such as a sliding tab (e.g., lock, enclosure, etc.). Such a removable access portion allows for easy access to the interior of the portion 30, 32 of the clip 20 that contains the printed circuit board 46. In this manner, tasks such as changing the printed circuit board 46, repair, changing the battery, or diagnostics can be accomplished easily and without taking the whole monitoring device 10 apart.

As described above, referring to FIGS. 11-15, the locking mechanism 22 is movably connected to the clip 20. In an exemplary embodiment, the locking mechanism 22 is transitionable between a first position (FIGS. 11, 12, 17, and 18) in which the locking mechanism 22 locks the clip 20 in a closed position and a second position (FIGS. 13-15) in which the clip 20 is in an open position.

Referring to FIGS. 11-18, in an exemplary embodiment, the locking mechanism 22 is movably connected to the clip 20, such that the locking mechanism 22 slides back and forth relative to the clip 20 between the first position (FIGS. 11, 12, 17, and 18) and the second position (FIGS. 13-15).

In an exemplary embodiment, as the locking mechanism 22 transitions from the first position to the second position, the locking mechanism 22 helps to open the clip 20. For example, referring to FIG. 15, in some non-limiting embodiments, the locking mechanism 22 includes a protrusion 60 that is movable and/or slidable within the rail 40 of the clip 20. Referring to FIG. 15, in some non-limiting embodiments, the locking mechanism 22 includes two opposing protrusions 60 that are respectively received within the two opposing rails 40 on the top portion 30 of the clip 20. In this manner, the rail 40 of the clip 20 guides movement of the locking mechanism 22 relative to the clip 20 between the first position (FIGS. 11, 12, 17, and 18) and the second position (FIGS. 13-15).

Importantly, as the locking mechanism 22 transitions from the first position (FIGS. 11, 12, 17, and 18) to the second position (FIGS. 13-15), the protrusion 60 of the locking mechanism 22 within the rail 40 of the clip 20 exerts a force on the top portion 30 of the clip 20, such that the locking mechanism 22 helps to open the clip 20, i.e., the locking mechanism 22 helps to pull the top portion 30 of the clip 20 away from the bottom portion 32 of the clip 20. The protrusion 60 of the locking mechanism 22 exerts a force on the top portion 30 of the clip 20 via the engagement of the protrusion 60 within the rail 40 of the clip 20. In this manner, the locking mechanism 22 of the present disclosure allows a caregiver to easily open and close the monitoring device 10 using only one hand. This is important because the monitoring device 10 of the present disclosure only requires one hand of the caregiver to operate the monitoring device 10, thereby freeing the other hand of the caregiver to steady a patient and/or the garment 12 and/or be free to use for other activities needed in administering help to a patient.

In one exemplary embodiment, the locking mechanism 22 generally includes a top part 62, a side part 64, and a bottom part 66. Referring to FIGS. 19 and 20, in some non-limiting embodiments, the top part 62, the side part 64, and the bottom part 66 of the locking mechanism 22 form a generally J-shape.

In some non-limiting embodiments, the monitoring device 10 of the present disclosure includes a locking mechanism for maintaining and locking the locking mechanism 22 relative to the clip 20, with the locking mechanism 22 in the first position (FIGS. 11, 12, 17, and 18), i.e., with the locking mechanism 22 locking the clip 20 in the closed position. For example, in an exemplary embodiment, the top part 62 of the locking mechanism 22 includes a protruding rib 68 (FIGS. 19 and 20) and the top portion 30 of the clip 20 defines a groove 57 (FIGS. 13 and 15). In this manner, with the locking mechanism 22 in the first position (FIGS. 11, 12, 17, and 18), the protruding rib 68 of the locking mechanism 22 locks within the groove 57 of the clip 20 to maintain and lock the locking mechanism 22 relative to the clip 20, with the locking mechanism 22 in the first position (FIGS. 11, 12, 17, and 18), i.e., with the locking mechanism 22 locking the clip 20 in the closed position.

In some non-limiting embodiments, the monitoring device 10 of the present disclosure includes an additional locking mechanism for maintaining and locking the locking mechanism 22 relative to the clip 20, with the locking mechanism 22 in the second position (FIGS. 13-15) in which the clip 20 is in an open position.

For example, in an exemplary embodiment, the bottom part 66 of the locking mechanism 22 includes a link or second detent portion 70 movably connected to the bottom part 66 of the locking mechanism 22 and the bottom portion 32 of the clip 20, and with the locking mechanism 22 in the second position (FIGS. 13-15), the link or second detent portion 70 locks the locking mechanism 22 relative to the clip 20 so that movement of the locking mechanism 22 relative to the clip 20 is prevented.

In some non-limiting embodiments, the links 42, 70 comprise a detent system. For example, in some non-limiting embodiments, the second detent portion 70 of the locking mechanism 22 includes a resiliently deformable portion 72 and the first detent portion 42 of the clip 20 includes detent rails 74 on the bottom portion 32 of the clip 20 and locking apertures 76. In some non-limiting embodiments, the detent rails 74 include a first portion 78 and a second portion 80. The second portion 80 of the detent rails 74 defines the locking apertures 76. The second portion 80 of the detent rails 74 are spaced closer together than the first portion 78 of the detent rails 74 so that the second portion 80 of the detent rails 74 compress the resiliently deformable portion 72 of the locking mechanism 22 as described below.

Figure 25:
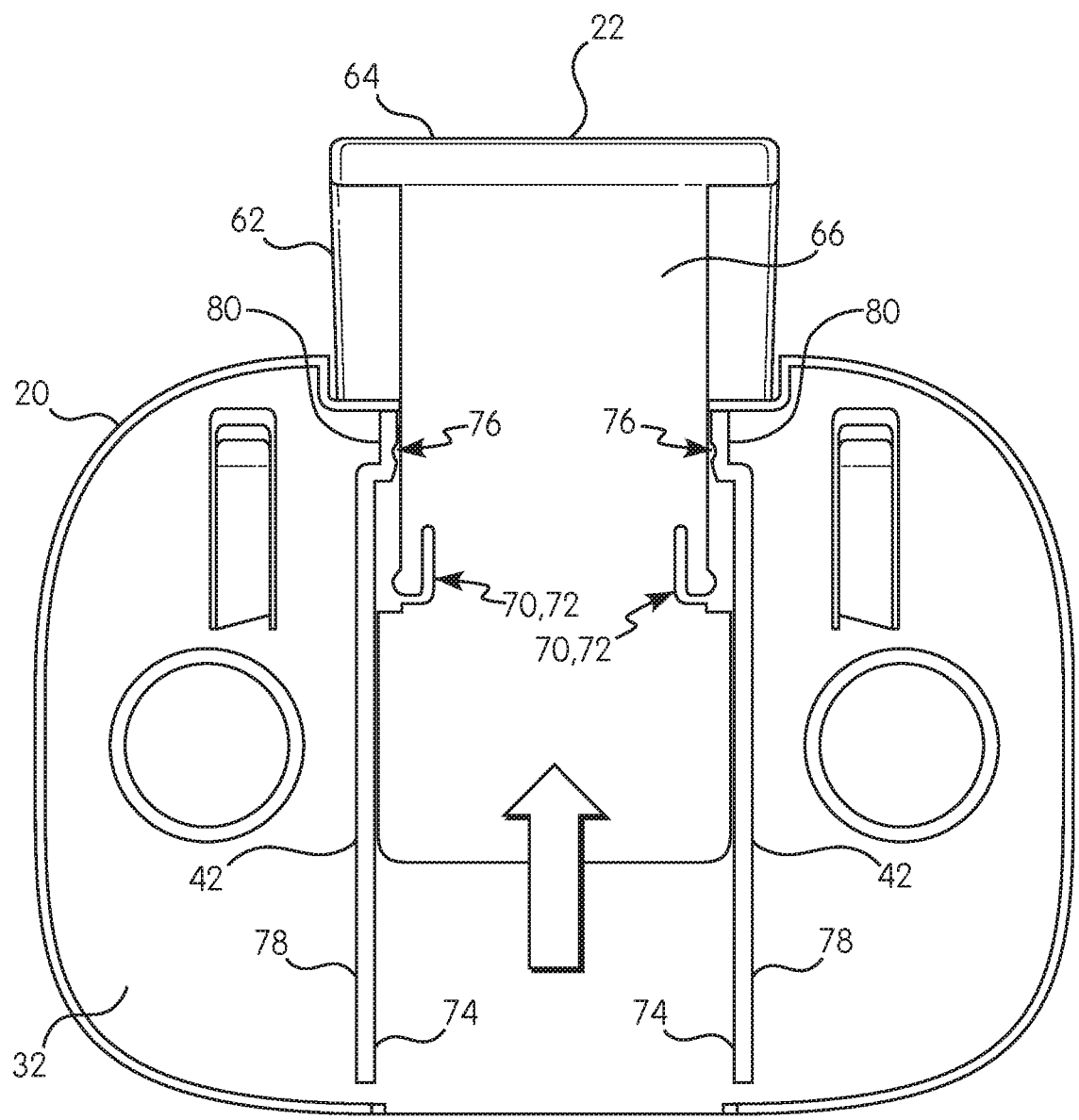
FIG. 25 is a perspective view of a detent system of a monitoring device in a first position in accordance with an embodiment of the present invention.
Figure 26:
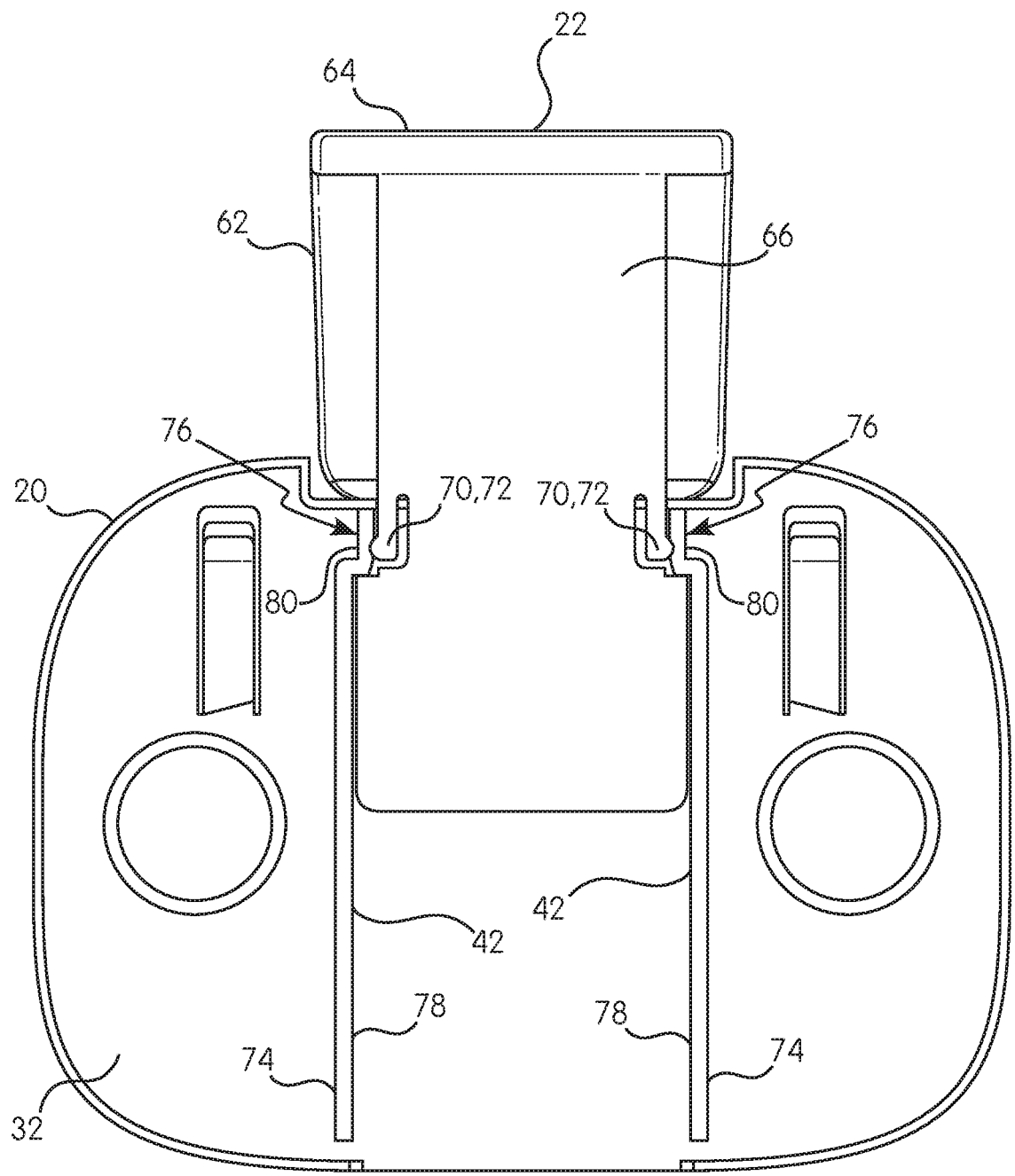
FIG. 26 is a perspective view of a detent system of a monitoring device in a second position in accordance with an embodiment of the present invention.

Referring to FIGS. 25 and 26, as the locking mechanism 22 transitions from the first position (FIGS. 11, 12, 17, and 18) to the second position (FIGS. 13-15 and 26), the deformable portion 72 of the second detent portion 70 of the locking mechanism 22 travels between the first portion 78 of the detent rails 74. When the deformable portion 72 of the locking mechanism 22 reaches the beginning of the second portion 80 of the detent rails 74, the second portion 80 of the detent rails 74 contacts and deforms the deformable portion 72 of the locking mechanism 22 inwards, thereby storing a force. The locking mechanism 22 continues to transition from the first position (FIGS. 11, 12, 17, and 18) to the second position (FIGS. 13-15 and 26) until the deformable portion 72 of the locking mechanism 22 reaches the locking apertures 76 of the second portion 80 of the first detent portion 42 of the clip 20. At this point, the energy stored within the deformable portion 72 of the locking mechanism 22 is released and the deformable portion 72 snaps into the locking apertures 76, thereby locking the locking mechanism 22 relative to the clip 20 so that movement of the locking mechanism 22 relative to the clip 20, is prevented with the locking mechanism 22 in the second position (FIGS. 13-15 and 26) in which the clip 20 is in an open position. This mechanism also helps to allow a caregiver to easily use the monitoring device 10 using only one hand.

Referring to FIG. 13, when a caregiver is aligning the monitoring device 10 relative to a garment 12 before securely attaching the monitoring device 10 to the garment 12, a caregiver only needs one hand because the locking mechanism 22 is securely maintained in the second position. If the top portion 30 and the bottom portion 32 of the clip were not locked into position and were freely moving between each other, it would take a caregiver two hands just to maintain the clip in an open position. The present disclosure allowing for one-handed use is important because the monitoring device 10 of the present disclosure only requires one hand of the caregiver to operate the monitoring device 10, thereby freeing the other hand of the caregiver to steady a patient and/or the garment 12 and/or be free to use for other activities needed in administering help to a patient.

In some non-limiting embodiments, the locking mechanism 22 comprises a polymer component molded over a metal component. In other embodiments, the locking mechanism 22 may comprise other materials and/or combinations of materials that provide a sufficient strength to lock the clip 20 in the closed position (FIGS. 11, 12, 17, and 18).

Advantageously, the monitoring device 10 of the present disclosure may be part of a monitoring system. For example, a monitoring device 10 of the present disclosure is reusable and can be used an unlimited amount of times with an unlimited amount of disposable garments 12. Thus, a single monitoring device 10 of the present disclosure can be used with a first garment 12 to detect wetness in the first garment 12. After use, the first garment 12 is disposed of and the monitoring device 10 of the present disclosure can be reused with a second garment 12.

Referring to FIGS. 11-18, use of a monitoring device 10 of the present disclosure will now be described.

Referring to FIG. 13, with the locking mechanism 22 in the second position in which the clip 20 is in an open position, and with the locking mechanism 22 locked relative to the clip 20 so that movement of the locking mechanism 22 relative to the clip 20 is prevented using links 42, 70, as described above, a caregiver is able to use only one hand to align and maneuver the monitoring device 10 relative to a garment 12. In some non-limiting embodiments, a caregiver aligns the guide lines 36 located on the top portion 30 of the clip 20 with guide lines 14 on the garment 12 to properly position the monitoring device 10 relative to the garment 12 before securely attaching the monitoring device 10 to the garment 12. These guide lines 14, 36 ensure that the monitoring device 10 is secured to the garment 12 in a proper position that will allow sensors 48 of the system to be aligned with pins 52 of the clip 20 so that the transmitter 50 of the monitoring device 10 is in communication with the sensors 48 that determine moisture data associated with moisture in the garment 12. In this manner, the transmitter 50 of the monitoring device 10 is able to connect to the sensor 48 and transmit the moisture data to a computer system comprising one or more processors.

Referring to FIG. 13, with the monitoring device 10 properly aligned with the garment 12, the caregiver is able to position a portion of the garment 12 within the opening 56 of the monitoring device 10, and then using only one hand, slide the locking mechanism 22 into the first position (FIGS. 11, 12, 17, and 18) in which the locking mechanism 22 locks the clip 20 in the closed position to securely attach the monitoring device 10 to the garment 12.

In a first configuration, referring to FIG. 17, the monitoring device 10 is secured to a portion of the garment 12 that has been folded over. In such a configuration, the folded over portion of the garment 12 provides an increased thickness portion of the garment 12 that is secured within the clip 20 of the monitoring device 10. In this manner, the thicker portion of the garment 12 can lead to a more secure attachment between the monitoring device 10 and the garment 12.

In a second configuration, referring to FIG. 18, the monitoring device 10 is secured to the inside layer of a portion of the garment 12 that has been folded over. In such a configuration, the monitoring device 10 is secured to the garment 12 so that the monitoring device 10 does not contact any portion of a patient. In this manner, the monitoring device 10 is secured between two layers of the garment 12 and avoids contacting any skin surfaces of a patient. Both of the configurations of FIGS. 17 and 18 lead to a secure attachment between the monitoring device 10 and a garment 12.

With the monitoring device 10 properly attached to a garment 12, the monitoring device 10 is able to detect wetness in a garment. For example, in one exemplary embodiment, the sensor 48, the transmitter 50, and the computer system of the present disclosure for detecting moisture data and transmitting the moisture data comprises a system described in PCT Application No. PCT/US17/63042, filed Nov. 22, 2017, entitled "Monitoring Device, System, and Method for Incontinence Sensor Pad and Transmitter", the entire disclosure of which is hereby expressly incorporated herein by reference.

After moisture data is determined and transmitted to a caregiver, the caregiver is able to remove the monitoring device 10 of the present disclosure using only one hand, as described above, and then the garment 12 is disposed. As described above, the monitoring device 10 of the present disclosure is then reusable with any number of additional garments 12.

The monitoring device 10 of the present disclosure provides a patient incontinence monitoring system for electronically detecting the presence of moisture in a patient care or home care environment. It can send a detection of moisture across a network to a third-party device (e.g., a computer, a remote pad, a smartphone, a cloud) for enabling the remote collection and analysis of incontinence data. This detection can also be used by a third-party device, such as a monitoring system, to determine patterns and/or alert a caregiver associated with an incontinence event.

Figure 27:
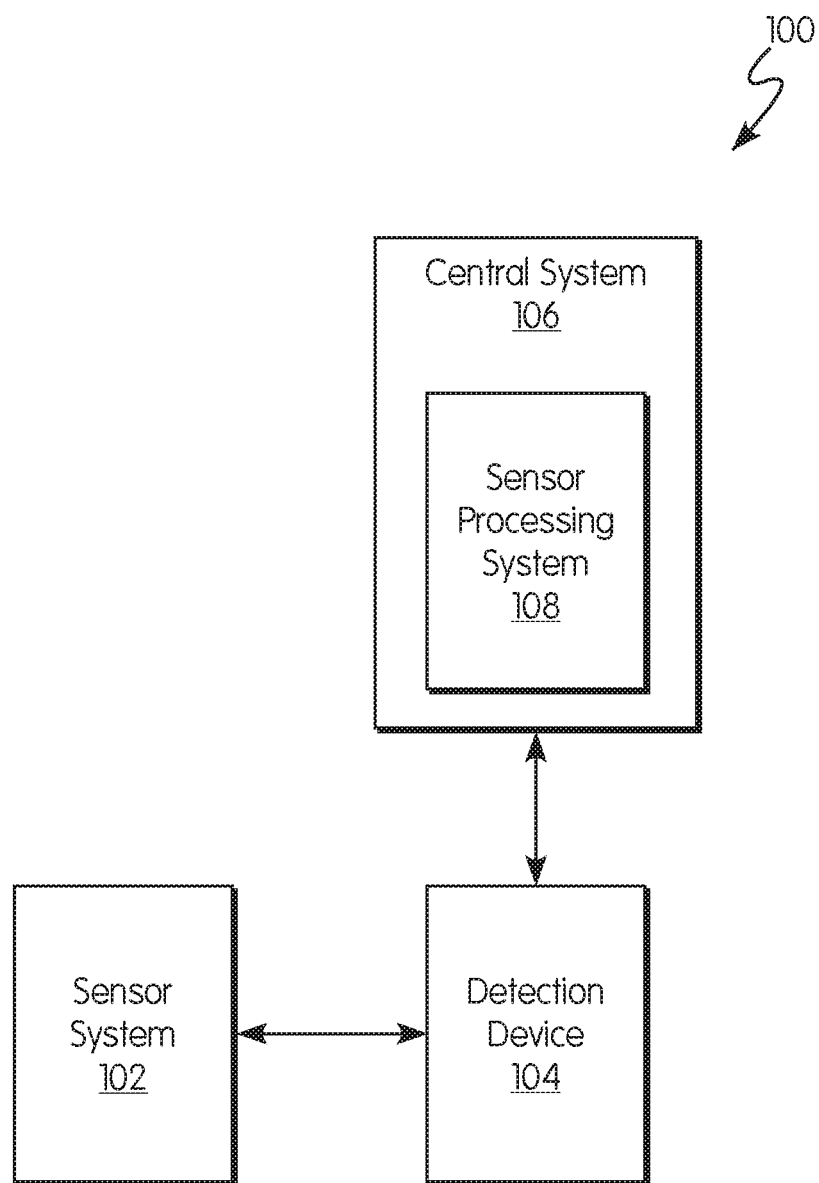
FIG. 27 is a first diagram showing a monitoring device and patient incontinence monitoring system in accordance with an embodiment of the present invention.
Figure 28:
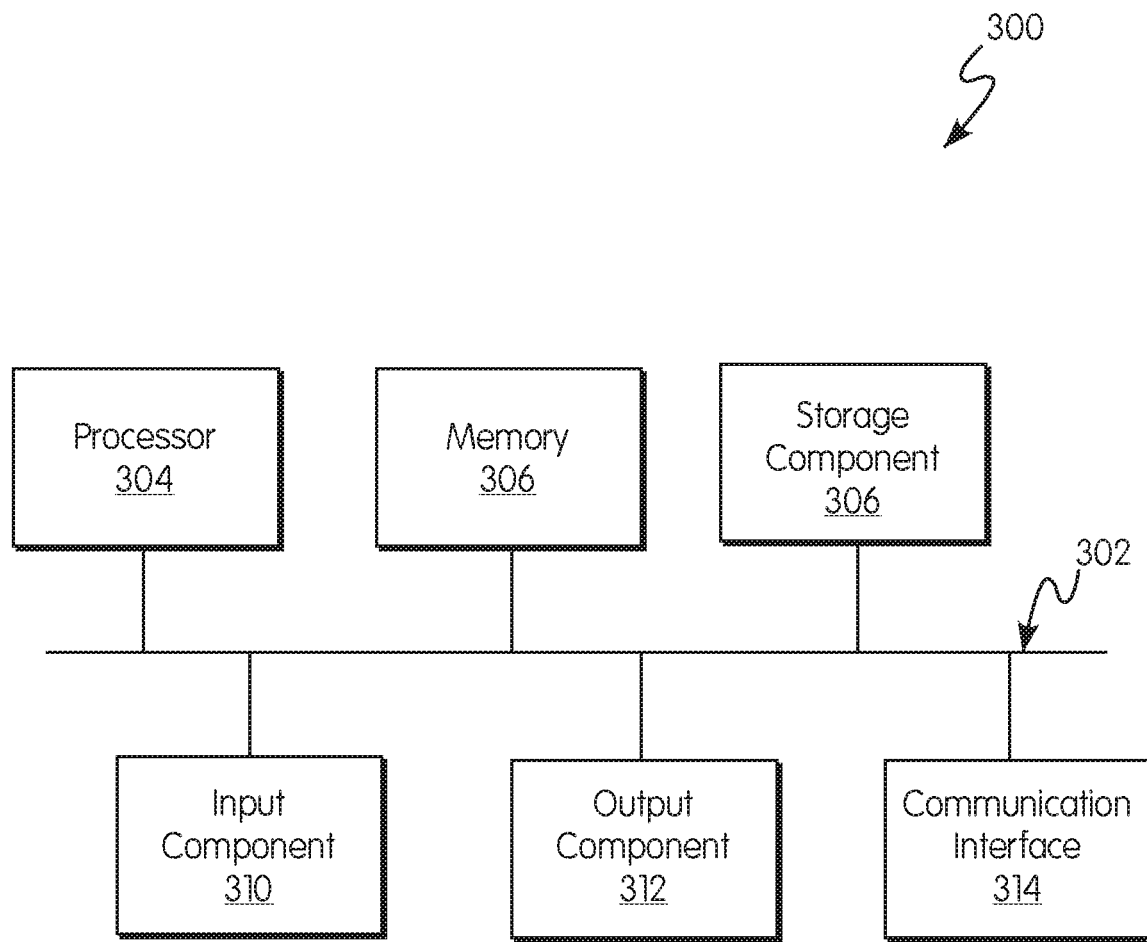
FIG. 28 is a second diagram showing a monitoring device and patient incontinence monitoring system in accordance with an embodiment of the present invention.
Figure 29:
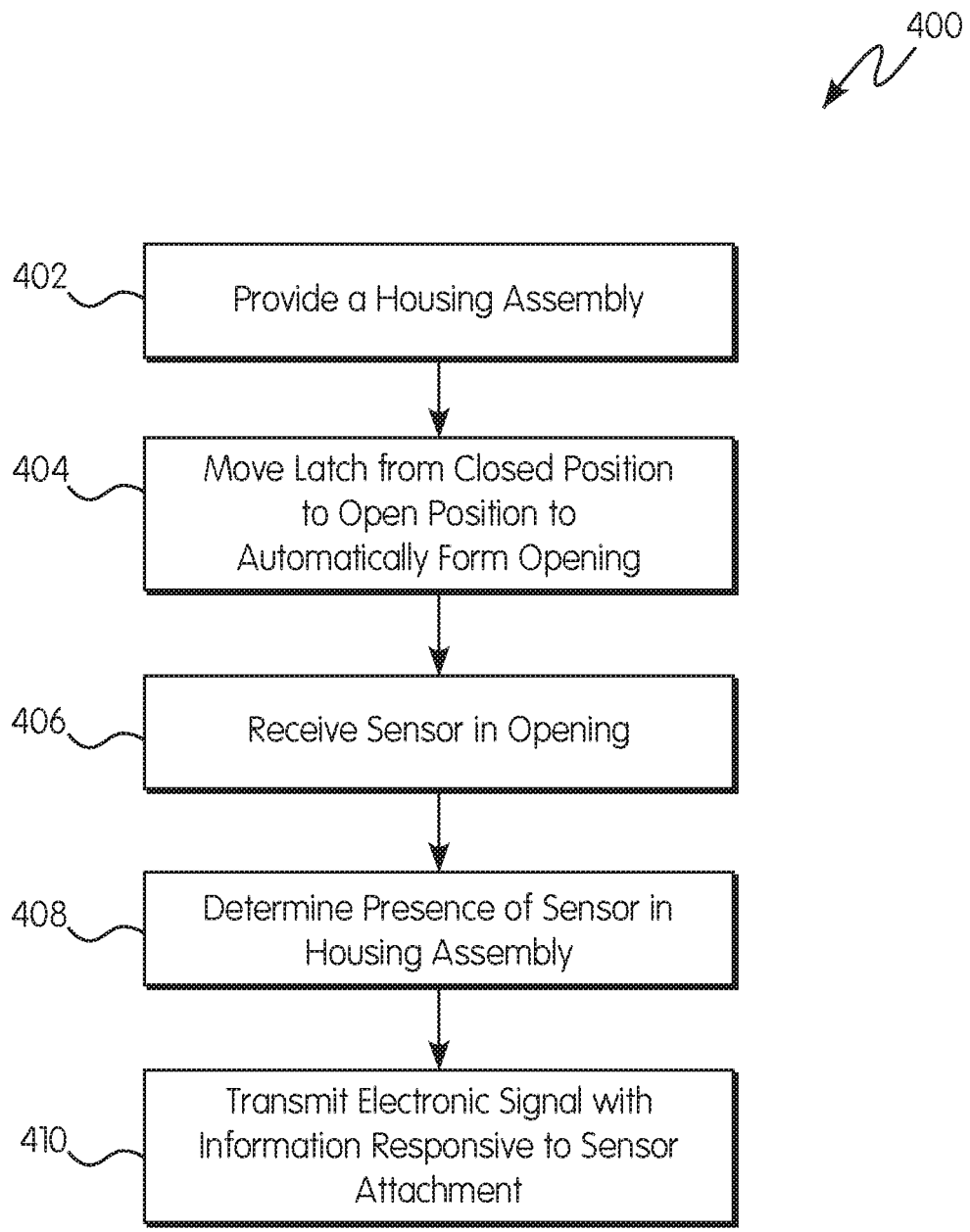
FIG. 29 is a flow chart showing a monitoring device and patient incontinence monitoring system in accordance with an embodiment of the present invention.

Furthermore, diagrams and/or flow charts of a system and/or device of the present disclosure are illustrated in FIGS. 27-29. Referring to FIG. 27, a system or device 100 includes a sensor system 102 configured to determine moisture data associated with moisture in a garment 12, a detection device 104, a central system 106, a sensor processing system 108, and a transmitter 50 configured to connect to the sensor 102 and transmit the moisture data to a computer system comprising one or more processors.

In an exemplary embodiment, each of the layers of a multi-layer location-based sensor pad may be made of an absorbent material. The sensor pad may be placed on a flat surface (e.g., a patient bed, a patient chair) and may also be placed on surfaces that are not flat, where the pad can take the shape of the surface. The pad can also be wrapped around a patient's body or configured to provide sufficient coverage for incontinence detection. The sensor pad may be placed inside a wearable unit and may take the shape of the wearable unit. In one exemplary embodiment, a sensor and/or sensor pad may be attached to an interior of a garment. For example, a sensor may be attached to an interior of a garment, such as, for example, briefs, diapers, pull-ups, or other wearable garments. In such embodiments, a sensor may be printed directly into a wearable garment with a tail coming out of a portion of the garment to facilitate the attachment with a transmitter.

Referring to FIG. 28, a diagram of a non-limiting embodiment of components of one or more monitoring devices and/or monitoring systems of the present disclosure is illustrated.

In one exemplary embodiment, FIG. 28 is a diagram of example components of a monitoring device 300 (e.g., monitoring system, etc.) of the present disclosure. Monitoring device 300 may correspond to one or more devices of a patient incontinence monitoring system, one or more monitoring devices of the present disclosure that may include at least one monitoring device 300, and/or at least one component of monitoring device 300. Referring to FIG. 28, the monitoring device 300 may include bus 302, processor 304, memory 306, storage component 308, input component 310, output component 312, and communication interface 314. In one embodiment, these elements of a computer and monitoring device 300 and the other elements of a computer and monitoring device 300 described herein correspond to the computer and software elements for built-in delay mechanisms, as described herein.

Bus 302 may include a component that permits communication among the components of monitoring device 300. In some non-limiting embodiments, processor 304 may be implemented in hardware, firmware, or a combination of hardware and software. For example, processor 304 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 306 may include a random access memory (RAM), a read only memory (ROM), and/or another type of dynamic or static storage device (e.g., flash memory, magnetic memory, optical memory, etc.) that stores information and/or instructions for use by processor 304.

Storage component 308 may store information and/or software related to the operation and use of monitoring device 300. For example, storage component 308 may include a hard disc (e.g., a magnetic disc, an optical disc, a magneto-optic disc, a solid state disc, etc.), a compact disc (CD), a digital versatile disc (DVD), a floppy disc, a cartridge, a magnetic tape, and/or another type of computer-readable medium, along with a corresponding drive.

Input component 310 may include a component that permits monitoring device 300 to receive information, such as via user input (e.g., a touch screen display, a keyboard, a keypad, a mouse, a button, a switch, a microphone, etc.). Additionally, or alternatively, input component 310 may include a sensor for sensing information (e.g., a global positioning system (GPS) component, an accelerometer, a gyroscope, an actuator, etc.). Output component 312 may include a component that provides output information from monitoring device 300 (e.g., a display, a speaker, one or more light-emitting diodes (LEDs), etc.).

Communication interface 314 may include a transceiver-like component (e.g., a transceiver, a separate receiver and transmitter, etc.) that enables monitoring device 300 to communicate with other devices, such as via a wired connection, a wireless connection, or a combination of wired and wireless connections. Communication interface 314 may permit monitoring device 300 to receive information from another device and/or provide information to another device. For example, communication interface 314 may include an Ethernet interface, an optical interface, a coaxial interface, an infrared interface, a radio frequency (RF) interface, a universal serial bus (USB) interface, a Wi-Fi interface, a cellular network interface, and/or the like.

Monitoring device 300 may perform one or more processes described herein. Monitoring device 300 may perform these processes based on processor 304 executing software instructions stored by a computer-readable medium, such as memory 306 and/or storage component 308. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 306 and/or storage component 308 from another computer-readable medium or from another device via communication interface 314. When executed, software instructions stored in memory 306 and/or storage component 308 may cause processor 304 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 28 are provided as an example. In some non-limiting embodiments, monitoring device 300 may include additional components, fewer components, different components, or differently arranged components than those shown in FIG. 28. Additionally, or alternatively, a set of components (e.g., one or more components) of monitoring device 300 may perform one or more functions described as being performed by another set of components of monitoring device 300.

Referring to FIG. 29, in some non-limiting embodiments, a computer-implemented monitoring method 400 includes steps 402, 404, 406, 408, 410 for patient care use in a patient incontinence monitoring system. As shown in FIG. 29, at step 402, monitoring method 400 includes providing a housing assembly. For example, monitoring method 400 includes a housing assembly for detecting wetness in a garment that includes a clip 20 and a locking mechanism 22 (e.g., a latch, etc.). The clip 20 and locking mechanism 22 provide a mechanism for removably attaching the monitoring device 10 to a garment 12. The monitoring device 10 of the present disclosure is compatible with any type of undergarment with sensors. For example, a sensor pad may be used in a healthcare facility for detection of wetness associated with a patient.

As shown in FIG. 29, at step 404, monitoring method 400 includes moving a latch from a closed position to an open position to automatically form an opening. For example, monitoring method 400 includes a locking mechanism 22 (e.g., a latch) providing transitions from a first position to a second position. In some non-limiting embodiments, monitoring method 400 includes moving a latch (e.g., a deformable portion 72 of a second detent portion 70 of the locking mechanism 22, etc.) between portions of detent rail 74. For example, monitoring method 400 includes moving a latch to transition from a first position to a second position in a location where a deformable portion 72 of a locking mechanism 22 reaches the locking apertures 76 of the second portion 80 of the first detent portion 42 of the clip 20. For example, monitoring method 400 includes moving a latch until the energy stored within the deformable portion 72 of the locking mechanism 22 is released and the deformable portion 72 snaps into the locking apertures 76, thereby locking the locking mechanism 22 relative to the clip 20 so that movement of the locking mechanism 22 relative to the clip 20 is prevented with the locking mechanism 22 in the second position in which the clip 20 is in an open position.

As shown in FIG. 29, at step 406, monitoring method 400 includes receiving a sensor in an opening. For example, the monitoring method 400 includes receiving a sensor (e.g., a sensor pad, a sensor brief, etc.) of a garment in the monitoring device. For example, monitoring device 10 receives sensors 48 attached to an interior portion of a garment 12. In an example, monitoring method 400 includes receiving a sensor printed directly into a wearable garment providing a tail coming out of a portion of the garment. In some non-limiting embodiments, monitoring method 400 includes receiving a sensor (e.g., an end of a sensor, a portion of a sensor, a connector of a sensor, etc.) in an opening of the monitoring device 10. For example, a sensor is received in an opening of the monitoring device where pins 52, extend through a portion into the opening 56 of the monitoring device to form a connection at a point (e.g., location, etc.) when paired with a sensor. In some non-limiting embodiments, monitoring method 400 includes receiving a sensor in an opening of the monitoring device 10 to both power and receive a signal from the sensors 48.

As shown in FIG. 29, at step 408, monitoring method 400 includes determining a presence of a sensor in a housing assembly. For example, monitoring method 400 includes determining a presence of a sensor in a housing assembly (e.g., a monitoring device 10, etc.) to secure a portion of the garment 12 (e.g., a portion that has been folded over, a top portion of a garment, a portion having sensors, a portion having a tail of a sensor, etc.) For example, monitoring method 400 includes attaching a housing assembly to a folded portion of a garment 12, including an increased thickness portion. For example, monitoring method 400 includes securing a folder portion of the garment 12 within a clip 20 of the monitoring device 10. In some non-limiting embodiments, monitoring method 400 includes providing a secure attachment between the monitoring device 10 and the garment 12, and pins 52, attached to a printed circuit board 46 of a clip 20, extending into sensors 48 to both power and receive a signal from the sensors 48.

As shown in FIG. 29, at step 410, monitoring method 400 includes transmitting an electronic signal with information responsive to a sensor attachment. For example, monitoring method 400 includes a monitoring device 10 for electronically detecting a presence of moisture (e.g., a location, a quantity, a chemical composition, etc.) in a patient care or home care environment. In some non-limiting embodiments, monitoring device 10 can provide a detection of moisture across a network to a third-party device (e.g., a computer, a remote pad, a smartphone, a cloud) for enabling the remote collection and analysis of incontinence data. This detection can also be used by a third-party device, such as a monitoring system, to determine patterns and/or alert a caregiver associated with an incontinence event.

The monitoring device 10 of the present disclosure is directed to a monitoring device for detecting wetness in a garment. The monitoring device of the present disclosure includes a locking mechanism that slides back and forth relative to a clip that is removably attachable to a garment between a first position in which the locking mechanism locks the clip in a closed position and a second position in which the clip is in an open position. As the locking mechanism transitions from the first position to the second position, the locking mechanism opens the clip. Advantageously, the monitoring device of the present disclosure allows a caregiver to align and secure the monitoring device to a garment using only one hand.

In another exemplary embodiment of the present disclosure, referring to FIGS. 14, 17, 30, and 31, the clip 20 includes a printed circuit board 46 and a plurality of pins 52 in communication with the printed circuit board 46. In an exemplary embodiment, a portion of the plurality of pins 52 extend through a portion of the clip 20. With the clip 20 attached to a garment 12, the printed circuit board 46 is in communication with the garment 12 via the plurality of pins 52. For example, referring to FIGS. 17, 30, and 31, in one embodiment, the garment 12 includes a first conductive line 90 and a second conductive line 92 spaced from the first conductive line 90.

In one exemplary embodiment, the plurality of pins 52 include a first pin 82, a second pin 83, and a third pin 84. In one embodiment, the first pin 82 and the second pin 83 are aligned along a first axis 85 of the clip 20 and the third pin 84 is aligned along a second axis 86 of the clip 20. The second axis 86 of the clip 20 is spaced from the first axis 85 of the clip 20.

Advantageously, the system and clip 20 of the present disclosure monitors attachment and detachment information regarding the clip 20 being attached to the garment 12, and determines when the clip 20 becomes detached from the garment 12, and sends notification of when the clip 20 is detached from the garment 12. For example, the wearable clip 20 needs to stay on the garment 12 while a user or wearer of the clip 20 is moving around, sleeping, and doing other normal day to day activities.

Figure 30:
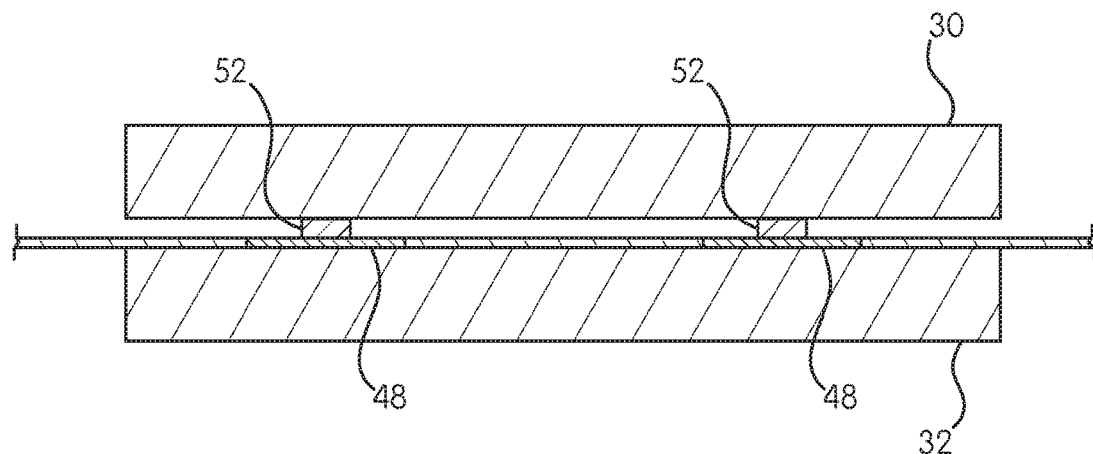
FIG. 30 is a cross-sectional view of a monitoring device attached to a garment in accordance with an embodiment of the present invention.
Figure 31:
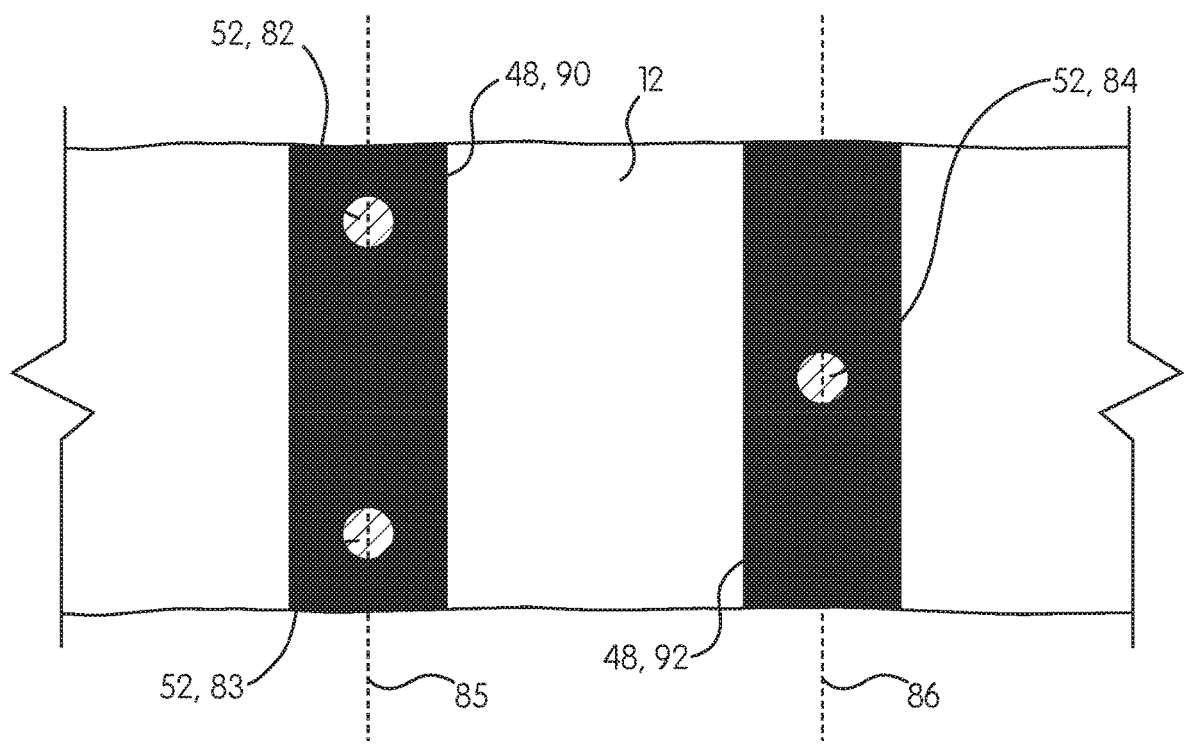
FIG. 31 is a schematical representation of a monitoring device attached to a garment in accordance with an embodiment of the present invention.

Referring to FIGS. 30 and 31, with the clip 20 attached to the garment 12, the first pin 82 and the second pin 83 communicate with the first line 90 and the third pin 84 communicates with the second line 92. With the first pin 82 and the second pin 83 in communication with the first line 90 of the garment 12, an attachment reading is generated to indicate that the clip 20 is attached to the garment 12.

With one of the first pin 82 and the second pin 83 not in communication with the first line 90 of the garment 12, a detachment reading is generated to indicate that the clip 20 is no longer attached to the garment 12. For example, a detachment reading is generated in any of the following situations: (A) with the first pin 82 not in communication with the first line 90 of the garment 12, (B) with the second pin 83 not in communication with the first line 90 of the garment 12, or (C) with both the first pin 82 and the second pin 83 not in communication with the first line 90 of the garment 12.

Furthermore, the transmitter of the monitoring device 10 has a built-in delay before sending the attachment/detachment signals to the gateway to filter out a rapid reading of "attach-detach-attach-detach-attach", e.g., flickering, which is triggered by a wearer of the monitoring device 10 moving around and/or other normal activity factors. In one embodiment, the delay waits for the attachment/detachment signal to settle, i.e., a signal not being followed by an opposite state signal, before sending attachment/detachment signals to the gateway. By using the delay at the transmitter level, the systems of the present disclosure can reduce the amount of false attachment/detachment reporting, the amount of signal transmission to the gateway-to-cloud, which results in lower battery consumption. In one embodiment, the cloud also filters flickering by imposing a set amount of delay, i.e., waits for the attachment/detachment signal to settle before displaying attachment status change on the touchscreen monitoring kiosk at the nurses' stations, for example.

Figure 32:
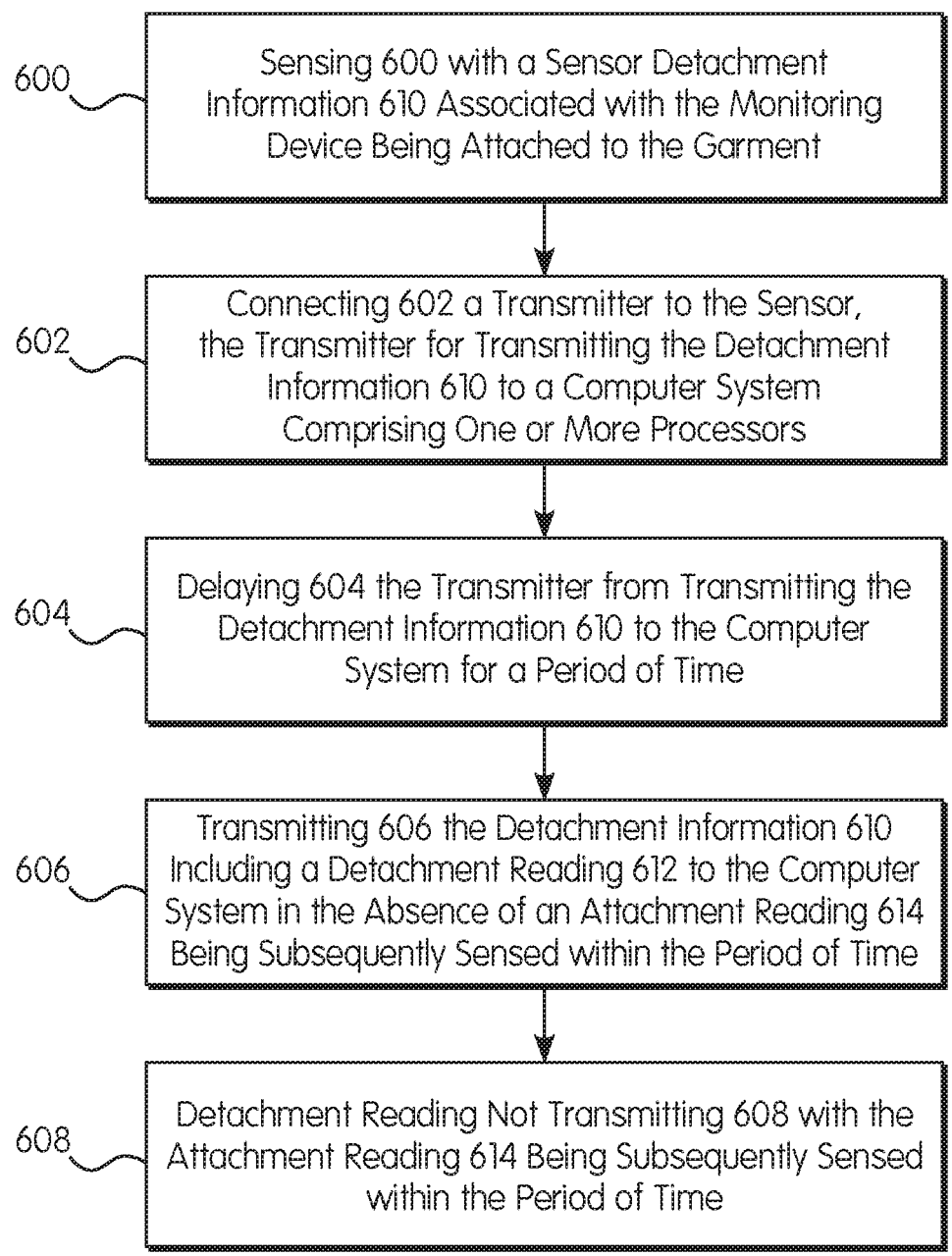
FIG. 32 is a flowchart of a non-limiting embodiment of a process and delay for monitoring a patient.

For example, referring to FIG. 32, in an exemplary embodiment of the present disclosure, a method for determining operational data for a monitoring device for detecting wetness in a garment includes: (1) sensing 600 with a sensor detachment information 610 associated with the monitoring device being attached to the garment, (2) connecting 602 a transmitter to the sensor, the transmitter for transmitting the detachment information 610 to a computer system comprising one or more processors, (3) delaying 604 the transmitter from transmitting the detachment information 610 to the computer system for a period of time, (4) transmitting 606 the detachment information 610 including a detachment reading 612 to the computer system in the absence of an attachment reading 614 being subsequently sensed within the period of time, and (5) wherein the detachment reading 612 is not transmitted 608 with the attachment reading 614 being subsequently sensed within the period of time. In one embodiment, the period of time is approximately three (3) seconds.

For example, in an exemplary embodiment of the present disclosure, a sensor 48 of the present disclosure is configured to determine detachment information 610 associated with the monitoring device 10 being attached to the garment 12 and a transmitter 50 of the present disclosure is configured to connect to a sensor 48 and transmit the detachment information 610 to a computer system comprising one or more processors. The transmitter 50 is configured to delay transmitting the detachment information 610 for a period of time. A detachment reading 612 is transmitted in the absence of an attachment reading 614 being subsequently sensed within the period of time. Furthermore, the detachment reading 612 is not transmitted with the attachment reading 614 being subsequently sensed within the period of time. In one embodiment, the transmitter 50 is configured to delay transmitting the detachment information 610 for a period of time based on the detachment information 610 indicating an attachment reading 614 after a detachment reading 612. In one embodiment, the period of time is approximately three (3) seconds.

Furthermore, the transmitter 50 of the monitoring device 10 has a built-in delay before sending a wetness signal to the gateway to filter out a rapid reading of "wet-dry-wet-dry-", e.g., flooding, which is triggered by sweat from a wearer of the monitoring device 10 while moving around and/or other factors that are not considered as a true wetness. In one embodiment, the delay waits for the wetness signal to settle, i.e., a signal not being followed by an opposite state signal such as a dry signal, before sending a wetness signal to the gateway. By using the delay at the transmitter level, the systems of the present disclosure can reduce the amount of false wetness reporting, the amount of signal transmission to the gateway-to-cloud, which results in lower battery consumption. In one embodiment, the cloud also filters flooding by imposing a set amount of delay before displaying wetness on a touchscreen monitoring kiosk at the nurses' stations, for example.

Figure 33:
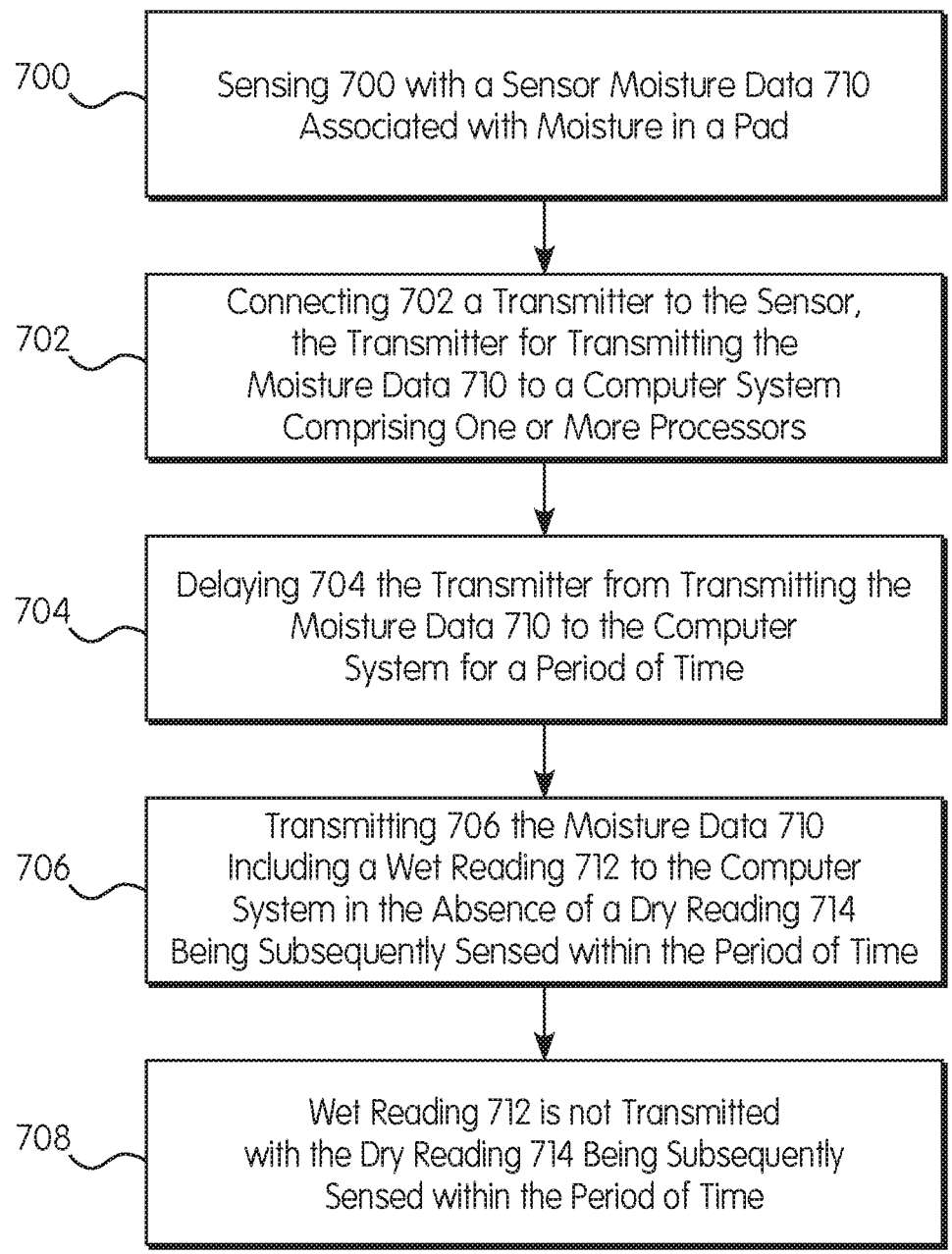
FIG. 33 is a flowchart of a non-limiting embodiment of a process and delay for monitoring a patient.

For example, referring to FIG. 33, in an exemplary embodiment of the present disclosure, a method for determining operational data for a monitoring device for detecting wetness in a garment includes: (1) sensing 700 with a sensor moisture data 710 associated with moisture in a pad, (2) connecting 702 a transmitter to the sensor, the transmitter for transmitting the moisture data 710 to a computer system comprising one or more processors, (3) delaying 704 the transmitter from transmitting the moisture data 710 to the computer system for a period of time, (4) transmitting 706 the moisture data 710 including a wet reading 712 to the computer system in the absence of a dry reading 714 being subsequently sensed within the period of time, and (5) wherein the wet reading 712 is not transmitted 708 with the dry reading 714 being subsequently sensed within the period of time. In one embodiment, the period of time is approximately five (5) seconds.

For example, in an exemplary embodiment of the present disclosure, a sensor 48 of the present disclosure is configured to determine moisture data 710 associated with moisture in a pad and a transmitter 50 of the present disclosure is configured to connect to a sensor 48 and transmit the moisture data 710 to a computer system comprising one or more processors. The transmitter 50 is configured to delay transmitting the moisture data 710 for a period of time. A wet reading 712 is transmitted in the absence of a dry reading 714 being subsequently sensed within the period of time. Furthermore, the wet reading 712 is not transmitted with the dry reading 714 being subsequently sensed within the period of time. In one embodiment, the transmitter 50 is configured to delay transmitting the moisture data 710 for a period of time based on the moisture data 710 indicating a dry reading 714 after a wet reading 712. In one embodiment, the period of time is approximately five (5) seconds.

Figure 34:
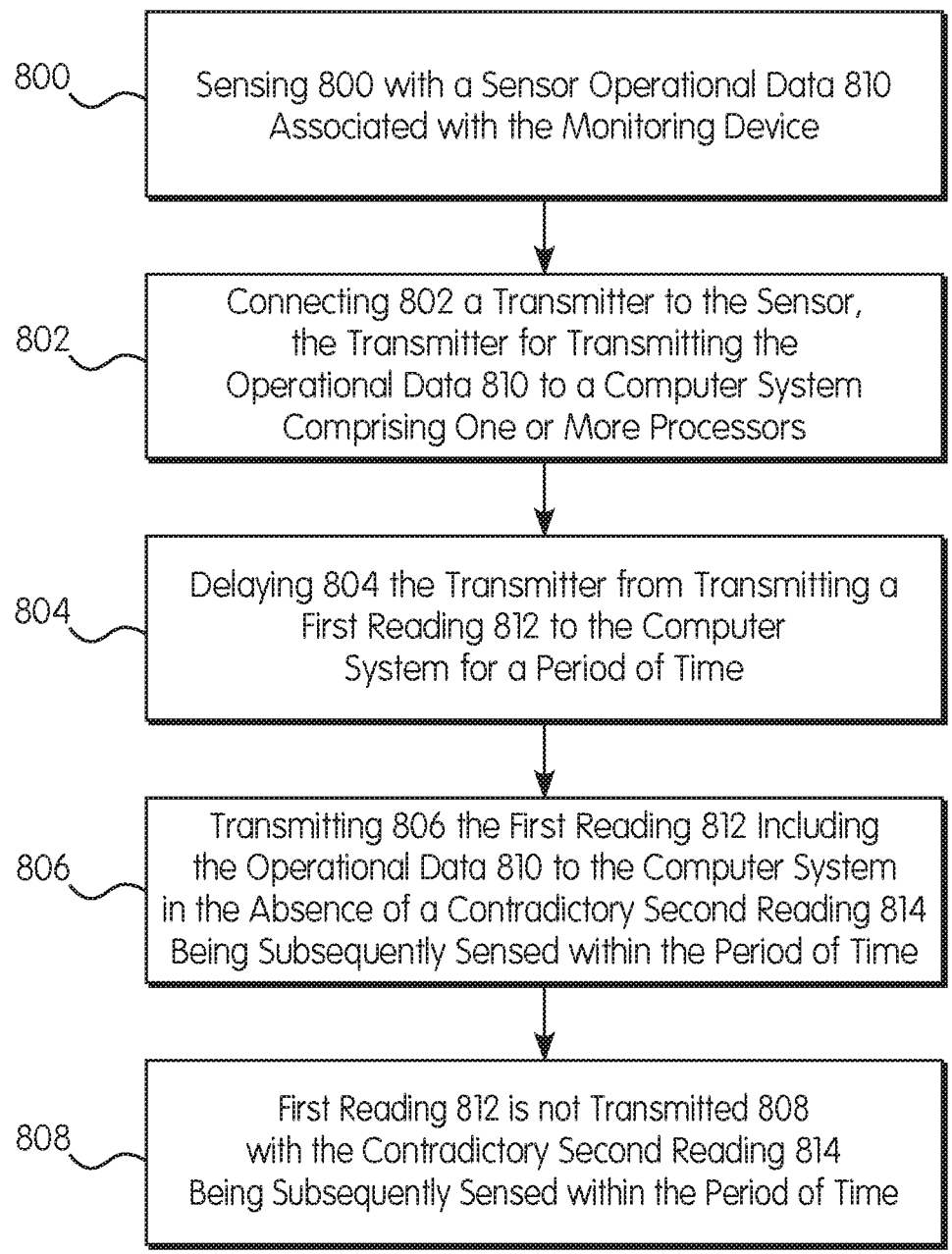
FIG. 34 is a flowchart of a non-limiting embodiment of a process and delay for monitoring a patient.

Furthermore, referring to FIG. 34, in an exemplary embodiment of the present disclosure, the monitoring device 10 of the present disclosure may include a sensor 48 of the present disclosure that is configured to determine operational data 810 associated with the monitoring device 10 and a transmitter 50 of the present disclosure that is configured to connect to a sensor 48 and transmit the operational data to a computer system comprising one or more processors. The transmitter 50 is configured to delay transmitting the operational data 810 for a period of time. A first reading 812 including the operational data 810 is transmitted in the absence of a contradictory second reading 814 being subsequently sensed within the period of time. Furthermore, the first reading 812 including the operational data 810 is not transmitted with the second reading 814 being subsequently sensed within the period of time.

For example, referring to FIG. 34, in an exemplary embodiment of the present disclosure, a method for determining operational data for a monitoring device for detecting wetness in a garment includes: (1) sensing 800 with a sensor operational data 810 associated with the monitoring device, (2) connecting 802 a transmitter to the sensor, the transmitter for transmitting the operational data 810 to a computer system comprising one or more processors, (3) delaying 804 the transmitter from transmitting a first reading 812 to the computer system for a period of time, (4) transmitting 806 the first reading 812 including the operational data 810 to the computer system in the absence of a contradictory second reading 814 being subsequently sensed within the period of time, and (5) wherein the first reading 812 is not transmitted 808 with the contradictory second reading 814 being subsequently sensed within the period of time.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A monitoring device for detecting wetness in a garment, comprising:
   a sensor configured to determine operational data associated with the monitoring device; and
   a transmitter configured to connect to the sensor and transmit the operational data to a computer system comprising one or more processors,
   wherein the transmitter is configured to transmit the operational data after a period of time,
   wherein a first reading including the operational data is transmitted in an absence of a contradictory second reading being subsequently sensed within the period of time, and
   wherein the first reading including the operational data is not transmitted with the second reading being subsequently sensed within the period of time.

2. The monitoring device of claim 1, wherein the operational data is moisture data associated with moisture in a pad.

3. The monitoring device of claim 2, wherein the first reading is a wet reading and the second reading is a dry reading.

4. The monitoring device of claim 2, wherein the transmitter is configured to transmit the moisture data after the period of time based on the moisture data indicating a dry reading after a wet reading.

5. The monitoring device of claim 1, wherein the period of time is approximately five (5) seconds.

6. The monitoring device of claim 1, wherein the operational data is detachment information associated with the monitoring device being attached to the garment.

7. The monitoring device of claim 6, wherein the first reading is a detachment reading and the second reading is an attachment reading.

8. The monitoring device of claim 6, wherein the transmitter is configured to delay transmitting the detachment information for a period of time based on the detachment information indicating an attachment reading after a detachment reading.

9. The monitoring device of claim 1, wherein the period of time is approximately three (3) seconds.

10. A monitoring device for detecting wetness in a garment, comprising: a sensor configured to determine moisture data associated with moisture in a pad; and a transmitter configured to connect to the sensor and transmit the moisture data to a computer system comprising one or more processors, wherein the transmitter is configured to transmit the moisture data after a period of time, wherein a wet reading is transmitted in an absence of a dry reading being subsequently sensed within the period of time, and wherein the wet reading is not transmitted with the dry reading being subsequently sensed within the period of time.

11. The monitoring device of claim 10, wherein the transmitter is configured to delay transmitting the moisture data for the period of time based on the moisture data indicating the dry reading after the wet reading.

12. The monitoring device of claim 10, wherein the period of time is approximately five (5) seconds.

13. The monitoring device of claim 10, wherein the transmitter is configured to delay transmitting the detachment information for the period of time based on the detachment information indicating the attachment reading after the detachment reading.

14. The monitoring device of claim 10, wherein the period of time is approximately three (3) seconds.

* * * * *